(12) United States Patent
Akers et al.

(10) Patent No.: US 11,284,205 B2
(45) Date of Patent: *Mar. 22, 2022

(54) SYSTEMS, DEVICES, AND METHODS FOR TREATING VESTIBULAR CONDITIONS

(71) Applicant: Otolith Sound Inc., Washington, DC (US)

(72) Inventors: Jonathan Akers, Washington, DC (US); Samuel Owen, Alexandria, VA (US); Didier Depireux, Ellicott City, MD (US); Robert True, Pleasant Prairie, WI (US)

(73) Assignee: Otolith Sound Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,484

(22) Filed: Jul. 6, 2020

(65) Prior Publication Data
US 2021/0321205 A1    Oct. 14, 2021

Related U.S. Application Data

(63) Continuation of application No. PCT/US2020/032693, filed on May 13, 2020, and a
(Continued)

(51) Int. Cl.
*H04R 25/00* (2006.01)
*A61M 21/00* (2006.01)

(52) U.S. Cl.
CPC .......... *H04R 25/606* (2013.01); *A61M 21/00* (2013.01); *H04R 25/75* (2013.01);
(Continued)

(58) Field of Classification Search
CPC .......... H04R 25/606; H04R 25/00–75; H04R 2225/00–83; H04R 2460/13; H04R 2460/00–17; A61M 21/00–02
See application file for complete search history.

(56) References Cited

U.S. PATENT DOCUMENTS 2,680,158 A   6/1954 Wolff
3,984,707 A   10/1976 McClintock
(Continued)

FOREIGN PATENT DOCUMENTS

CN   1853444 A    10/2006
CN   103430573 A  12/2013
(Continued)

OTHER PUBLICATIONS

Office Action for U.S. Appl. No. 15/980,124, dated Sep. 9, 2020, 15 pages.
(Continued)

*Primary Examiner* — Thaddeus B Cox
(74) *Attorney, Agent, or Firm* — Cooley LLP

(57) ABSTRACT

Apparatus and methods are described herein that provide a vibratory device that can apply a vibratory signal to a portion of a head of a user such that the vibratory signal can be conducted via bone to a vestibular system of the user and cause a portion of the vestibular system to move in a manner equivalent to that of a therapeutically effective vibratory signal applied to an area overlaying a mastoid bone of the user. The vibratory device can be associated with frequencies less than 200 Hz. The vibratory device can be effective at treating a physiological condition associated with the vestibular system.

20 Claims, 58 Drawing Sheets

Related U.S. Application Data continuation-in-part of application No. PCT/US2019/017497, filed on Feb. 11, 2019, which is a continuation-in-part of application No. 15/982,867, filed on May 17, 2018, now Pat. No. 10,398,897, which is a continuation-in-part of application No. 15/481,457, filed on Apr. 7, 2017, now abandoned.

(60) Provisional application No. 62/847,757, filed on May 14, 2019, provisional application No. 62/629,197, filed on Feb. 12, 2018, provisional application No. 62/629,213, filed on Feb. 12, 2018, provisional application No. 62/421,708, filed on Nov. 14, 2016.

(52) U.S. Cl.
CPC ............ *A61M 2021/0022* (2013.01); *A61M 2021/0027* (2013.01); *A61M 2230/06* (2013.01); *A61M 2230/205* (2013.01); *A61M 2230/50* (2013.01); *A61M 2230/63* (2013.01); *A61M 2230/65* (2013.01); *H04R 2460/13* (2013.01)

(56) References Cited

U.S. PATENT DOCUMENTS

| | | |
|---|---|---|
| 4,222,393 A | 9/1980 | Hocks et al. |
| 4,354,067 A | 10/1982 | Yamada et al. |
| 4,495,940 A | 1/1985 | Takaishi |
| 4,558,703 A | 12/1985 | Mark |
| 4,813,403 A | 3/1989 | Endo |
| 5,050,587 A | 9/1991 | Sagara et al. |
| 5,167,236 A | 12/1992 | Junker |
| 5,323,468 A | 6/1994 | Bottesch |
| 5,325,872 A | 7/1994 | Westermann |
| 5,361,437 A | 11/1994 | Zhu et al. |
| 5,403,262 A | 4/1995 | Gooch |
| 5,611,771 A | 3/1997 | Taylor |
| 5,692,056 A | 11/1997 | Gardner |
| 5,788,656 A | 8/1998 | Mino |
| 5,795,287 A | 8/1998 | Ball et al. |
| 5,966,680 A | 10/1999 | Butnaru |
| 6,047,074 A | 4/2000 | Zoels et al. |
| 6,068,590 A | 5/2000 | Brisken |
| 6,077,237 A | 6/2000 | Campbell et al. |
| 6,193,677 B1 | 2/2001 | Cady |
| 6,210,321 B1 | 4/2001 | Di Mino et al. |
| 6,411,050 B1 | 6/2002 | Yoshinari et al. |
| 6,443,913 B1 | 9/2002 | Kania |
| 6,692,428 B1 | 2/2004 | Kania |
| 7,253,350 B2 | 8/2007 | Noro et al. |
| 7,442,147 B2 | 10/2008 | Matsuzaki et al. |
| 7,442,174 B2 | 10/2008 | Butler |
| 7,626,295 B2 | 12/2009 | Yamaguchi |
| 7,633,835 B1 | 12/2009 | Erikson et al. |
| 7,962,217 B2 | 6/2011 | Merfeld |
| 8,317,848 B1 | 11/2012 | Webb et al. |
| 8,355,788 B2 | 1/2013 | Mechlenburg et al. |
| 8,463,389 B1 | 6/2013 | Oths |
| 8,515,552 B2 | 8/2013 | Englehart |
| 8,579,796 B2 | 11/2013 | Winkler |
| 8,801,591 B1 | 8/2014 | Lasorso, Jr. |
| 8,849,407 B1 | 9/2014 | Danilov et al. |
| 9,289,349 B2 | 3/2016 | Doochin et al. |
| 9,999,835 B2 | 6/2018 | Watson |
| 10,398,897 B2 | 9/2019 | Owen et al. |
| 10,702,694 B2 | 7/2020 | Owen et al. |
| 2001/0051776 A1 | 12/2001 | Lenhardt |
| 2003/0195588 A1 | 10/2003 | Fischell et al. |
| 2004/0097839 A1 | 5/2004 | Epley |
| 2004/0199214 A1 | 10/2004 | Merfeld et al. |
| 2005/0015027 A1 | 1/2005 | Kojima |
| 2005/0184601 A1 | 8/2005 | Kweon et al. |
| 2005/0201574 A1 | 9/2005 | Lenhardt |
| 2006/0020161 A1 | 1/2006 | Mageras et al. |
| 2006/0233418 A1 | 10/2006 | Huang |
| 2007/0041595 A1 | 2/2007 | Carazo et al. |
| 2007/0149905 A1 | 6/2007 | Hanna |
| 2008/0036303 A1 | 2/2008 | Stevens |
| 2008/0036307 A1 | 2/2008 | Lu et al. |
| 2008/0214973 A1 | 9/2008 | Von Othegraven |
| 2008/0221489 A1 | 9/2008 | Madsen et al. |
| 2009/0005713 A1 | 1/2009 | Podrazhansky et al. |
| 2009/0072636 A1 | 3/2009 | Gruden |
| 2010/0141248 A1 | 6/2010 | Suzukawa |
| 2011/0071340 A1 | 3/2011 | McGuire |
| 2011/0152729 A1 | 6/2011 | Oohashi et al. |
| 2011/0278962 A1 | 11/2011 | Hong |
| 2012/0016431 A1 | 1/2012 | Paul et al. |
| 2012/0033849 A1 | 2/2012 | Kang |
| 2012/0106774 A1* | 5/2012 | Saiki .................. H04R 7/18 381/412 |
| 2012/0203309 A1 | 8/2012 | Englehart |
| 2012/0286765 A1* | 11/2012 | Heuvel ............... H04R 25/606 324/76.49 |
| 2012/0302929 A1 | 11/2012 | Tkachenko |
| 2013/0061736 A1 | 3/2013 | Wauke |
| 2013/0090520 A1 | 4/2013 | Redfield et al. |
| 2013/0123889 A1 | 5/2013 | Katz et al. |
| 2013/0169071 A1 | 7/2013 | Endo et al. |
| 2013/0184788 A1 | 7/2013 | Jaeger et al. |
| 2013/0225915 A1 | 8/2013 | Redfield et al. |
| 2013/0237746 A1 | 9/2013 | Veitl |
| 2013/0303953 A1 | 11/2013 | Lattner |
| 2014/0046230 A1 | 2/2014 | Winkler |
| 2014/0084710 A1 | 3/2014 | Endo et al. |
| 2014/0270276 A1 | 9/2014 | Iwakura et al. |
| 2014/0276193 A1 | 9/2014 | Doochin et al. |
| 2014/0309718 A1 | 10/2014 | Smith et al. |
| 2014/0350441 A1 | 11/2014 | Shafieloo |
| 2014/0363003 A1 | 12/2014 | Kupershmidt et al. |
| 2015/0018601 A1 | 1/2015 | Braun |
| 2015/0063611 A1 | 3/2015 | Hillbratt et al. |
| 2015/0063616 A1 | 3/2015 | Westerkull |
| 2015/0156581 A1 | 6/2015 | Efrati |
| 2015/0272817 A1 | 10/2015 | Knyrim |
| 2015/0282754 A1 | 10/2015 | Wackym et al. |
| 2015/0297444 A1 | 10/2015 | Tass |
| 2015/0325027 A1 | 11/2015 | Herman et al. |
| 2016/0051793 A1 | 2/2016 | Gibson-Horn |
| 2016/0067099 A1 | 3/2016 | Hayashi |
| 2016/0089298 A1 | 3/2016 | Owen |
| 2016/0228771 A1 | 8/2016 | Watson |
| 2016/0234588 A1 | 8/2016 | Timothy et al. |
| 2016/0234613 A1 | 8/2016 | Westerkull |
| 2016/0256347 A1 | 9/2016 | Zimmerman |
| 2016/0277821 A1 | 9/2016 | Kunimoto |
| 2017/0135896 A1 | 5/2017 | Snow |
| 2017/0171677 A1 | 6/2017 | Norris et al. |
| 2018/0133102 A1 | 5/2018 | Owen et al. |
| 2018/0185595 A1 | 7/2018 | Bogan et al. |
| 2018/0250494 A1 | 9/2018 | Hanbury |
| 2018/0256444 A1 | 9/2018 | Owen |
| 2018/0264266 A1 | 9/2018 | Owen et al. |
| 2019/0014425 A1 | 1/2019 | Liao et al. |
| 2020/0001085 A1 | 1/2020 | Owen et al. |

FOREIGN PATENT DOCUMENTS

| | | |
|---|---|---|
| CN | 104490517 A | 4/2015 |
| CN | 104799999 A | 7/2015 |
| CN | 104873374 A | 9/2015 |
| CN | 104967935 A | 10/2015 |
| CN | 205142506 U | 4/2016 |
| DE | 2846859 A1 | 5/1979 |
| EP | 2779696 A1 | 9/2014 |
| EP | 3054702 A1 | 8/2016 |
| JP | 2002-065871 | 3/2002 |
| JP | 2012165129 A | 8/2012 |
| WO | WO 1990/001966 | 3/1990 |
| WO | WO 2000/010361 | 2/2000 |
| WO | WO 2004/077658 | 9/2004 |
| WO | WO 2008/058567 | 5/2008 |

(56) References Cited

FOREIGN PATENT DOCUMENTS

| WO | WO 2009/029040 | 3/2009 |
|---|---|---|
| WO | WO 2015/143053 | 9/2015 |
| WO | WO 2018/089994 | 5/2018 |
| WO | WO 2019/157443 | 8/2019 |
| WO | WO 2020/090477 | 5/2020 |

OTHER PUBLICATIONS

Invitation to Pay Additional Fees and Partial International Search Report for International Application No. PCT/US2020/032693, dated Jul. 20, 2020, 12 pages.
International Search Report and Written Opinion for International Application No. PCT/US2020/032693, dated Sep. 18, 2020, 18 pages.
Office Action for U.S. Appl. No. 14/867,774, dated Jun. 27, 2017, 16 pages.
Office Action for U.S. Appl. No. 14/867,774, dated Feb. 22, 2016, 13 pages.
Office Action for U.S. Appl. No. 14/867,774, dated Jan. 6, 2017, 15 pages.
Office Action for U.S. Appl. No. 15/980,124, dated Mar. 16, 2020, 11 pages.
Extended European Search Report for European Application No. 17868920.4, dated May 8, 2020, 10 pages.
Office Action for U.S. Appl. No. 15/481,457, dated Sep. 1, 2017, 25 pages.
Office Action for U.S. Appl. No. 15/481,457, dated Jun. 29, 2018, 35 pages.
Office Action for U.S. Appl. No. 15/481,457, dated Dec. 13, 2018, 34 pages.
Office Action for U.S. Appl. No. 15/481,457, dated Oct. 10, 2019, 35 pages.
International Search Report and Written Opinion for International Application No. PCT/US2017/061520, dated Dec. 18, 2017, 13 pages.
Office Action for U.S. Appl. No. 15/982,867, dated Apr. 4, 2019, 25 pages.
Office Action for U.S. Appl. No. 16/557,217, dated Nov. 25, 2019, 33 pages.
International Search Report and Written Opinion for International Application No. PCT/US2019/017497, dated Jul. 12, 2019, 21 pages.
Dumas, G. et al., "Skull Vibration-Induced Nystagmus Test in Unilateral Superior Canal Dehiscence and Otosclerosis: a Vestibular Weber Test," Acta Oto-Laryngologica, 2014; 134:588-600.
Dumas, G. et al., "The Skull Vibration-Induced Nystagmus Test of Vestibular Function-A Review," Frontiers in Neurology, Mar. 2017, vol. 8, Article 41, pp. 1-18.
Dumas, G. et al., "How to perform the skull vibration-induced nystagmus test (SVINT)," European Annals of Otorhinolaryngology, Head and Neck Diseases 133 (2016) 343-348.
Ohki, M. et al., "Vibration-Induced Nystagmus in Patients with Vestibular Disorders," Otolaryngol Head Neck Surg 2003; 129:255-258.
Lee, S-U et al., "Head-Shaking and Vibration-Induced Nystagmus During and Between the Attacks of Unilateral Meniere's Disease," Otology & Neurotology, 36:865-872, 2015.
Sohmer, H. et al., "Effect of Noise on the Vestibular System—Vestibular Evoked Potential Studies in Rats," Noise & Health, 1999, vol. 2(5):41-51.
Beh, S. C. et al., "Damping of Monocular Pendular Nystagmus with Vibration in a Patient with Multiple Sclerosis," Neurology, Apr. 15, 2014; 82(15): 1380-1381.
Bone Conductor Transducer with Wires—8 Ohm 1 Watt, Product ID: 1674 [Online], Retrieved from the Internet: <URL: https://www.adafruit.com/product/1674>, Retrieved from the Internet on May 15, 2018, 7 pages.
Dayton Audio BCT-2 45 x 25mm Bone Conducting Transducer 240-612 [Online], Retrieved from the Internet: <URL: https://www.newegg.com/Product/Product.aspx?Item=9SIA88E3493965&ignorebbr=1&n . . . >, Retrieved from the Internet May 15, 2018, 2 pages.
Margolis, R. H. et al., "Acoustic method for calibration of audiometric bone vibrators," J. Acoust. Soc. Am. 131(2):1221-1225, Feb. 2012.
Medium Surface Transducer with Wires—4 Ohm 3 Watt, Product ID: 1785, [Online], Retrieved from the Internet: <URL: https://www.adafruit.com/product/1785>, Retrieved from the Internet on May 15, 2018, 5 pages.
Waveform generated by Bone Conducting Transducer 240-612, generated on Apr. 11, 2018, 1 page.
Waveform generated by Dayton Audio BCT-2 Bone Conduction Transducer, generated on Apr. 11, 2018, 1 page.
Waveform generated by Medium Surface Transducer with Wires—4 Ohm 3 Watt, generated on Apr. 11, 2018, 1 page.
Haybach, P. J., "Meniere's Disease," Vestibular Disorders Association [Online], Retrieved from the Internet: <https://vestibular.org/menieres-disease>, 4 pages (Jun. 2018).
First Office Action for Chinese Application No. 201780083234.9, dated Feb. 3, 2021, 13 pages.
Office Action for European Application No. 17868920.4, dated Mar. 19, 2021, 5 pages.

* cited by examiner

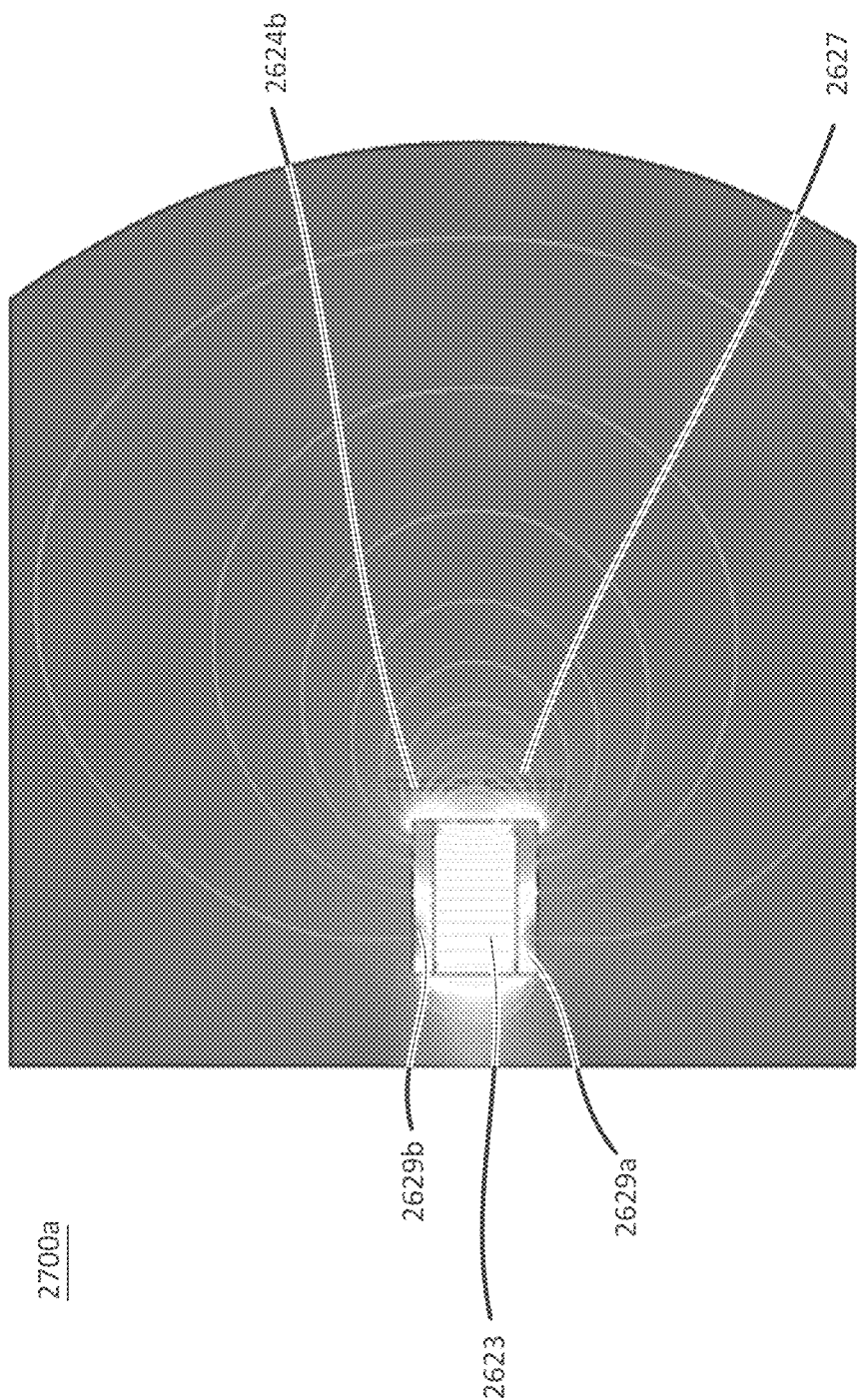

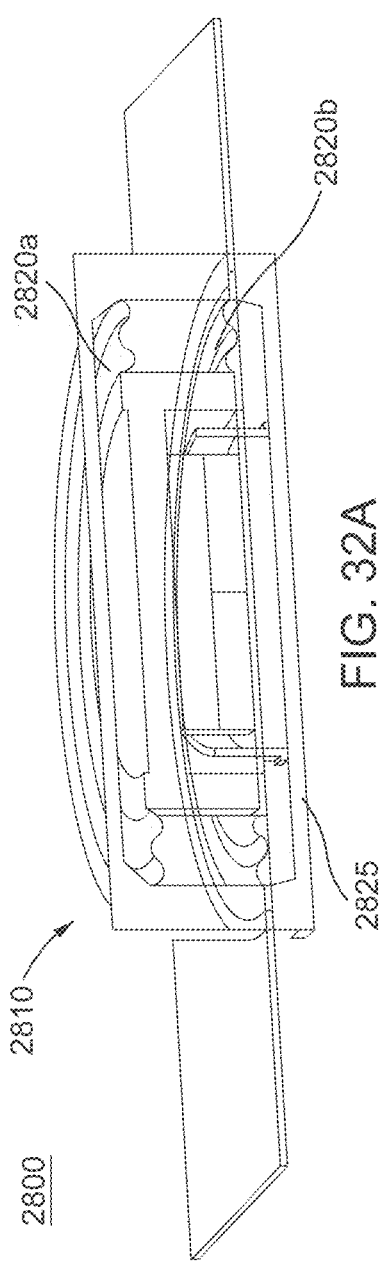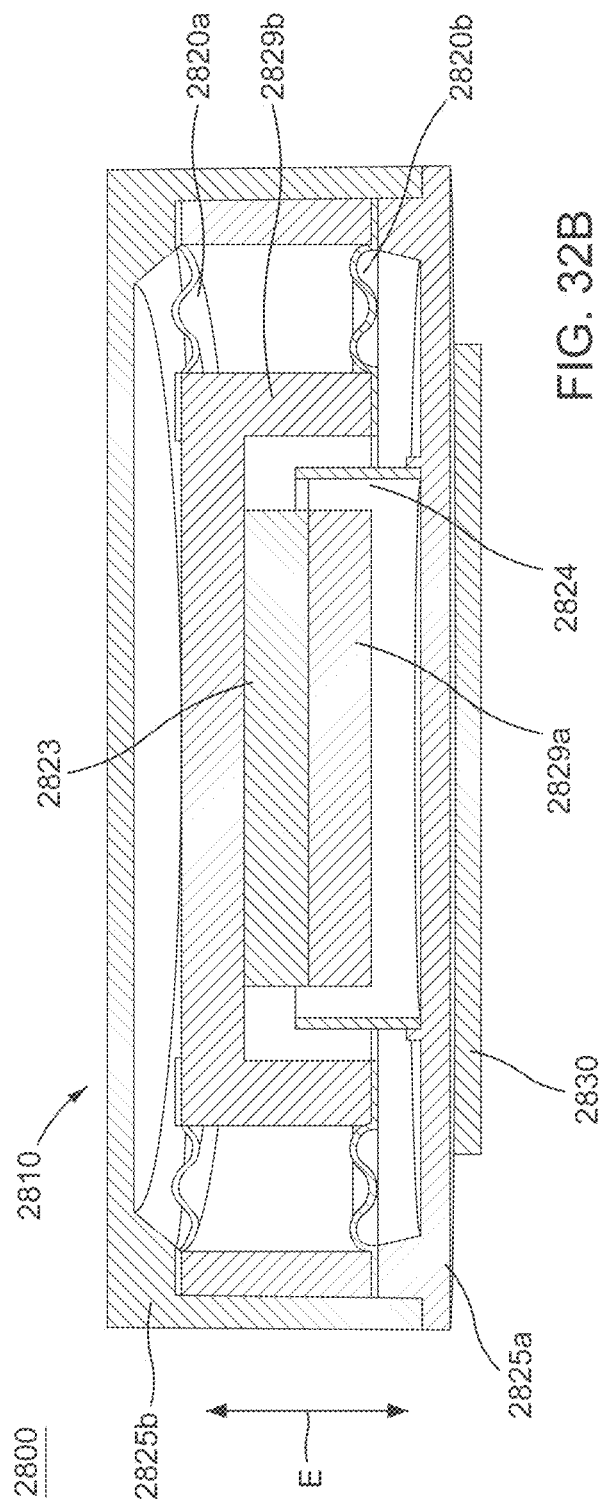

SYSTEMS, DEVICES, AND METHODS FOR TREATING VESTIBULAR CONDITIONS

CROSS-REFERENCES TO RELATED APPLICATIONS

This application is a continuation-in-part of application of International Patent Application No. PCT/US2019/017497, filed Feb. 11, 2019, entitled "Systems, Devices, And Methods For Treating Vestibular Conditions," and is a continuation of International Patent Application No. PCT/US2020/032693, filed May 13, 2020, entitled "Systems, Devices, And Methods For Treating Vestibular Conditions." International Patent Application No. PCT/US2019/017497 is a continuation-in-part application of U.S. patent application Ser. No. 15/982,867, filed May 17, 2018, now U.S. Pat. No. 10,398,897, issued Sep. 3, 2019, entitled "Systems, Devices, And Methods For Treating Vestibular Conditions," which is a continuation-in-part application of U.S. patent application Ser. No. 15/481,457, filed Apr. 7, 2017, entitled "Devices and Methods for Reducing the Symptoms of Maladies of the Vestibular System," now abandoned, which in turn claims priority to and the benefit of U.S. Provisional Application No. 62/421,708, filed Nov. 14, 2016, entitled "Devices and Methods for Treating Motion Sickness." U.S. patent application Ser. No. 15/982,867 also claims priority to U.S. Provisional Application No. 62/629,213, filed Feb. 12, 2018, entitled "Methods And Devices For Reducing Motion Sickness In Virtual Reality And Travel Applications," and U.S. Provisional Patent Application No. 62/629,197, filed Feb. 12, 2018, entitled "Methods and Devices for Treating the Proprioceptive Vestibular System." International Patent Application No. PCT/US2020/032693 claims priority to U.S. Provisional Application No. 62/847,757, filed May 14, 2019, entitled "Systems, Devices, And Methods For Treating Vestibular Conditions."

FIELD OF INVENTION

Disclosed embodiments relate to systems, devices, and methods for treating conditions such as, for example, motion sickness, dizziness, vertigo, migraines, tinnitus, and loss of consciousness, associated with a vestibular system of a subject. More specifically, the present disclosure relates to devices capable of generating vibratory signals that can affect a subject's vestibular system.

BACKGROUND

Orientation, balance, position, and movement of a body can be determined by the brain through a combination of signals received from various parts of anatomy, including eyes, ears, and muscles. For example, the vestibular system, in most mammals, is the sensory system that predominantly contributes sensory information related to balance and spatial orientation. The vestibular system of a subject is found in the inner ear of the subject, as shown in FIG. 1A, in a system of interconnected compartments forming the vestibular labyrinth.

An individual's inner ear has five receptors associated with balance: three associated with three semicircular canals, and two maculae in the vestibule (i.e., the utricle and the saccule). The utricle and the saccule are involved in measuring linear acceleration of the head, e.g., from self-movement and from constant acceleration of gravity. Each is covered by an otolithic membrane, as described below with reference to FIGS. 2A and 2B. Roughly, the utricle measures acceleration in a horizontal plane and the saccule measures acceleration in a vertical plane. FIG. 1A illustrates a portion of the anatomy of a subject 100, showing the vestibular system with respect to an external ear 110, portions of a skull 114, and bony portion of an ear 116, an ear canal 111, an ear drum 112, and the bones of a middle ear 113. The vestibular system includes semicircular canals 122, 124, and 126, and otolith organs 128 and 130, housed within a vestibule 121 in the bony labyrinth of the inner ear, and is continuous with a cochlea 120. FIG. 1B provides a more detailed illustration of the vestibular system shown in FIG. 1A, depicting the vestibule 121 to include a utricle 128 and a saccule 130.

The three semicircular canals 122, 124, and 126 are each oriented in a plane along one of three directions in which the head can rotate or move and detect motion in that direction, the directions being nodding up-down, shaking left-right, and tilting left-right. The otolith organs within the vestibule of the inner ear 121 detect gravitational forces and acceleration in the forward and backward directions. The otolith organs include the utricle 128 that detects movements in the horizontal plane and the saccule 130 that detects movements in the vertical plane. The semicircular canals 122, 124, and 126, and the otolith organs 128 and 130 are filled with endolymph, a fluid that moves with the movement of the head or body.

The movement of endolymph in the vestibular system of the inner ear can be sensed by nerve cells with hair bundles to determine movement and orientation of the head. Portions called ampula in the semicircular canals and macula in the otolith organs include hair cells, which function as the sensory receptors of the vestibular system and include hair bundles or stereocilia that detect and transduce movement of the endolymph into signals of body movement and report the signals to the brain. The otolith organs also include a layer of crystals of calcium carbonate called otoconia or otoliths that shift in response to changes in acceleration (e.g., changes in motion or orientation with respect to gravity) leading to movement in the layers below the otoconia and the movement of hair bundles. Additionally, otoliths sink in the direction of gravity and pull on bundles of hair cells to aid in distinguishing directions, e.g., up from down.

FIGS. 2A and 2B provide detailed views of the anatomy of the macula in the otolith organs (e.g., the utricle 128 and the saccule 130 shown in FIG. 1B) and the sensory receptors, in an upright state and in a state of movement, respectively. FIG. 2A shows the macula including an otolithic membrane 132 and a cellular layer including hair cells 134 and supporting cells 136. The hair cells 134 include hair like projections or stereocilia 132 that extend into one or more gelatinous layers. The organization of the macula also includes a layer of otoconia or otoliths 138 that shift in response to movement in the endolymph and/or to acceleration of the body. FIG. 2A shows the hair cells 134 and the otoliths 138 in an upright configuration, and FIG. 2B shows the hair cells 134 and the otoliths 138 in a displaced or angled configuration when a directional force 140 (e.g. gravity) acts on the otoliths 138. Similarly, movement of the endolymph within the semicircular canals 122, 124, and 126, can result in movement of the hair cells within the ampula of the semicircular canals (not shown) perceiving and signaling relative movement of the body and/or head (e.g., angular acceleration of the head).

In addition to signals from the vestibular system, horizontal and vertical visual patterns received by the eyes can affect perception of orientation, balance, and position; and differential strain on opposing neck muscles can affect perception of head position and orientation. When signals from these sources do not match, an individual can develop motion sickness, experience vertigo, dizziness, vestibular migraines, unconsciousness, or other conditions. Unmatched orientation, balance, position and movement signals can be the result of extreme or unfamiliar movement during, for example, travel in cars, trains, airplanes, and other modes of transportation. Unmatched signals may also result from simulated perceived movement during, for example, three dimensional (3D) movies, 3D video games, and virtual reality devices. Therefore, it can be desirable to have a device for treating various vestibular conditions that may result from unmatched signals being received from a subject's vestibular system, eyes, or other anatomy.

SUMMARY

Apparatus and methods described herein can include a vibratory device configured to apply a vibratory signal to a portion of a head of a user such that the vibratory signal can be conducted via bone to a vestibular system of the user and cause a portion of the vestibular system to move in a manner equivalent to that of a therapeutically effective vibratory signal applied to an area overlaying a mastoid bone of the user. The therapeutically effective vibratory signal can (1) have a frequency less than 200 Hz and a force level between 87 and 101 dB re 1 dyne and (2) being therapeutically effective to treat a physiological condition associated with the vestibular system.

Apparatus and methods are described herein can, in some embodiments, include a vibratory device configured to apply a set of vibratory signals to a portion of a head of a user such that the set of vibratory signals can be conducted via bone to a vestibular system of the user to treat a physiological condition associated with the vestibular system. The vibratory device can be associated with a set of resonant frequencies including a lowest resonant frequency that is less than 200 Hz. The set of vibratory signals can collectively have an amount of power at the lowest resonant frequency that is greater than an amount of power at remaining resonant frequencies from the set of resonant frequencies.

In some embodiments, apparatus described herein can include a vibrating element configured to apply a vibratory signal to a portion of a head of a user such that the vibratory signal can be conducted via bone to a vestibular system of the user to treat a physiological condition associated with the vestibular system. The vibrating element can be configured to include a housing defining a chamber, a magnet movable within the chamber to produce the vibratory signal, a suspension element configured to suspend the magnet at a position within the chamber, and a coil configured to generate a magnetic field to cause the magnet to move about the position.

Methods disclosed herein include positioning a vibratory device over an area of a head of a user, and energizing the vibratory device, after the positioning, to apply a vibratory signal to the area such that the vibratory signal can be conducted via bone to a vestibular system of the user. The vibratory signal can be configured to cause a portion of the vestibular system to move in a manner equivalent to that of a vibratory signal (1) applied to an area overlaying a mastoid bone of the user and having (2) a frequency less than 200 Hz and a force level between 87 and 101 dB re 1 dyne. The methods can further include treating, in response to energizing the vibratory device, a physiological condition associated with the vestibular system.

In some embodiments, an apparatus includes a vibratory device configured to produce a vibratory signal and apply the vibratory signal to a portion of a head of a user such that the vibratory signal can be conducted via bone to a vestibular system of the user; a biometric sensor configured to measure a biological characteristic of the user that is indicative of an onset of a physiological condition associated with the vestibular system of the user; a control unit operatively coupled to the vibratory device and the biometric sensor, the control unit configured to: receive data associated with the biological characteristic from the biometric sensor; and control the vibratory device to produce the vibratory signal based on the data associated with the biological characteristic such that the vibratory signal is applied to the portion of the head to treat the physiological condition.

In some embodiments, an apparatus includes: a vibratory device configured to produce a vibratory signal and apply the vibratory signal to a portion of a head of a user such that the vibratory signal can be conducted via bone to a vestibular system of the user, the vibratory device including: a housing defining a chamber; a magnet disposed within the chamber and configured to oscillate about an equilibrium position to produce the vibratory signal; a coil configured to generate a magnetic field that can cause the magnet to oscillate; a set of metallic components coupled to the ends of the magnet and configured to reduce stray magnetic flux and direct a magnetic field of the magnet in a direction for enabling oscillation of the magnet; and at least one suspension component configured to suspend the magnet within the chamber such that the magnet can oscillate about the equilibrium position.

In some embodiments, a method includes receiving, from a biometric sensor operatively coupled to a vibratory device positioned over a portion of a head of a user, data associated with a biological characteristic of the user; detecting, based on the data, an onset of a physiological condition associated with a vestibular system of the user; and in response to detecting the onset of the physiological condition, activating the vibratory device to produce a vibratory signal to be applied to the head of the user such that the vibratory signal can be conducted via bone to the vestibular system to reduce a symptom associated with the physiological condition.

In some embodiments, a method includes receiving, from a biometric sensor operatively coupled to a vibratory device positioned over a portion of a head of a user, data associated with a biological characteristic of the user; detecting, based on the data, a change in severity of a physiological condition associated with a vestibular system of the user; in response to detecting an increase in the severity of the physiological condition, increasing a force level of a vibratory signal produced by the vibratory device and being applied to the head of the user and conducted via bone to the vestibular system to reduce a symptom associated with the physiological condition; and in response to detecting a decrease in the severity of the physiological condition, decreasing the force level of the vibratory signal.

BRIEF DESCRIPTION OF THE DRAWINGS

FIG. 29 is an illustration of magnetic field lines associated with a magnet of a vibratory device, such as the vibratory device of FIG. 38.

FIGS. 32A and 32B are schematic illustrations of two different cross-sectional views of the vibratory device of FIGS. 31A-31C.

DETAILED DESCRIPTION

Figure 1A:
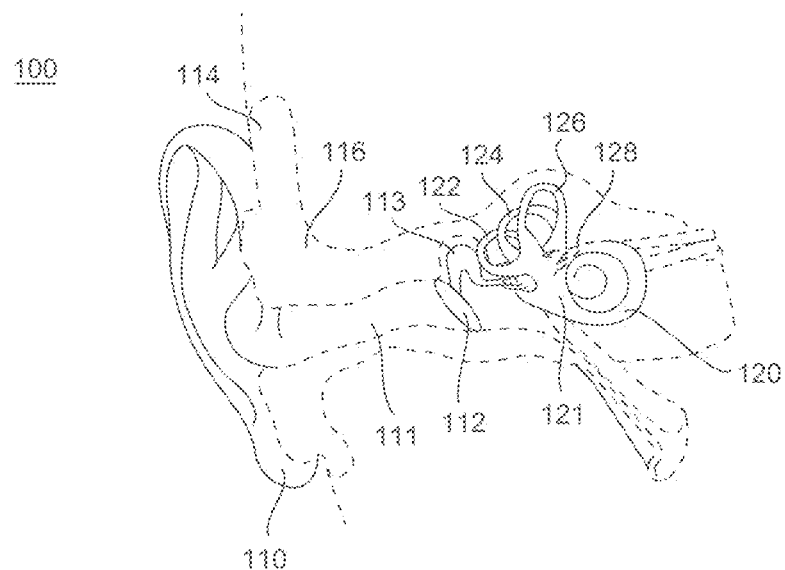
FIG. 1A illustrates an anatomy of a subject, including a bony labyrinth of an inner ear housing a vestibular system.
Figure 1B:
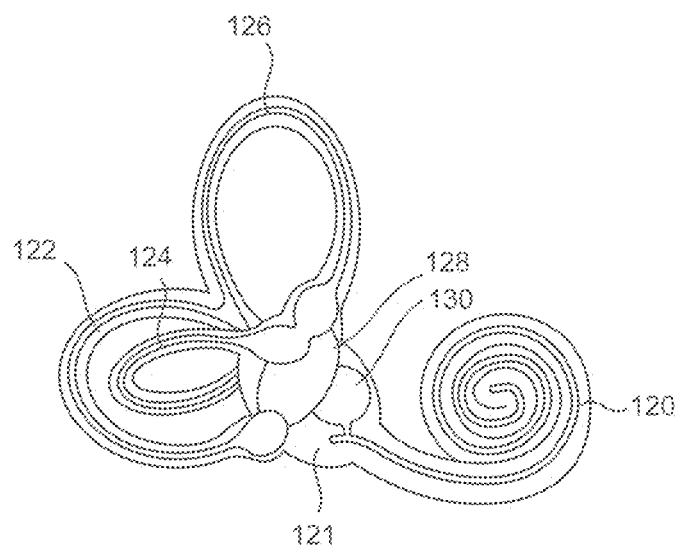
FIG. 1B provides a detailed illustration of the vestibular system and the cochlea, within the bony labyrinth of FIG. 1A.
Figure 2A:
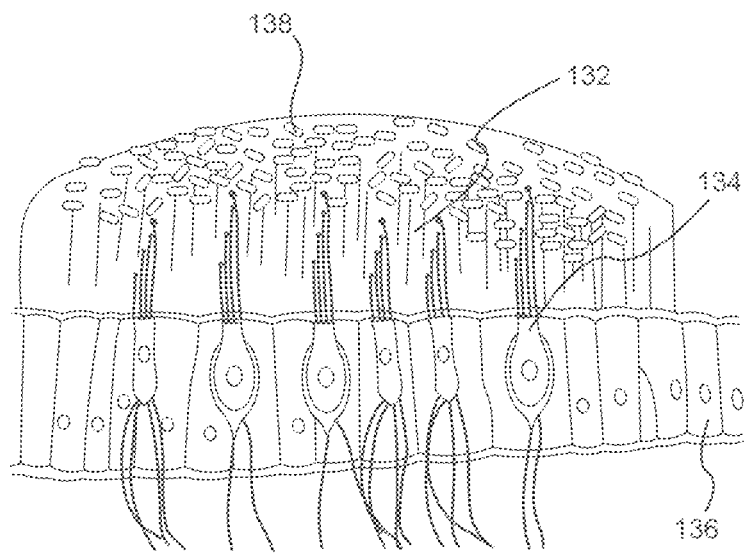
FIGS. 2A and 2B are illustrations of a portion of a macula of the otolith organs shown in FIG. 1B, in an upright state and in a state of experiencing a directional force, respectively.
Figure 2B:
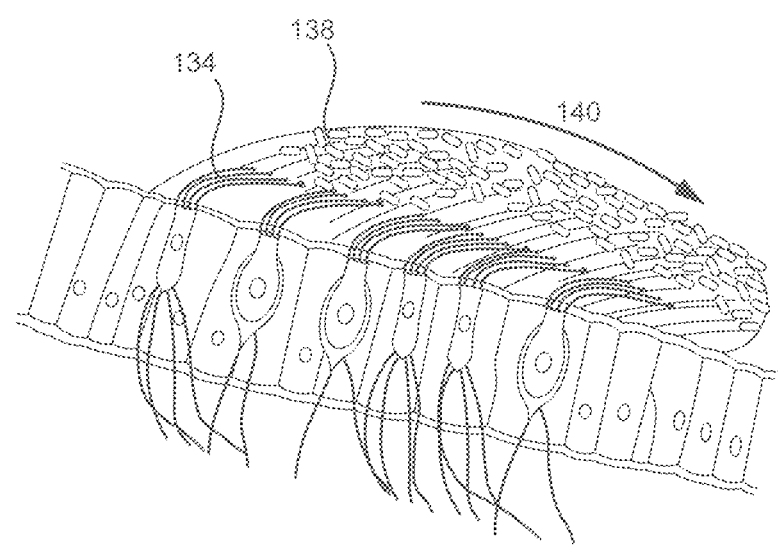

Apparatus and methods are described herein for treating vestibular conditions by using a vibratory device capable of generating vibratory signals and applying the vibratory signals via bone conduction to a vestibular system of a subject such that the vibratory signals can disrupt an anatomy of the subject's vestibular system.

As described above, sensory signals from a vestibular system of a subject aid in the perception of orientation, balance, position, and movement of a body of the subject. In addition to signals from the vestibular system, other sensory modalities, such as visual signals from the eyes, can affect perceptions of orientation, balance, and position; and differential strain on opposing neck muscles can affect perceptions of head position and orientation. When signals from these various sensory sources such as the vestibular system, the visual system, and the proprioceptive system do not match, an individual can develop conditions like motion sickness, vertigo, dizziness, vestibular migraines, unconsciousness, or other conditions. For example, unmatched orientation, balance, position, and movement signals can result from extreme or unfamiliar movement during, for example, travel in cars, trains, airplanes, and other modes of transportation, or result from experiencing virtual or augmented 3D environments such as 3D movies, 3D video games, virtual reality devices, etc.

In a natural adaptive response, a brain can ignore sensory information in signals that are chaotic, repetitive or not novel, or unintelligible. For example, it has been shown that vibrations from sound can affect the vestibular organs in the inner ear and decrease response (e.g., an amplitude of electrical signals) in the cerebellum. See H. Sohmer et al., "Effect of noise on the vestibular system—Vestibular evoked potential studies in rats," 2 Noise Health 41 (1999). Nonetheless, the same studies have shown that very high intensities are required in order for sound to affect the vestibular system. Thus, traditional headphones, earphones, and speakers, used to produce sound from generating vibratory signals in the air, are limited in their ability to treat symptoms like motion sickness response, vertigo, vestibular migraines, and other physiological responses. Many of these technologies are not designed to deliver high intensity signals. Moreover, such high intensity signals may harm or disrupt human hearing.

As an alternative to using sound, mechanical vibrations can be used to affect the vestibular system to therapeutically treat various conditions. One technology that can be used to create mechanical vibrations is a surface or bone conduction transducer. Presently available bone conduction transducers, however, have certain drawbacks associated with treating symptoms or conditions of the vestibular system. For example, existing devices often have significant limitations, such as production of a significant amount of heat and/or audible noise, which can prevent their use in direct contact with a person's skin or in close proximity to a person's ear. Many existing devices are also large and bulky, which make them impractical for use under circumstances where the therapeutics effects are needed, such as, for example, during travel, while reading, while using a virtual reality device, etc.

Existing devices, such as a surface or bone conduction transducer, are inefficient at producing low frequency vibrations. Many produce vibratory signals at high frequencies that are audible and therefore distracting. Accordingly, when such devices are used close to a person's ear, the noise they create can be disruptive and irritating. Many existing devices produce high frequency vibrations in large part due to power being directed to higher, resonant frequencies instead of the lower, fundamental frequency of a vibratory signal being generated by such a transducer. Even when designed to produce low frequency vibrations, existing bone conduction transducers may be inefficient because they produce a large spectrum of frequencies (e.g., frequencies at many harmonics) when the lower frequencies are the ones that are needed. Accordingly, disclosed systems and methods are directed to the treatment of symptoms associated with conditions of the vestibular system that do not produce a high level of heat or audible noise, and have high efficiency in delivering lower frequency vibratory signals, among other features.

I. Overview

Figure 3:
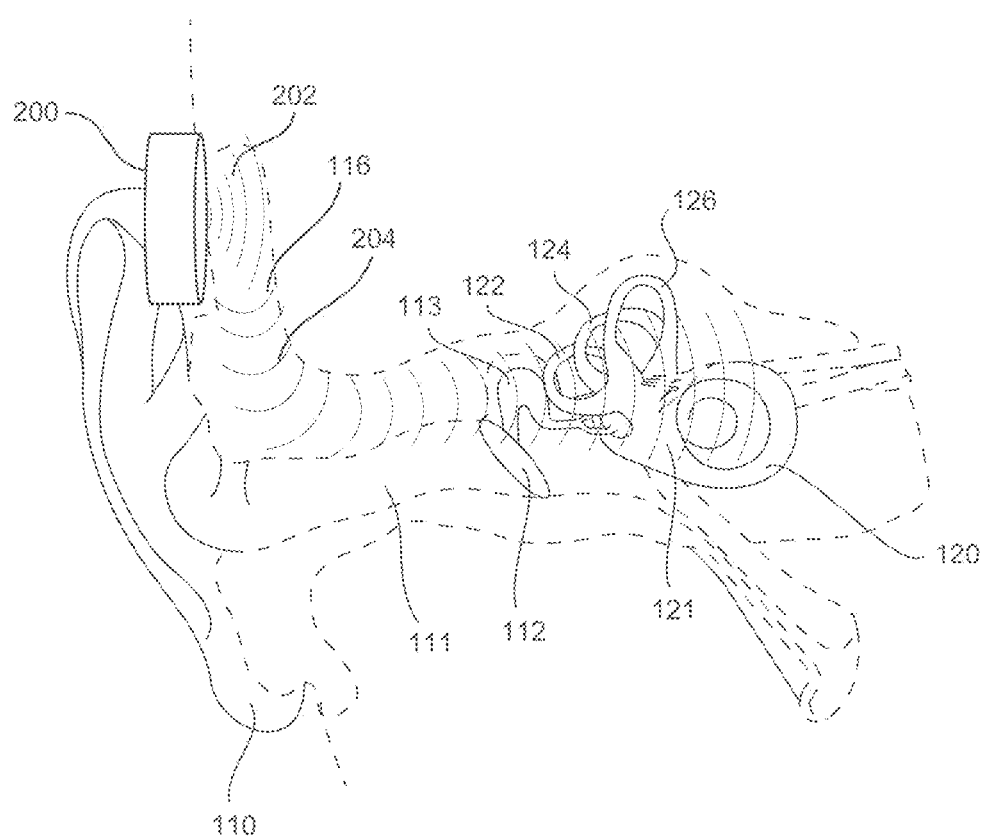
FIG. 3 is a schematic illustration of a placement of a vibratory device to apply vibratory signals to the vestibular system, according to an embodiment.

FIG. 3 schematically illustrates the placement of a vibratory device 200 near an external ear 110 of a subject. The vibratory device 300 can be configured to apply vibratory signals 202 conducted via bone to treat one or more symptoms or conditions associated with the subject's vestibular system. A portion 204 of the vibratory signals 202 can be conducted via bone 116 to the bony labyrinth of the inner ear and to the vestibular system. For example, the portion 204 of the vibratory signals travels though the bone to the semicircular canals 122, 124, and 126 and the vestibule 121 housing the otolith organs, the utricle and the saccule.

The vibratory device 200 can be positioned such that vibratory signals can be applied to the vestibule 121 to cause the hair cells in the otolith organs in the vestibule 121 and the semicircular canals 122, 124, and 126 to move in a repetitive, chaotic, or noisy manner to reduce, mitigate, or treat symptoms associated with vestibular conditions. Some example vestibular conditions can include various types of motion sickness (e.g., sea sickness, air sickness, car and train sickness, sickness from exposure to virtual reality or simulators, sickness from experiences such as rides on a roller coaster, and effects of sopite syndrome), vertigo such as benign paroxysmal positional vertigo, nausea from a variety of causes (e.g., vestibular system testing including caloric electronystagmography (ENG)/videonystagmography (VNG) testing, head impulse testing, vestibular evoked myogenic potential (VEMP) testing such as cervical VEMP and ocular VEMP testing, functional gait assessment, etc., or arising from conditions such as chemotherapy, radiotherapy of a base of the skull, nausea related to pregnancy, nausea from alcohol or poison consumption, etc.), infection, vestibular neuritis, vestibular schwannoma, Meniere's disease, tinnitus, migraines, Mal de Debarquement syndrome, spatial discordance, sopite syndrome, vestibular weakness, general imbalance, etc.

The vibratory device 200 can also be positioned, as described herein, to provide vibratory signals conducted via bone to treat other conditions, including, for example, dizziness, loss of balance, etc. caused by circulatory problems (e.g., orthostatic hypotension (drop in blood pressure), poor blood circulation from cardiomyopathy, heart attack, arrhythmia, transient ischemic attack), neurological conditions (e.g., Parkinson's disease, multiple sclerosis), medications (e.g., anti-seizure drugs, antidepressants, sedatives, tranquilizers, blood pressure lowering medications), anxiety disorders, anemia due to low iron levels, hypoglycemia (lowered blood sugar), overheating, dehydration, and traumatic brain injury. The vibratory signal can cause a portion of the vestibular system to move in a manner equivalent to that of a therapeutically effective vibratory signal to treat the above described conditions. Moreover, the vibratory device 200 can be used to assist pilots such as, for example, to train pilots to ignore or reject their vestibular system under specific conditions. The vibratory device 200 can also be used as a stroke diagnostic.

Figure 4A:
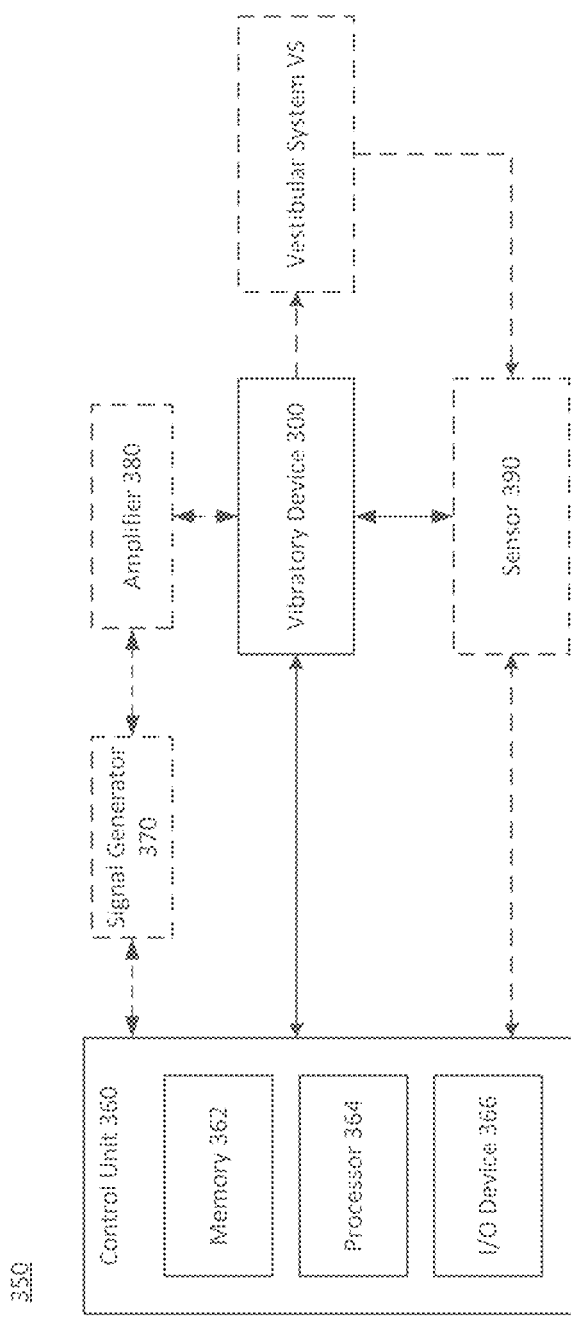
FIG. 4A is a schematic illustration of an example system for treating symptoms associated with vestibular conditions, according to an embodiment.

FIG. 4A schematically illustrates an example system 350 for treating vestibular conditions. The system 350 includes a vibratory device 300 and a control unit 360 coupled to the vibratory device 300 for activating and/or controlling the operation of the vibratory device 300. The vibratory device 300 can be an electro-mechanical transducer configured to generate vibratory signals when driven and energized by appropriate electrical signals from a signal source. The control unit 360 can include a memory 362, a processor 364, and an input/output (I/O) device 366 for receiving and/or sending electrical signals to and/or from other components of system 350. The vibratory device 300 can be configured to receive and/or send electrical signals to the control unit 360. Optionally, the system 350 can include one or more sensor(s) 390 for measuring voltage, current, impedance, movement, acceleration, or other data associated with the vibratory device 300. Alternatively or additionally, the sensor(s) 390 can be configured to measure information associated with a vestibular system VS of a subject and/or other body metrics (e.g., temperature, skin conductivity, etc.). The sensor(s) 390 can receive and send signals to the control unit 360, the vibratory device 300, and/or the vestibular system VS. As an example, the sensor(s) 390 can include a microphone or other sound sensor that can be used to detect whether the vibratory device 300 has a failure resulting in an audible sound caused by the vibrations that are generated. The sensor 390 can be configured to detect audible sound and send a signal to the control unit 360, which can deactivate the vibratory device 300, signal generator 370, and/or other components of the system such that the audible sound is reduced. Alternatively, the system 350 can include circuitry that automatically deactivates the system, e.g., cuts power to the vibratory device 300, the signal generator 370 and/or other components of the system, upon detection of audible sound. Once deactivated, the system 350 can remain deactivated until the system 350 receives maintenance and/or a factory reset. In some embodiments, the system 350 can include noise cancelling components, such as described with reference to FIG. 11, which can activate in response to noise being detected by sensor 390.

The system 350 can include a signal generator 370 and/or an amplifier 380. The signal generator 370 can generate one or more signals that drive the vibratory device 300 to vibrate to produce vibratory signals. The amplifier 380 can be operatively coupled to the signal generator 370 and can amplify the signals from the signal generator 370 prior to the signals being used to drive the vibratory device 300. The control unit 360 can control the operation of the signal generator 370 and/or the amplifier 380. A power source, not depicted, can be configured to supply power to one or more of the control unit 360, signal generator 370, amplifier 380, sensor 390, and/or other components of the system.

In some embodiments, the signal generator 370, the amplifier 380, and/or the sensor 390 can be integrated with and/or form part of the control unit 360. Alternatively, in other embodiments, the signal generator 370, the amplifier 380, and/or the sensor 390 can be separate from but operatively coupled to the control unit 360. In some embodiments, the vibratory device 300 can include one or more of the control unit 360, the signal generator 370, the amplifier 380, or the sensor 390.

In some embodiments, the control unit 360 is operable to store specialized instructions for controlling the vibratory device 300. Such instructions may be stored in memory 362 or in a separate memory. In addition, such instructions can be designed to integrate specialized functions and features into the controller to complete specific functions, methods and processes related to treating vestibular conditions disclosed herein. In some embodiments, the control unit 360 may be programmed with the instructions using a software development kit.

Electrical signals to control the vibratory device 300 may be generated by the control unit 360 based on the stored instructions. These electrical signals may be communicated between the control unit 360 and vibratory device 300 through wired or wireless (e.g., Bluetooth) methods. The electrical signals may include a stored pattern of operation, e.g., the stored instructions accessed by the controller may be used by the controller to generate a series of electrical signals that are sent to the vibratory device 300 to cause the vibratory device 300 to turn "on" or "off" in a pattern that is advantageous to a specific subject based on usage data that has been collected, accumulated, and stored for that user. One pattern may involve a series of vibratory signals where the number of vibratory signals generated and applied over a time period (e.g., per minute) to a subject may be varied, while a second pattern may include a series of vibratory signals where the force level in a number of vibratory signals may be varied. Other types of control signals, such as those that may be used to control the force level and frequency of vibratory signals generated by the vibrating device 300, may be sent to the vibrating device 300 from the control unit 360 based on data received from sensors (e.g., sensor 390 or other sensors). For example, an acceleration sensor may be included in a portable electronic device (e.g., mobile phone) to sense changes in a user's physical acceleration. In an embodiment, the control unit 360 may be operable to receive data from the acceleration sensor indicating a type of acceleration that may lead to motion sickness. Accordingly, after receiving such data, the control unit 360 may be operable to generate associated electrical signals and send such signals to the vibrating device 300. The vibrating device 300, in turn, may be operable to receive such electrical signals and generate vibratory signals that can be conducted via bone and applied to the vestibular system to, for example, pre-emptively account for motion sickness. The vibratory signals can cause a portion of the vestibular system to move in a manner equivalent to that of a therapeutically effective vibratory signal. For example, the vibratory signals can cause a portion of the vestibular system (e.g. the hair bundles forming the receptors in the semicircular canals and/or the otolith organs) to move in a random manner simulating a noisy vestibular signal or a noisy vestibular sensation or introduce some form of stochastic resonance within the vestibular system. In some instances, such noisy vestibular sensations can induce a reduction in the effects caused by other vestibular signals or a mismatch in signals perceived by a subject. Alternatively, a stored roadmap that represents a path or course that has previously resulted in a user becoming sick due to motion sickness may be stored in the control unit 360 or in the portable device along with a suitable positioning system such as, for example, Global Positioning System (GPS), Galileo, GLONASS, or Beidou. In some embodiments, as the positioning system indicates that the user is moving along the path or course and arrives at a position that may induce motion sickness, the control unit 360 may be operable to generate associated electrical signals and send such signals to the vibrating device 300. The vibrating device 300, in turn, may be operable to receive such electrical signals and generate vibratory signals that can be conducted via bone and applied to the vestibular system to, for example, pre-emptively account for motion sickness before the user reaches the position, for example.

In some embodiments, there may be wired and/or wireless communications between the vibratory device or bone conduction device and one or more sensors (e.g., wearable sensors), including, for example, rings, watches, patches, and bracelets. In some embodiments, there may be wired or wireless communications between the vibratory device and other connected devices, e.g., a mobile device (e.g., a cell phone, a tablet), a computer, or a smart home device.

The monitored biometric data, along with other data such as duration and frequency of use, preferred power settings, may be recorded either by the device or a connected device. The historic record of this data may be used to alter the devices settings for future uses. Data can also be shared with medical professionals to inform treatment. Individual devices can also be updated based on data received collectively from other devices which may provide insight into best settings for future uses.

Figure 4B:
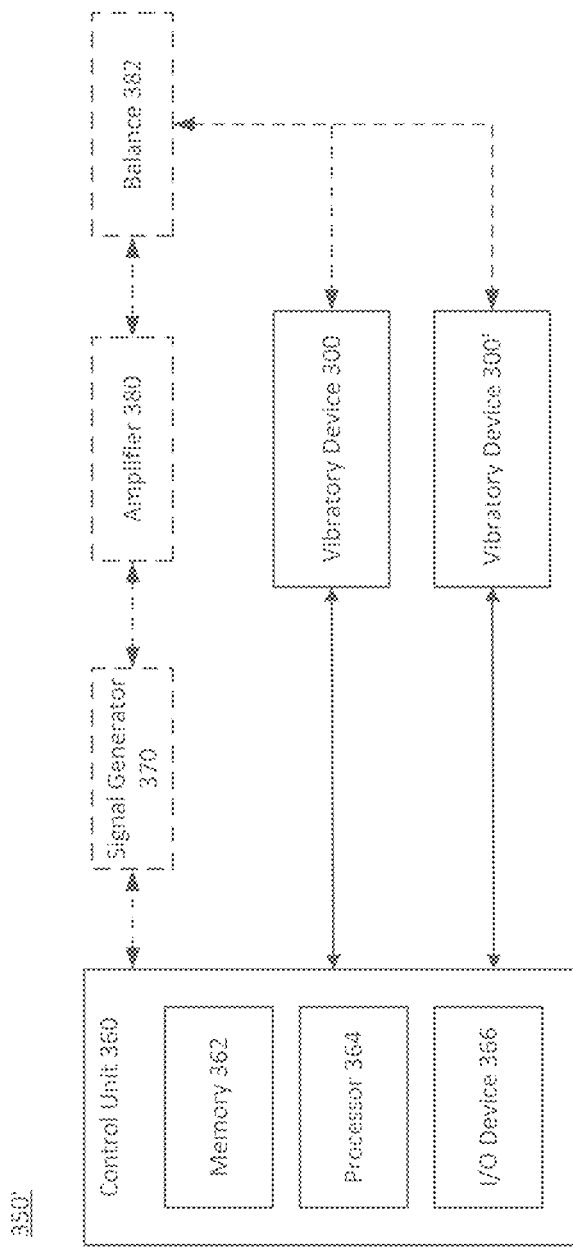
FIG. 4B is a schematic illustration of an example system for treating symptoms associated with vestibular conditions, according to another embodiment.

FIG. 4B schematically illustrates another example system 350' for treating vestibular conditions, according to an embodiment. The system 350' can be similar to the system 350, in that it includes a control unit 360 and a vibratory device 300 coupled to and energized and/or controlled by the control unit 360. Additionally, the system 350' can have a second vibratory device 300', also coupled to the control unit 360, whose activation can be controlled by the control unit 360. The control unit 360 can be configured to control the vibratory devices 300 and 300', such that vibratory signals generated by the vibratory devices 300 and 300' can be delivered simultaneously, alternatingly, and/or independently. While not depicted in FIG. 4B, similar to the system 300 depicted in FIG. 4A, system 350' can optionally include a signal generator (e.g., signal generator 370) coupled to the control unit 360, an amplifier (e.g., amplifier 380) coupled to the signal generator, and/or a sensor (e.g., sensor 390). In some embodiments, the two vibratory devices 300, and 300' can be coupled to a balance 382 that is configured to distribute signals generated by a signal generator and optionally amplified by an amplifier between the vibratory devices 300 and 300'. In some embodiments, the vibratory devices 300 and 300' can be coupled to each other and configured to send and/or receive signals from each other. While two vibratory devices 300 and 300' are depicted in FIG. 4B, one of ordinary skill in the art would appreciate that any number of vibratory devices can be used.

Figure 4C:
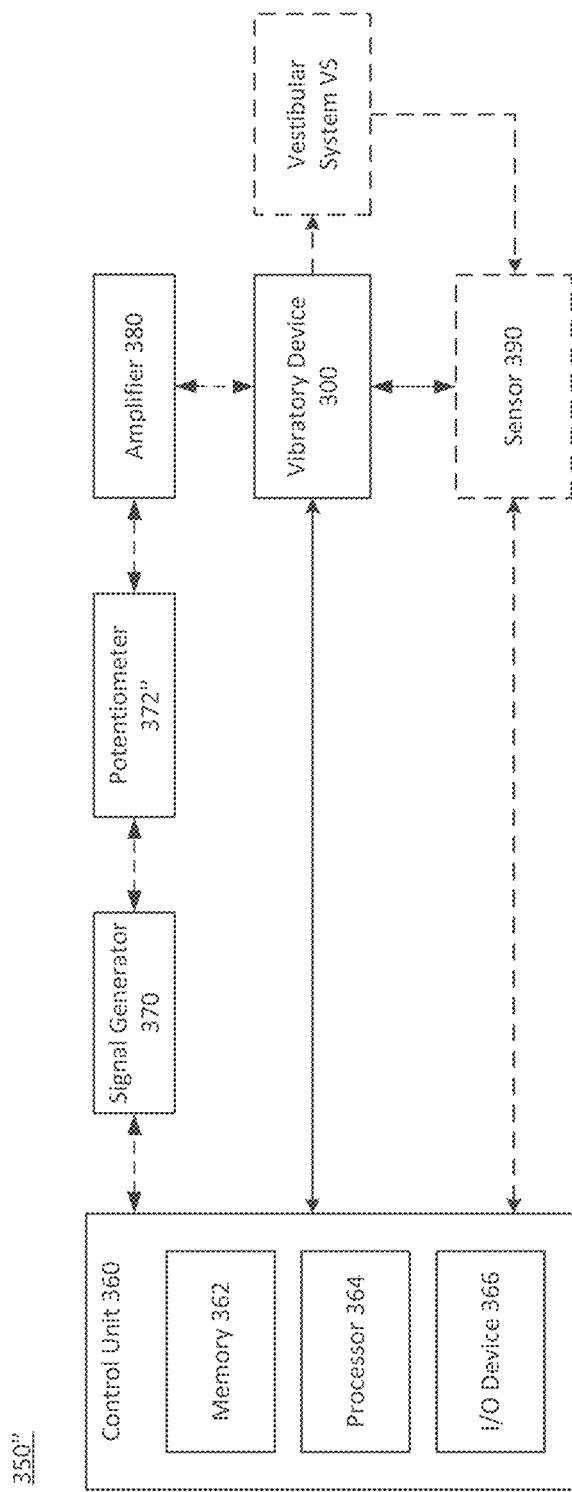
FIG. 4C is a schematic illustration of an example system for treating symptoms associated with vestibular conditions, according to another embodiment.

FIG. 4C schematically illustrates another example system 350" for treating vestibular conditions, according to an embodiment. The system 350" can be similar to systems 350, 350', in that it includes a control unit 360 and a vibratory device 300 (e.g., a transducer). The system 350" also includes a signal generator 370, a potentiometer 372", and an amplifier 380. The system 350" can optionally include one or more sensors 390, e.g., for measuring signals associated with the vibratory device 300, information associated with a surrounding environment, and/or physiological data associated with a user of the vibratory device, as further described below with respect to specific embodiments. The potentiometer 372" can be configured to measure an electric potential associated with signals being generated by the signal generator. The potentiometer 372" can be used the control the amplitude of the signals being sent to the vibratory device 300. Examples of suitable potentiometers include rotary potentiometers, linear potentiometers, rheostats, digital potentiometer, membrane potentiometer, etc. The potentiometer 372" can be used to ensure that any vibration generated by the vibratory device 300 does not exceed predefined, acceptable levels. A power source (not depicted) can be used to power one or more components of the system 350", e.g., signal generator 370, potentiometer 372", amplifier 380, and/or control unit 360.

While systems 350, 350', 350" are depicted as including components in addition to a vibratory device, it can be appreciated that such components (e.g., amplifier, sensor, potentiometer, signal generator, control unit, balance, etc.) can be integrated into or form a part of the vibratory device. For example, a printed circuit board (as further detailed with respect to embodiments below such as, for example, vibratory device 700) can include one or more of the signal generator, amplifier, potentiometer, balance, etc. and be mounted to and/or integrated into a vibratory device.

II. Vibratory Device

Figure 5:
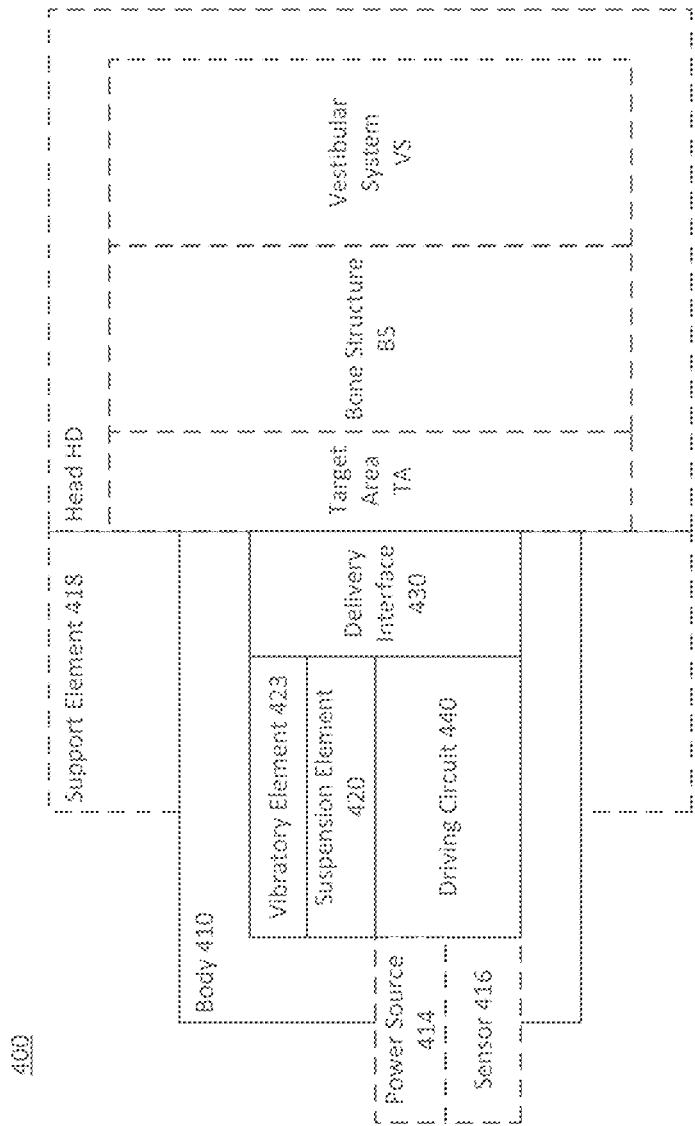
FIG. 5 is a schematic illustration of an example vibratory device of a system for treating symptoms associated with vestibular conditions, according to an embodiment.

FIG. 5 is a schematic illustration of an example vibratory device 400, according to an embodiment. The vibratory device 400 includes a body (or a housing) 410 that can define one or more chambers. The body 410 houses a vibratory element 423, a suspension element 420, a driving circuit 440, and a delivery interface 430. The vibratory element 423 is configured to be suspended by the suspension element 420 and driven by the driving circuit 440 to move (e.g. oscillate or vibrate) to produce the vibratory signal. The vibratory element 423 can be suspended within the body (e.g. in a chamber) such that the vibratory element 423 can vibrate about an equilibrium position. The movement of the vibratory element 423 can be with respect to the suspension element 420 and/or the body 410 of the vibratory device 400 to produce vibratory signals that can be directed via the delivery interface 430 to treat one or more vestibular conditions as disclosed herein. The vibratory device 400 and/or the body 410 of the vibratory device 400 can be positioned on a head of a subject with the delivery interface 430 on or against a target area TA such that the vibratory signals produced by the movement of the vibratory element 423 can be applied to the target area TA, which can then be conducted via a bone structure BS to a vestibular system VS of the subject.

Optionally, in some embodiments, the vibratory device 400 can include an onboard power source 414 to provide power to components of the vibratory device 400, and a sensor 416 to sense one or more signals from a portion of the vibratory device 400, the vestibular system VS, or another portion of the body (e.g., a portion of the body against which the generated vibratory signals are applied such as, for example, the target area TA or skin adjacent to and/or associated with the target area TA). In some embodiments, a remotely situated power source (e.g., a power source contained in control unit 360) can be used to power the vibratory device 400. In some embodiments, a remote sensor (e.g., a sensor 390) can be used to sense signals from a portion of the vibratory device 400, the vestibular system VS, or another portion of the body (e.g., a portion of the body against which the generated vibratory signals are applied).

The sensor 416 can be configured to measure and/or record information associated with the vibratory device 400 and/or the subject (e.g., the vestibular system VS, the target area TA, etc.). For example, the sensor 416 can include one or more suitable transducers to measure and/or record information from the vibratory device 400, including a current, a voltage (e.g., a voltage change associated with the electrical signal across the vibratory element 423), a magnetic field (e.g., a directional magnetic field generated by the electrical signal and applied near the vibratory element 423), or an acceleration of the vibratory element 423 during movement, etc.

In some embodiments, the sensor 416 can be used to increase an efficiency of the vibratory device 400. For example, the sensor 416 can include an ammeter for monitoring the current of an electrical signal coming from the vibratory element 423 and/or another portion of the vibratory device 400. A frequency of the electrical signal being supplied to the vibratory device 400 can be adjusted until a low current is measured by the ammeter, with the rationale that, at a resonant frequency of the vibratory device, the impedance of the vibratory device 400 is higher than at other frequencies and therefore the current lower than at other frequencies (assuming a constant voltage). Accordingly, the ammeter can be used to tune (e.g., adjust) the frequency of the electrical signal to the resonant frequency, such that the vibratory device 400 operates efficiently. That is, the vibratory device 400, in some embodiments, can include a processor configured to receive the information from the sensor 416 (e.g., information from the ammeter) and adjust the frequency of the electrical signal based on the information. For example, the processor can be configured to adjust the frequency of the electrical signal over time such that the vibratory device continues to operate at a reduce current and at a lowest resonant frequency.

As another example, the sensor 416 may include a voltage sensor or a voltmeter with a constant current amplifier. Voltage changes in the electrical signal supplied to a portion of the vibratory device 400 including the vibratory element 423 can be measured using the voltmeter. A frequency of the electrical signal being supplied to the vibratory device 400 (e.g. from a suitable signal source) can be adjusted until a high voltage is measured by the voltmeter, with the rationale that, at a resonant frequency of the vibratory device, the impedance of the vibratory device 400 is higher than at other frequencies and therefore the voltage higher than at other frequencies. Accordingly, the monitored voltage may be used to tune (e.g., adjust) the frequency of the electrical signal such that a high voltage is measured to achieve high efficiency.

As another example, where the vibratory element 423 is driven by a modulated magnetic field, the sensor 416 can include a Hall effect sensor that monitors magnetic field fluctuations. The magnetic field fluctuations can be measured, while a frequency of the electrical signal being used to generate the magnetic field is varied, to tune the frequency of the electrical signal to be at a resonant frequency of the vibratory device 400. As another example, the sensor 416 can include a movement sensor (e.g., an accelerometer) that can measure an acceleration and/or a velocity of the vibratory element 423 to determine when a resonant frequency is achieved.

The sensor 416 can also be equipped to receive and/or measure information from the subject such as movement associated with vibratory signals that are transferred to the bone structure of the subject, a temperature of the subject, an orientation or body position of the subject, etc.

The vibratory device 400 can also include a support element 418 to support or position the vibratory device 400 on or against the target area TA of the subject to deliver the vibratory signals, as disclosed herein. The support element 418 can be a device or fastening feature that can maintain contact and positioning of the vibratory device 400 with respect to the subject. For example, the support element 418 can be a head band, eye glasses, or a pillow, and so forth as disclosed in detail further below. In some embodiments, the support element 418 can be an adhesive component, such as, for example, an adhesive pad, a tacky polymer, etc. that can maintain contact and positioning of the vibratory device 400.

The power source 414, the sensor 416, and/or the support element 418 can be housed within and/or attached to the body 410 of the device 400.

The target area TA of the subject to which vibratory signals are applied may be, for example, a surface of the head. Optionally, in some embodiments, the vibratory device 423 may be implanted in the subject's head, and the target area TA can be a region that is proximate to and/or part of bone structure BS. The vibratory device can be configured to be engageable with the target area TA to effectively deliver therapeutic vibratory signals. In an example instance, the target area TA can be an area behind an external ear of a subject that overlays a mastoid process (or mastoid bone or mastoid process of the temporal bone) of a skull of the subject. In such instances, the mastoid bone may form part of the bone structure BS used to deliver vibratory signals to the vestibular system VS, via the bony structures of the inner ear housing the vestibular system VS. In some instances the zygomatic bone or the zygomatic process of the temporal bone can be a portion of the bone structure BS used to deliver vibratory signals to the vestibular system VS. In other instances, the target area TA can be a portion of a back of the head or the forehead, with the underlying regions of the skull acting as the bone structure BS that conducts the vibratory signals received from the vibratory device 400. Based on the target area TA selected and its distance from the vestibular system VS, varying force levels can be used to operate the vibratory device 400. For example, when the device is placed on a target area TA such as the forehead area of a subject or behind the head of a subject, regions that are further away from the vestibular system VS than the mastoid process, a higher force level may be used as compared to when the device is placed overlaying the mastoid process of the subject. As an example, when placed on the forehead or behind the head of a subject, the vibratory device 400 can be configured to apply vibratory signals with a force level up to 14 dB greater than the force level of vibratory signals that may be therapeutically effective when delivered elsewhere (e.g., region overlying the mastoid bone). When the target area TA is an area overlaying the mastoid bone and the vibratory device is placed overlaying that area, a therapeutically effective force level can be between about 87-101 dB re 1 dyne, and desirably, between about 90 and 100 dB re 1 dyne or between about 93-98 dB re 1 dyne, for treating a vestibular condition. Alternatively, when the vibratory device 400 is placed on a forehead or behind the head of the subject, the vibratory signals applied by the vibratory device 400 can have a therapeutically effective force level that ranges from about 101 dB to about 115 dB (i.e., 14 dB greater than the force level of the vibratory signals that are applied over the mastoid bone).

The body 410 of the vibratory device 400 can be configured to house various components of the vibratory device 400. In some embodiments, the body 410 can house some of the components while providing an interface for the coupling of one or more components that are not housed within the body 410, such as the power source 414, the sensor 416, and/or the support element 418. In some embodiments, the body 410 of the vibratory device 400 can define one or more chambers or receptacles for housing one or more components of the vibratory device such as the vibratory element 423, the suspension element 420, the driving circuit 440, and/or the delivery interface 430. The body 410 can also be shaped and/or configured for desired positioning of the delivery interface 430 against the target area TA of the subject's body (e.g., the body 410 can have a curved surface, or a surface that is malleable or flexible). In some embodiments, the body 410 and/or one or more of its chambers may be filled with air or in some instances a liquid such as a lubricant to aid in the generation and delivery of the vibratory signals. In some embodiments, the body 410 and/or one or more of its chambers may also include materials of having properties such as, for example, audible noise dampening agents such as sponges or sound absorbing materials, heat dissipation materials, etc.

The vibratory element 423 of the device 400 can be configured to oscillate or vibrate to generate the vibratory signal. In some embodiments, the vibratory element 423 can be housed within a chamber of the body 410. The vibratory element 423 can be suspended at an equilibrium position by the suspension element 420, and an electrical signal can be used to cause the vibratory element 423 to vibrate or oscillate about the equilibrium position to generate a vibratory signal. Properties of the vibratory element 423 and/or suspension element 420, such as the material, composition, structure etc., can be chosen to meet specific requirements of the generated vibratory signals (e.g., a low frequency signal).

For example, the vibratory element 423 can be a spring or an elastic material with a measure of stiffness (e.g., a spring constant) that enables generation of vibratory signals of a low frequency (e.g., a frequency of less than 200 Hz) with high efficiency. In an embodiment, the vibratory element 423 can be a mass that is suspended by a suspension element 420 that is a spring. The natural resonance of such a system can be determined based on Hooke's Law, as represented by the equation $$f = \frac{1}{2\pi}\sqrt{\frac{k}{m}},$$

where f is the resonant frequency, k is the spring constant, and m is the mass. The amplitude of movement of the mass is greater at the resonant frequency than at other frequencies, for a given power, since the mass and spring system at the resonant frequency can be associated with a purer tone (e.g., a sinusoidal waveform). Accordingly, operating the vibratory device 400 at its resonant frequency produces a stronger vibratory signal, and properties of the vibratory element 423 and/or suspension element 420 can be selected to achieve a particular resonant frequency.

Other factors that can affect and/or determine the generated vibratory signal can be, for example, the mechanism of the driving force (e.g., mechanical, magnetic), the ease of movement of the vibratory element (e.g., how frictionless is the movement), the location of the target area TA (e.g., the mastoid bone, the zygomatic bone, the skull near the forehead of a subject, etc.), reduced secondary or tertiary paths of energy dissipation (e.g., off-axis movement, heat, friction, etc.), direction of movement with respect to external forces (e.g., pressure during use, gravitational forces, etc.), requirements for ease of use by the subject under varied conditions (e.g., mobility of the subject, limitations on level of distractions, etc.), and so forth.

The vibratory element 423 can be configured such that it can be driven to generate vibratory movements along or about an axis of the vibratory device 400 (e.g., a longitudinal axis of the body 410), where the movements produce vibratory signals with suitable properties (e.g. frequency, amplitude, force level, etc.) for treating vestibular conditions. The vibratory device 400, in some embodiments, can be an electromechanical transducer including, for example, a vibratory element 423 implemented as a magnet that can be driven to move along an axis using a suitable driving force such as a magnetic field. Further details regarding such embodiments are described below with reference to FIGS. 6-9C.

Another method to produce a low frequency vibratory signal is to modulate an ultrasonic signal. In some embodiments, the vibratory device 400 can be a piezoelectric transducer driven by an electrical signal to generate vibrations in the ultrasonic frequency range. The vibrations of the piezoelectric transducer at this higher frequency can produce acoustic radiation pressure. The driving electrical signal can be clocked on and off at a lower frequency, less than 200 Hz (e.g., 60 Hz), such that the pressure from the piezoelectric transducer applied on and off at the lower frequency generates a corresponding vibratory signal at the lower frequency. The use of a piezoelectric transducer can reduce a size and weight of the vibratory device 400, as piezoelectric transducers are typically smaller and lighter than other types of electro-mechanical transducers.

Depending on where the vibratory device 400 is placed, the dimensional restrictions of the vibratory device 400, and/or the configuration or shape of the vibratory device 400, specific components of the vibratory device 400 can be selected to provide a therapeutically effective level of vibratory signal to treat a vestibular condition. While one vibratory element 423 is illustrated in FIG. 5, one of ordinary skill in the art would appreciate that vibratory device 400 can include one or more additional vibratory elements, which can work together and/or independently to generate vibratory signals to treat a vestibular condition.

Similar to other vibratory devices or systems, the vibratory device 400 can be associated with a set of resonant frequencies. In some embodiments, the vibratory element 423 may be configured to move in response to a driving force such that the amount of power of the generated vibratory signals at a lowest resonant frequency associated with the vibratory device 400 is greater than the amount of power of the vibratory signals at the remaining resonant frequencies (e.g., higher resonant frequencies) associated with the vibratory device 400. For example, a vibratory device may be configured to have a lowest resonant frequency between about 10 Hz and about 200 Hz, about 10 Hz and about 150 Hz, about 10 Hz and about 100 Hz, about 10 Hz and about 80 Hz, about 30 Hz and about 80 Hz, or about 50 and about 70 Hz, and inclusive of other values and subranges in between. In some embodiments, the vibratory signals generated at the lowest resonant frequency in these ranges can be of greater amount of power than vibratory signals that may be generated at other resonant frequencies. In some embodiments, the vibratory element 423, the suspension element 420, and/or other elements of the vibratory device 400 can be selected such that the vibratory device 400 vibrates at a lowest fundamental frequency of less than 200 Hz.

In some embodiments, the vibratory element 423 can vibrate at a first resonant frequency along a first axis (e.g., an axis in a z-direction) and also vibrate at a second resonant frequency along secondary axes (e.g., an axis in a x-y plane). To reduce the vibrations along the secondary axes, the vibratory element 423, the suspension element 420, and/or other elements of the vibratory device 400 can be selected such that the first resonant frequency is not a harmonic of the second resonant frequency, and vice versa (e.g., the first resonant frequency is a few hertz offset from the second resonant frequency and/or a harmonic of the second resonant frequency), such that vibrations along the secondary axes can be reduced when the vibratory device 400 is stimulated at the first resonant frequency. Vibrations along the secondary axes can, for example, lead to internal collision between components of the vibratory device 400 and/or audible sound.

Figure 16:
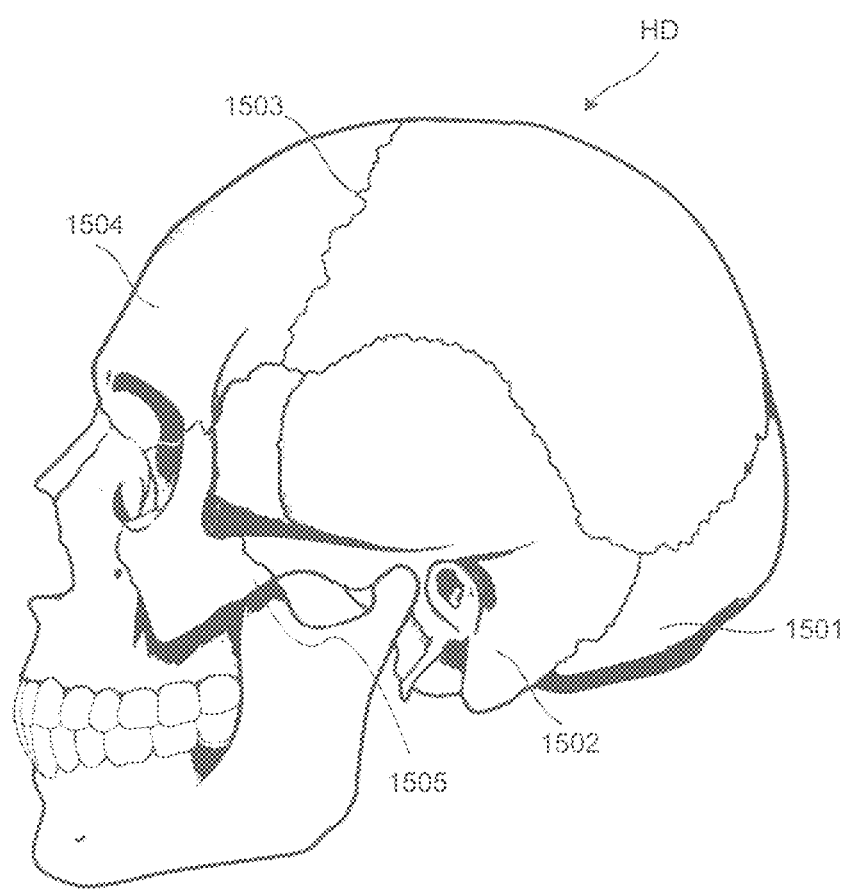
FIG. 16 is a schematic illustration of a human skull, indicating example locations for the placement of a vibratory device in a system for treating symptoms associated with vestibular conditions, according to various embodiments.

The vibratory device 400 can be positioned in different areas on a head of a subject. FIG. 16 depicts a human skull and indicates some example regions of the skull where the vibratory device 400 may be positioned, to apply therapeutic vibratory signals to treat vestibular conditions disclosed herein. For example, as indicated in FIG. 16, the vibratory device 400 can, in some instances, be placed over a mastoid bone 1502 of the subject's skull. While a left mastoid bone 1502 is identified in FIG. 16, one of ordinary skill in the art would appreciate that the vibratory device 400 can be placed over a left or right mastoid bone of a subject. In other instances, the vibratory device 400 can be placed over a portion of the back of the head (e.g. over a left, right, or central portion of an occipital bone 1501) or over a portion of the forehead (e.g. a left, right or central portion of a frontal bone 1504) to deliver vibratory signals to treat vestibular and other conditions disclosed herein. Depending upon the region that the vibratory device 400 is placed (e.g., its proximity to the vestibular system, whether vibrations from the device need to traverse a suture line 1503), a force level of the vibratory signals may be adjusted such that a therapeutically effective level of vibration for treating a condition is delivered to the vestibular system.

When the vibratory device 400 is positioned overlaying a mastoid bone (e.g. mastoid bone 1502 shown in FIG. 16), the vibratory device 400 can apply a vibratory signal that is therapeutically effective at treating a condition of the vestibular system (i.e., a therapeutically effective vibratory signal) having a resonant frequency of less than 200 Hz (e.g., about 10 Hz, about 30 Hz, about 50 Hz, about 70 Hz, about 100 Hz, about 150 Hz, and all values and subranges in between) and a force level between 87 and 101 dB re 1 dyne (or between about 90 and 100 dB re 1 dyne). If the vibratory device 400 is positioned overlaying a different area of the subject's head that is further from the subject's vestibular system than the mastoid bone, (e.g., a zygomatic bone 1505, or a frontal bone 1504 or an occipital bone 1501, shown in FIG. 16), then the vibratory device 400 can generate a vibratory signal that has a greater force level such that the vibratory signal can affect a portion of the vestibular system in a manner equivalent to a therapeutically effective vibratory signal that is applied to an area overlaying the mastoid bone (e.g., 1502 shown in FIG. 16). For example, when the vibratory device 400 is positioned over a frontal bone of a subject (e.g., frontal bone 1504 in FIG. 16), the vibratory device 400 can generate a vibratory signal having a force level that is greater than the force level of a therapeutically effective vibratory signal that is applied to an area overlaying the mastoid bone (e.g., up to 14 dB re 1 dyne greater).

In the embodiments described herein, the force level represents a unit of "loudness" for bone conduction, and can increase with increasing amplitude of vibration, frequency of vibration, and mass of the system (e.g., vibratory device). The force level in combination with frequency produces impulses (changes in momentum) that are capable of stimulating the vestibular system in a therapeutically effective manner. Momentum is directly proportional to force and inversely proportional to frequency. Therefore, with high frequencies, e.g., above 200 Hz, the force required to produce impulses that are sufficient to stimulate the vestibular system must increase as well. Conventional bone conduction devices (e.g., bone conduction speakers) are designed to produce vibrations with frequencies about 250 Hz, and accordingly, to be able to produce therapeutically effective vibrations, such devices must produce vibrations with high force levels that can be undesirably loud. Most conventional bone conductions systems are incapable of reaching such high force levels without burning out first. With systems and devices described herein, the frequencies applied by the vibratory devices (e.g., bone conduction devices) are low (e.g., less than 200 Hz) and therefore can be capable of generating therapeutically effective vibrations. Systems and devices described herein avoid producing perceptible levels of audible sound and/or tapping sensations, both of which can be undesirable and distracting to users.

The suspension element 420 of the vibratory device 400 can include one or more components that are housed in the body 410, and that interact with the vibratory element 423. In some embodiments, the suspension element 420 and/or the vibratory element 423 can be configured with adaptations to accommodate each other. For example, the suspension element 420 can include components that can extend through openings defined in the vibratory element 423.

In some embodiments, the suspension element 420 can be housed within a chamber of the body 410, and in some instances, can be disposed in a fluid such as a lubricant. The suspension element 420 can be configured to apply a force on the vibratory element 423 to suspend, hold or support the vibratory element 423 in a position of equilibrium until driven to move by the application of a driving signal. For example, the suspension element 420 can be a spring coupled to a vibratory element 423 (e.g. a magnet). Alternatively or additionally, the suspension element 420 can include a pair of magnets in an arrangement with the vibratory element 423 (e.g., another magnet) to each apply a force on the vibratory element 423 in an opposing direction (e.g., opposing or repulsive magnetic forces) to collectively hold the vibratory element 423 in an equilibrium position by virtue of forces acting between them (e.g. the opposing or repulsive magnetic forces). In such embodiments, a driving force (e.g. an applied magnetic field of a specific magnitude and acting along specific directions) can induce the vibratory element 423 (e.g. the magnet in equilibrium position) to move between the pair of magnets. In other embodiments, the suspension element 420 can be an elastic material or fluid. While one suspension element 420 is depicted in FIG. 5, one of ordinary skill in the art would understand that a plurality of suspension elements 420 can be used to support and/or suspend the vibratory element 423. The plurality of suspension elements 420 can include one or more different types of suspension elements (e.g., a magnet, a spring, an elastic material, etc.).

The driving circuit 440 of the vibratory device 400 can include one or more suitable components that can generate an electrical signal. The electrical signal can cause a force to be generated to induce movement of the vibratory element 423 along an axis to produce therapeutic vibratory signals. The driving circuit 440, in some embodiments, can receive the electrical signal from a control unit (such as the control unit 360 in FIGS. 4A and 4B). In some other embodiments, the driving circuit 440 can itself include an onboard unit that can generate the electrical signal.

The electrical signal generated or received by the driving circuit 440 and used to induce movement of the vibratory element 423 can be of suitable properties to produce a vibratory signal having specific frequency and force levels. For example, the electrical signal can be selected such that it causes the vibratory element 423 to produce vibratory signals that have a particular range of frequencies (e.g., less than 200 Hz) to treat one or more specific vestibular conditions. In some embodiments, a control unit (e.g., control unit 360) can be capable of changing a frequency of the electrical signal until the electrical signal causes the vibratory device 400 to vibrate at a resonant frequency, such as described above with sensor 416.

In some embodiments, the driving circuit 440 can include an onboard signal generator to generate the electrical signal, an amplifier to amplify the signal, and one or more elements for converting the electrical signal into the appropriate modality that causes the vibratory element 423 to move. For example, the driving circuit 440 can include one or more coils that can generate a magnetic field that moves the vibratory element 423.

The delivery interface 430 of the vibratory device 400 can be configured to transfer the vibratory signals generated by the vibratory element 423 to the target area TA of the subject, such that the vibratory signals can be conducted via the bone structure BS beneath to the vestibular system VS. The delivery interface 430 can be configured for and/or adaptable to the structure and/or shape of the target area TA of the user such that the delivery interface can engage with and/or maintain contact during the period of use for transfer of the therapeutic vibratory signals. In some embodiments, the delivery interface 430 can be configured with considerations of comfort and ease of use for the user, for example, during use of the vibratory device 400 to mitigate a vestibular conditions. The delivery interface 430 may further be configured to reduce secondary effects that may be undesirable such as the generation and accumulation of heat, generation of audible noise, lack of air circulation, application of pressure against the target area TA, etc. For example, the delivery interface 430 can include a layer of memory foam material that may aid in adapting to the contours of the target area (e.g., a region behind the ear overlying the mastoid process). The memory foam material may also aid in heat dissipation, dampening of audible noise, encourage air circulation, minimize discomfort from pressure applied by a support element such as a head band, etc.

Figure 6:
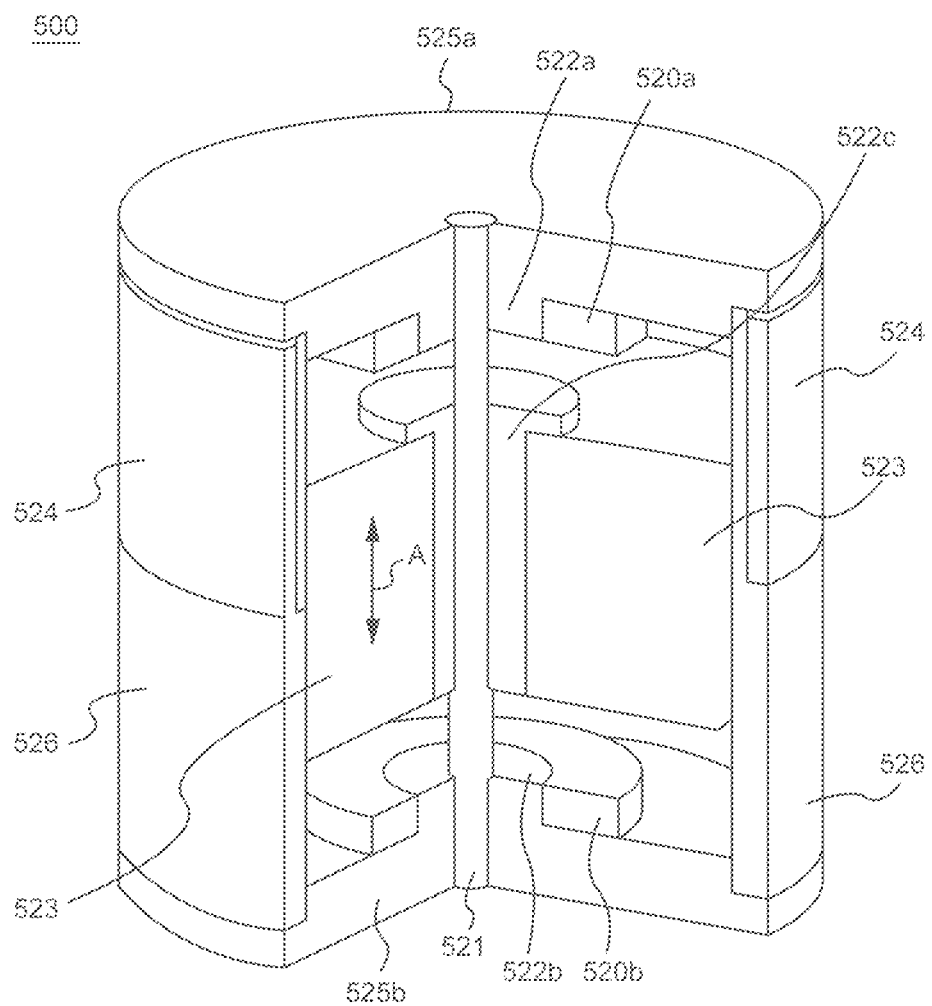
FIG. 6 is a schematic illustration of a cut-away view of an example vibratory device of a system for treating symptoms associated with vestibular conditions, according to another embodiment.

FIG. 6 is an illustration of an example vibratory device 500 according to one embodiment. The vibratory device 500 includes a body (or housing) 510 that includes a tubing 526 and end caps 525a, 525b. In some embodiments, the body 510 of the vibratory device 500 can define a chamber. The body 510 houses a vibratory element implemented as a magnet 523 and suspension elements implemented as magnets 520a, 520b. As shown in the cut-away view in FIG. 6, the suspension elements include magnets 520a, 520b, and the vibratory element 523 includes a magnet 523. The magnets 520, 520b act as suspension elements by exerting opposing forces on the magnet 523 to suspend the magnet 523 at an equilibrium position, as shown in FIG. 6. For example the magnet 520a can be configured to apply a force on the first magnet 523 in a first direction and the magnet 520b can be configured to apply a force (e.g. a force equivalent in magnitude to that exerted by the second magnet 520a on magnet 523) on the first magnet 523 in a second direction (e.g. a second directions 180° removed from the first direction). As such the first magnet 523 can be disposed between the second magnet 520a and the third magnet 520b in the body 510 (e.g. a chamber) such that the second magnet 520a and the third magnet 520b collectively suspend the first magnet 523 at a position (e.g. an equilibrium position) within the body 510.

The magnet 523 acts as the vibratory element configured to move (e.g., oscillate or vibrate) to produce the vibratory signal. The vibratory element 523 can be collectively suspended by the suspension elements 520 a, 525b within the body 510 (e.g., in a chamber) such that the vibratory element 523 can vibrate about an equilibrium position.

In some embodiments, the vibratory device 500 can include an elongate member having a longitudinal axis. The elongate member can be configured to extend through an opening in the vibratory element 523 such that the vibratory element 523 can be configured to vibrate along the longitudinal axis of the elongate member. The elongate member can further be configured to reduce oscillations or vibrations of the vibratory element 523 along any axis other than the longitudinal axis. As shown in FIG. 6, the vibratory device 500 further includes an elongate member in the form of a pin 521 that can be secured to the end caps 525a, 525b. The pin 521 passes through openings 522a, 522b defined in the end caps 525a, 525b of the vibratory device 500, openings defined in the magnets 520a, 520b, and an opening defined in the magnet 523. The pin 521 provides an axis for movement of the magnet 523 (e.g., along a longitudinal axis of the pin 521). The vibratory device 500 further includes a driving circuit that includes a coil 524 configured to generate a magnetic field capable of driving the vibratory device using an electrical signal. The vibratory device 500 includes a bushing 522c configured to fit in the opening defined in the magnet 523, and configured to interface between the pin 521 and the magnet 523 allowing smooth movement of the magnet 523 over the pin 521.

In operation, the vibratory device 500 is driven using an electrical signal that comprises a sine wave or another type of signal waveform at a low frequency (e.g., less than 200 Hz). The coil 524 is operable to generate a magnetic field with an induced electrical current. The magnetic field in turn applies a magnetic force on magnet 523. The magnetic force, when applied to the magnet 523, causes the magnet 523 to move along the axis indicated by the arrow "A" in FIG. 6.

The magnet 523 is configured to move in either of the directions indicated depending on the direction of the magnetic field vector.

Magnets 520a and 520b, forming the suspension element, each create a constant magnetic field, each of which is applied to magnet 523 (i.e., a north side of magnet 520a will face a north side of magnet 523 and a south side of magnet 520b will face a south side of magnet 523). Accordingly, the magnets 520a, 520b apply opposing forces on the magnet 523. The opposing forces created by magnets 520a, 520b are operable to suspend the magnet 523 at the equilibrium position such that the magnet 523 oscillates about the equilibrium position and generates the one or more vibratory signal signals. The electrical signal will cause the magnet 523 to oscillate or move along the axis A, which can be the same as or may substantially correspond with a longitudinal axis of the pin 521.

In some embodiments, to ensure that the magnets 520a, 520b and 523 do not oscillate or move in a direction other than along the axis A, which may affect the efficiency of the system and increase undesirable friction that causes secondary vibratory signals (e.g., a humming sound), the vibratory device 500 can be configured such that the motion of magnet 523 is restricted by the pin 521. In some embodiments, each of the magnets 520a, 520b, can be secured to the end caps 525a, 525b of the vibratory device 500 with a glue, epoxy, or another form of adhesive. The magnet 523 can be fitted around the pin 526 with the bushing 522c interface allowing the magnet 523 to smoothly move over the pin 521 while restricting any motion that is not along the axis A. Glue, epoxy, or any other form of adhesive may also be used to secure the pin 521 to the end caps 525a, 525b through openings or holes 522a, 522b.

In some embodiments, the tubing 526 may contain and/or include on its inner surface a lubricant (e.g., ferrofluid) or a low friction material (e.g., polytetrafluoroethylene), configured to reduce the potential friction between the magnet 523 and the inner surface of the tubing 526. Reduced friction can be configured to ensure a quieter operation of the vibratory device 500 (e.g., with less noise generated by the potential friction from contact). Such lubricants may also be used to reduce the friction between the bushing 522c and the pin 521.

In some embodiments, the outer surface of the tubing 526 and/or endcaps 525a, 525b can be covered with a sound absorbing material. Further, in some embodiments, one or more of the endcaps 525a, 525b can be covered with a friction reducing material (e.g., a smooth material) or an impact absorbing or padded material, such as, for example, cork, so that when that endcap comes into contact with a person's skin or body the contact is less abrasive than if the endcaps 525a, 525b where not covered by such material. Further, in some embodiments, one or more of the endcaps 525a, 525b may be attached to a structure that increases a surface area of that endcap, so that when that endcap comes into contact with a person's skin or body, the contact is spread over a larger area reducing the pressure exerted by that endcap on the skin or body.

It should be understood that the magnets 520a, 520b are one example of elastic objects that can be used to form the suspension element in the vibratory device 500. In other embodiments, the magnets 520a, 520b may be replaced by other elastic objects (e.g., springs, an elastic polymer).

Figure 7A:
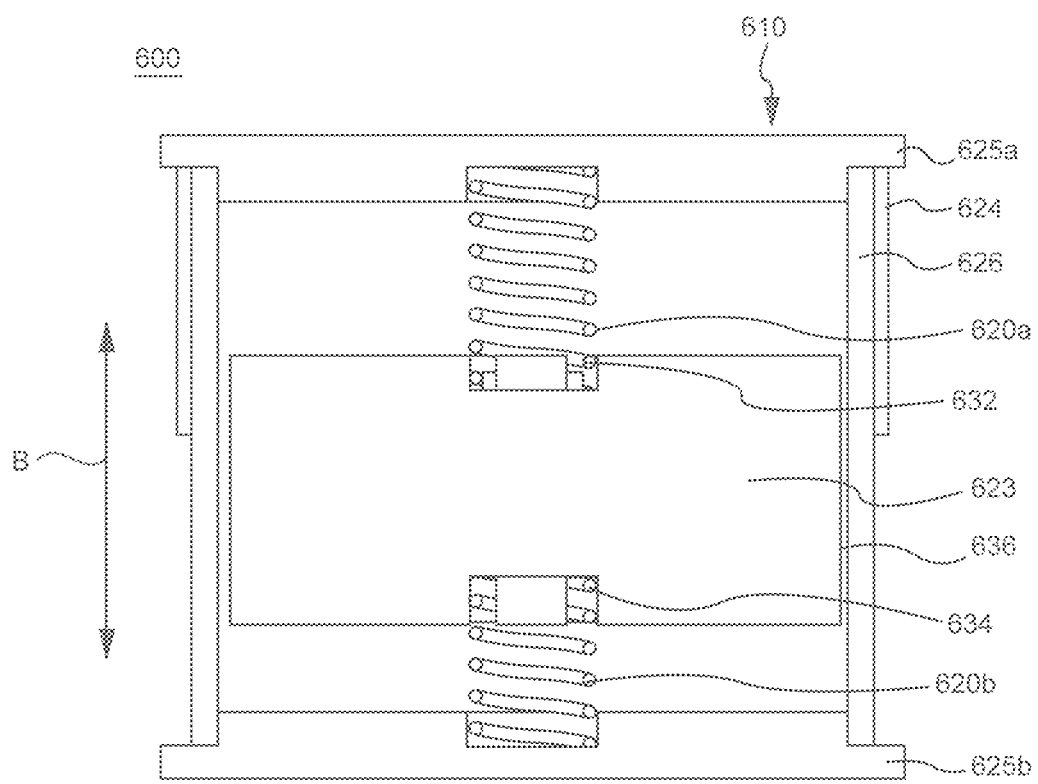
FIG. 7A is a schematic illustration of a cross-sectional view of a vibratory device in a system for treating symptoms associated with vestibular conditions, according to an embodiment.

FIG. 7A illustrates an embodiment of the vibratory device 600 that includes springs as suspension elements. The vibratory device 600 can be similar to the vibratory device 500 depicted in FIG. 6 described above. For example, the vibratory device 600 can include a housing 610 including a tubing 626 (e.g. a Nylon tubing) and end caps 625a, 625b. The vibratory device 600 can further include a magnet 623 forming the vibratory element, and a driving circuit including a coil 624 to drive movement of the magnet 623 to produce the vibratory signals used to treat vestibular conditions disclosed herein.

As shown in the cross-sectional schematic in FIG. 7A, the vibratory device 600 can include suspension elements implemented as springs 620a, 620b, instead of the magnets 520a, 520b in the vibratory device 500 shown in FIG. 6. The magnet 623 can be collectively suspended by the springs 620a, 620b, within the housing 610 (e.g. in a chamber) such that the magnet 623 can vibrate about an equilibrium position when energized by an electrical signal.

As described above with reference to the vibratory device 500, in some embodiments, the vibratory device 600 can include an elongate member having a longitudinal axis. The elongate member can be configured to extend through an opening in the vibratory element magnet 623 such that the magnet 623 can be configured to vibrate along the longitudinal axis of the elongate member. The elongate member can further be configured to reduce oscillations or vibrations of the magnet 623 along any axis other than the longitudinal axis.

The springs 620a, 620b, may be supported by the elongate member, cavities in end caps 625a, 625b and/or other suitable structure(s) extending from the end caps (not shown in FIG. 7A) such as, for example, a rigid and/or flexible structure (e.g., a pin, foam, rubber, or any another material). The springs 620a, 620b, can be configured to expand and compress along an axis (e.g. a longitudinal axis) and the magnet 623 mounted to the springs 620a, 620b, configured to oscillate or vibrate along the same axis to produce therapeutic vibratory signals. The springs, used as the elastic objects forming the suspension element, can be secured to other parts of the vibratory device 600 (e.g., to the magnet 623, tubing 626, and/or end caps 625a, 625b) using a glue, epoxy, or any form of adhesive. The springs 620a, 620b, can be configured to reduce oscillations of the magnet along any axis other than the axis (e.g. longitudinal axis) of the springs.

The springs 620a, 620b can be of any suitable material (e.g., stainless steel), and be chosen to have certain stiffness, for spring constant k, such that they allow movement of the magnet 623 along an axis indicated by the labeled arrow "B," when driven by an electrical signal. The springs 620a, 620b can be configured such that they are attached to the magnet 623 and a portion of the housing 610. For example, each spring (620a and 620b) can have a first end that may be attached to a portion of the housing 610 and a second end attached to the magnet 623. As such, the springs can be configured to apply a force on the magnet to suspend the magnet at the position within the chamber. For example, the springs 620a and 620b can each exert an equivalent force in an opposite direction such that with movement of the magnet 623, as one spring (e.g. 620a) expands the other spring (e.g. 620b) may contract and vice versa, such that the magnet 623 may oscillate or vibrate along an axis (e.g. the longitudinal axis of the springs) the movement of the magnet 623 may be configured to be about the position of suspension (e.g. an equilibrium position). The vibratory device 600 can include one or more glue pockets 632, 634 as points of coupling between the springs 620a, 620b and the magnet 623, respectively.

In some embodiments, the springs 620a, 620b are operable to prevent contact between the magnet 623 and the inner surface of the tubing 626. As described above with reference to the vibratory device 500, the tubing 626 of the vibratory device 600 can contain and/or include on the inner surface a lubricant (e.g., ferrofluid) or a low friction material (e.g., polytetrafluoroethylene), to reduce potential friction from any contact between the magnet 623 and the inner surface of the tubing 626 during movement of the magnet 623. In some embodiments, a rod or pin (not shown in FIG. 7A) and a bushing (not shown in FIG. 7A) may be included to further limit a movement of the magnet 623 in directions other than along axis B.

Figure 7B:
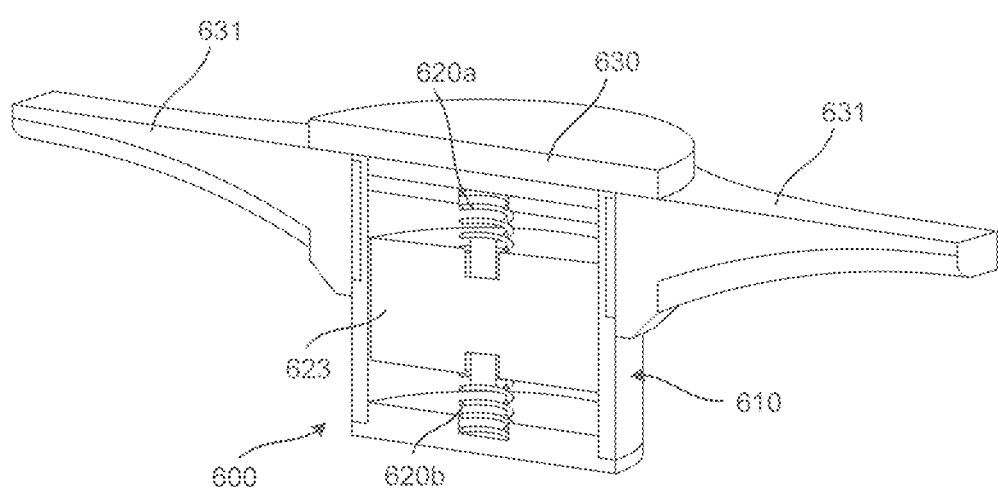
FIG. 7B is a schematic illustration of a cross-sectional view of the vibratory device in FIG. 7A integrated into a physical platform for placement on a subject, according to an embodiment.

FIG. 7B illustrates a cross sectional view of the vibratory device 600 from FIG. 7A, attached to a delivery interface 630 for delivering the therapeutic vibratory signals. As described before the magnet 623 acts as the vibratory element suspended by the springs 620a, 620b. The delivery interface 630 can be a memory foam pad configured to transfer vibratory signals from the vibratory device 600 to the body of the subject. While magnets and springs have been provided as examples of suspension elements, one of ordinary skill in the art would understand that other types of elastic objects may be used in lieu of and/or in addition to magnets and/or springs.

The vibratory devices disclosed herein (e.g., vibratory devices 400, 500, 600, 700) can have high Q factors (e.g., be capable or oscillating with greater amplitudes at a narrow range of frequencies). In some embodiments, a vibratory device can be operable at a lowest, fundamental frequency, such as a frequency between 50-70 Hz, with a low amount of power being directed to upper and more audible resonant frequencies.

Figure 8:
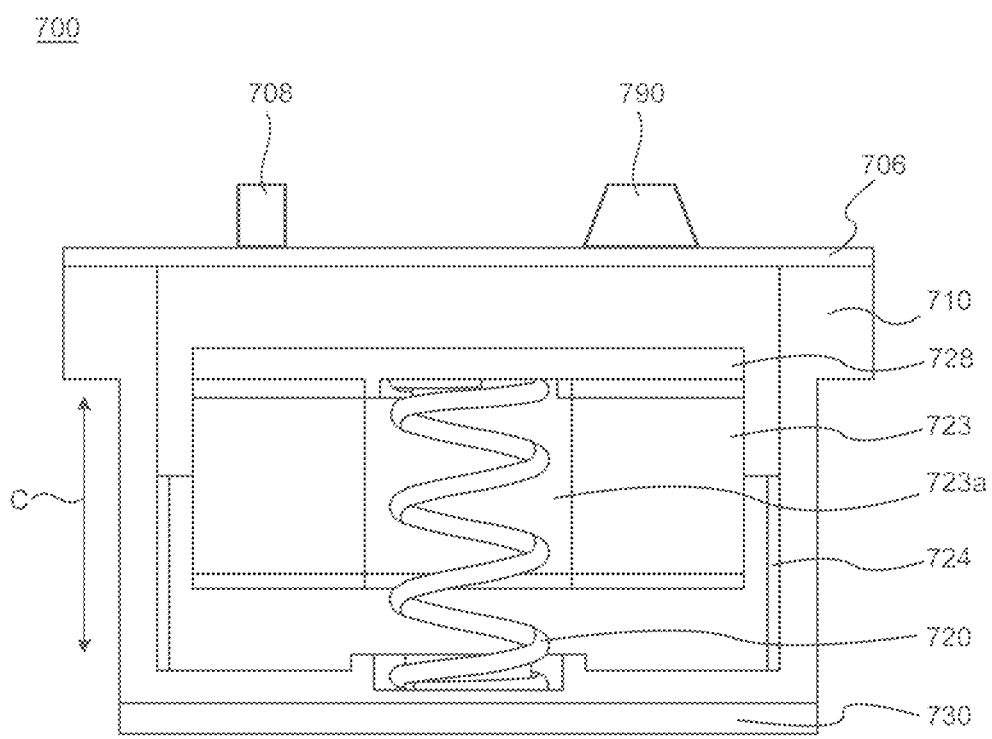
FIG. 8 is a schematic illustration of a cross-sectional view of a vibratory device in a system for treating symptoms associated with vestibular conditions, according to another embodiment.

FIG. 8 illustrates a cross-sectional view of a vibratory device 700 according to an embodiment. The vibratory device 700 can be similar to the vibratory devices 500, 600. For example, the vibratory device 700 can include a housing 710, a vibratory element implemented as a magnet 723, a suspension element implemented as a spring 720, and a driving circuit including a coil 724 to drive movement of the magnet 723 to produce the vibratory signals used to treat vestibular conditions disclosed here. The magnet 723 can be suspended by the spring 720, within the housing 710 (e.g. in a chamber) such that the magnet 723 can vibrate about an equilibrium position when energized by an electrical signal delivered by the driving circuit.

In some embodiments, to reduce the spring constant of the spring 720, thereby affecting the resonant frequency of the vibratory device 700, a length of the spring 720 can be increased, which can allow for the generation of lower frequencies. In order to change the length of the spring without altering the size of the vibratory device 700, the spring 720 can be configured to pass through an opening 723a defined by the magnet 723. As shown in FIG. 8, the spring 720 can be attached to a mounting plate 728 and adhered to the far side of the magnet 723 rather than be attached to the near side of the magnet 723. In this way, a length of the vibratory device 700 can remain the same while a length of the spring 720 can increase by a length equal to or substantially equal to the thickness of the magnet 723. In some embodiments, as an alternative to having a mounting plate 728, the magnet 723 can have an opening that extends through a portion of its length (e.g., approximately 95% of its length), and the spring 720 can extend through the opening and attach to the far end of the magnet 723, similar to how the spring 720 would attach to a mounting plate 728.

Similar to the vibratory device 600 as depicted in FIG. 7B, the vibratory device 700 illustrated in FIG. 8 can also be attached to a delivery interface (e.g., a delivery interface 730) to deliver vibratory signals to a subject's vestibular system. The delivery interface 730 can include a padded material, such as a memory foam pad, to conform to a surface of a target area and act as an interface between the vibratory device 700 and the target area, to effectively deliver the vibratory signals.

As shown in FIG. 8, some embodiments of the vibratory device can include an integrated circuit 706 that includes circuitry for generating a signal for activating the vibratory device 700. The integrated circuit 706 can include one or more leads or connection points 708 (e.g. wire leads) to connect to other components (e.g. a control unit 360 such as a microcontroller). The integrated circuit 706 can also include and/or be coupled to a sensor 790.

The vibratory device 700 can have a high Q factor. In operation, a frequency of a signal being used to activate the vibratory device 700 may be selected such that the vibratory device 700 operates at a resonant frequency to increase an amplitude of the oscillations for a given power input. In an embodiment, the sensor 790 can include a Hall effect sensor that is configured to monitor magnetic field fluctuations. When the frequency of the electrical signal supplied to the vibratory device 700 from a signal source that can vary force level and/or frequency (e.g., signal generator 370 and/or amplifier 380) matches a resonant frequency of the vibratory device 700, the magnet 723 can move further (e.g., oscillate or vibrate with greater amplitude) than at other frequencies. Accordingly, magnetic field fluctuations caused by the oscillations of the magnet 723 can increase when the frequency of the electrical signal matches a resonant frequency of the vibrating device 700. This relative fluctuation can be monitored using a Hall effect sensor.

In more detail, a microcontroller or microprocessor (e.g., a control unit 360) may be operable to receive signals from the Hall effect sensor and adjust a frequency of the electrical signal used to power the vibratory device 700 based on the sensor readings. For example, the microcontroller may be operable to scan through a set range of frequencies (e.g., 50-65 Hz) and select a frequency of the electrical signal that generates the highest level of magnetic field fluctuations. This process may be referred to as "tuning." Thereafter, the combination of the sensor 790 and microcontroller may continue to tune the frequency of the electrical signal supplied to the vibratory device 700 to maintain that efficiency each time the device is turned on. In addition, after a frequency of the electrical signal has been selected, the frequency may be modified around the selected frequency to determine whether the frequency of the electrical signal associated with peak efficiency changes over time due to temperature, wear, or other variables that may cause the properties of components of the vibratory device 700 (e.g., the spring 720) to change with time.

In some embodiments, the sensor 790 can include an ammeter, a voltmeter, an accelerometer, or some other type of sensor, similar to the sensor 390, for measuring information (e.g., current, voltage, acceleration, etc.) to be able to select the resonant frequency that provides greatest efficiency.

Integrated circuit 706 can function as an endcap, which further reduces the size of vibratory device 700. The delivery interface 730 may be, for example, a foam pad operable to function as structure that conforms to the surface of a user's skin and is capable of transferring vibratory signals from the vibratory device 700 to the body, such that it can be conducted via bone to the vestibular system. The delivery interface 730 may be configured such that a good coupling allows an efficient transfer of vibratory signals to the head.

In some embodiments, to avoid audible tones (i.e., noise, humming), the vibratory device 700 may be configured to reduce friction and/or contact between internal structures. For example, the magnet 723, coil 724, housing 710, etc. may be positioned with sufficient tolerances between one another to allow natural rocking and swaying of components while reducing contact between the various components.

Similar to the magnet 623 of the vibratory device 600, the magnet 723 may also wobble in directions not along the axis C, which may cause the magnet 723 to contact an inner surface of the vibratory device 700. This contact can make an audible sound and/or reduce an efficiency of the vibratory device 700. In some such embodiments, noise may be minimized by choosing a spring 720 and magnet 723 whose properties cause the axial resonant frequency to not be the same as the wobbling resonant frequency or any of its harmonics. Then, in operating the vibratory device 700 at a frequency that corresponds to the axial resonant frequency and not the wobbling resonant frequency can reduce wobbling and unintentional contact between the magnet 723 and other components of the vibratory device 700.

To adjust the output force level of the mechanical vibratory signals output by the vibratory device 700, the voltage of the electrical signal input into the vibratory device 700 may be increased. Alternatively or additionally, to adjust the output force level of vibratory signals, the frequency of the electrical signal may be adjusted to the resonant frequency.

Figure 9B:
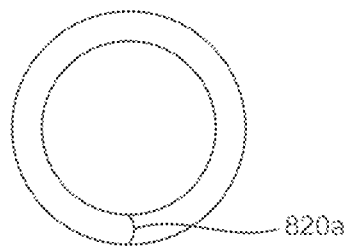
FIGS. 9B and 9C are illustrations of a top view and a bottom view, respectively, of the spring in FIG. 9A.
Figure 9A:
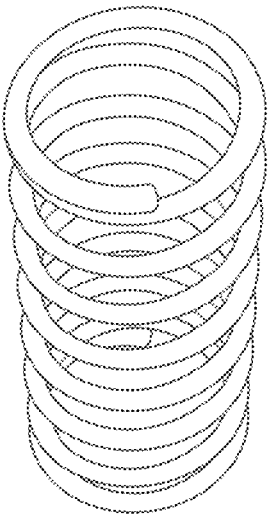
FIG. 9A is a perspective view of a spring as a suspension element of a vibratory device in a system for treating symptoms associated with vestibular conditions, according to an embodiment.
Figure 9C:
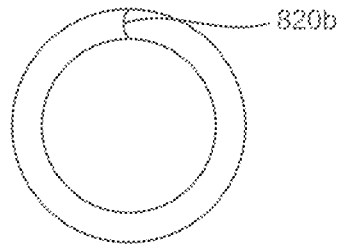

FIG. 9A illustrates a perspective view of a spring 820 that can act as a suspension element in a vibratory device (e.g., the spring 720 in the device 700 described above). The orientation of the spring may reduce the amount of wobbling, rocking, or undesirable movement of the magnet (e.g., the magnet 723) in secondary directions. As shown in FIGS. 9B and 9C, which present views of the two ends of the spring 820, the spring 820 may be orientated such that a first end 820a of the spring 820 begins at a 0° position and a second end 820b of the spring 820 ends at a 180° position. In other embodiments, the spring 820 can being and end at other degree intervals, e.g., 90°, 270°, etc. depending on an effect of gravity on the vibratory device (e.g., a orientation of the spring 820 relative to a direction of gravity). In some embodiments, the orientation of spring 820 can be selected based on the placement of a sensor, such as, for example, an accelerometer or a Hall effect sensor.

FIGS. 10-15 are illustrations of different embodiments of vibratory devices that can be included and/or integrated into various support elements. While one or two vibratory devices may be depicted in these figures, one of ordinary skill in the art should appreciate that any number of vibratory devices can be included in the various embodiments. In the case of multiple vibratory devices, a force level of the vibratory signals from each device can be reduced since a combined effect of the vibratory signals can be at a therapeutically effective level for treating a vestibular condition.

Figure 10:
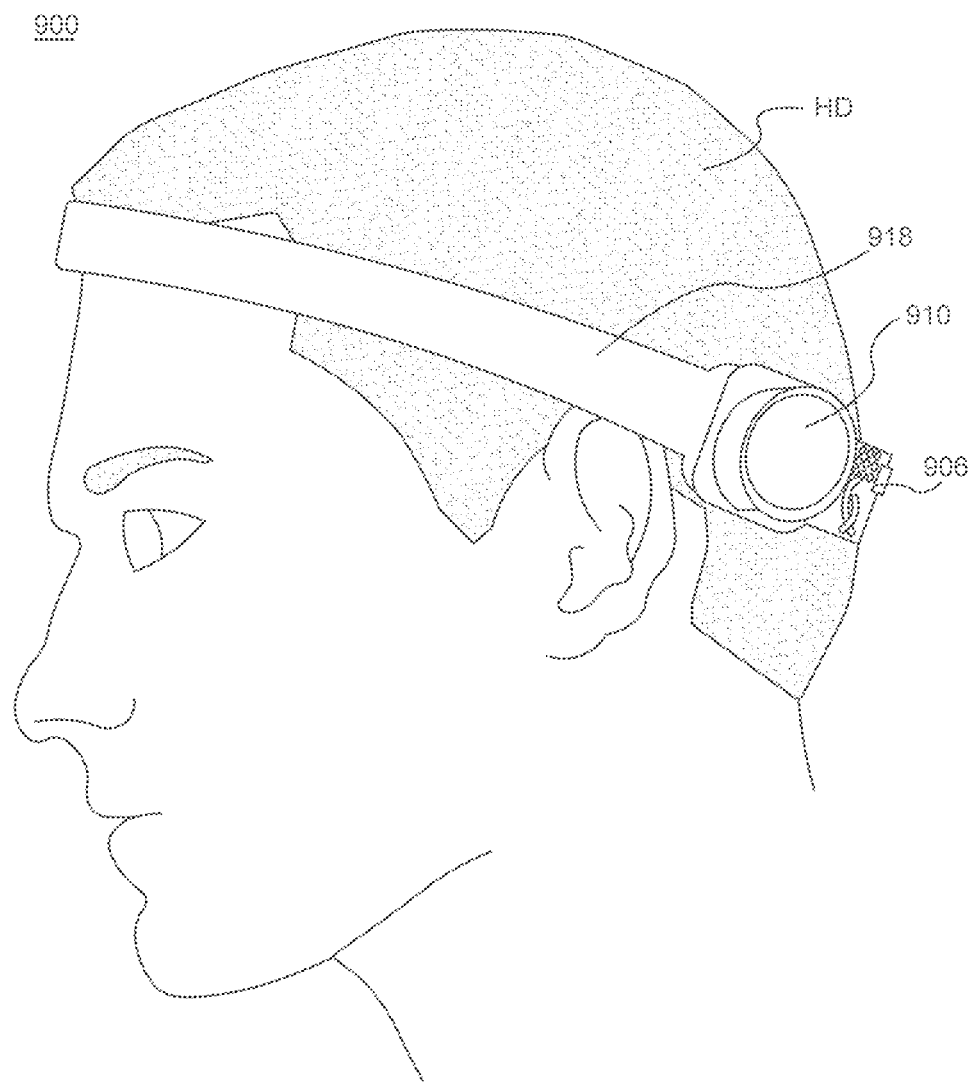
FIGS. 10-15 are schematic illustrations of example vibratory devices including and/or integrated into different support elements, according to various embodiments.

FIG. 10 illustrates a vibratory device 900 with a body 910 integrated into a headband 918 worn on the head HD of a subject. The vibratory device 900 includes a control unit 906, similar to control unit 360, described above. The headband 918 can be made of an elastic, Velcro, metal or plastic, or another material that permits the headband 918 to hold the vibratory device 900 on the head HD of the subject to effectively deliver vibratory signals that can be conducted via bone to the vestibular system. The vibratory device 900 can include an onboard power source (e.g., a battery) to power the control unit 906 and/or other components of the vibratory device 900, or it may be attached via a wire to a power source (e.g., a battery pack) separate from the headband 918. The control unit 906 may include the necessary electrical driving circuitry to generate the vibratory signals to treat vestibular or other conditions disclosed herein. Alternatively, such circuitry and power source may be operatively connected to the vibratory device 900. In some embodiments, the head band 918 may incorporate additional devices such as a headlamp or other suitable head gear to accommodate various needs of a subject.

Figure 11:
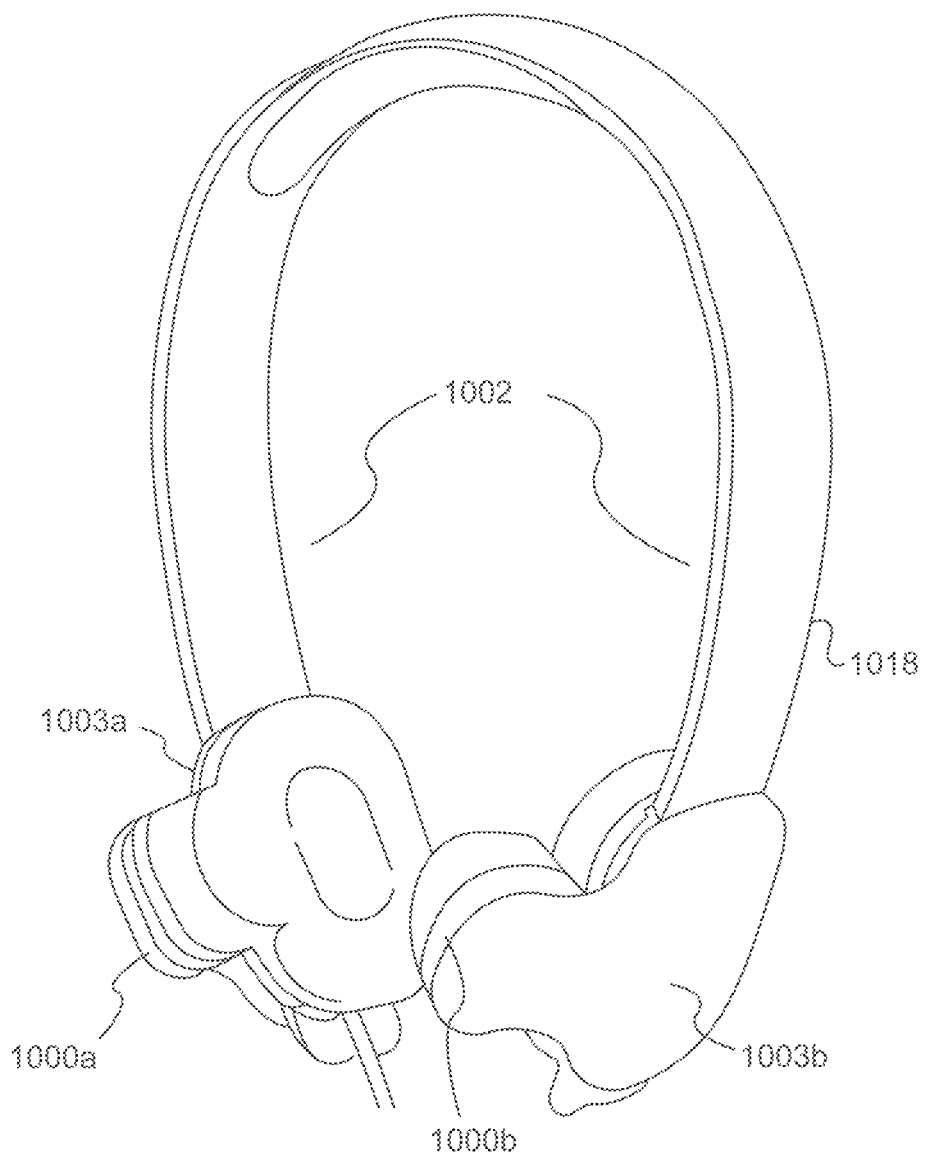

FIG. 11 illustrates the use of vibratory devices 1000a, 1000b integrated into a support element in the form of headphones 1002, according to an embodiment. The headphones 1002 can include audio speakers 1003a, 1003b and an elongated portion 1018 (e.g., band) that connects the audio speakers 1003a, 1003b. In some embodiments, the headphones 1002 may be a passive noise reduction device such as earmuffs, and not include components like audio speakers. Vibratory devices 1000a, 1000b can be similar to any other vibratory device (e.g., vibratory devices 300, 400, 500, 600, 700, 800) described herein. The headphones 1002 may include noise cancellation circuitry that can be used to reduce a level of audible sound caused by vibrations produced by the vibratory devices 1000a, 1000b but not cancel other vibration that is conducted to the vestibular system (e.g., via bone as a result of vibratory signals produced by the vibratory devices 1000a, 1000b). For example, the system 1002 may include noise cancellation circuitry that generates a signal (or signals) that are out of phase with the audible signals produced by the vibratory devices 1000a, 1000b (e.g., at a 180 degrees phase difference). Such an out of phase signal acts to reduce the signal level of such audible signals detected by a subject's vestibular system so that a subject may not hear the audible sounds.

When used in conjunction with headphones 1002, the vibratory devices 1000a, 1000b may be placed adjacent to the audio speakers 1003a, 1003b, such that when the audio speakers 1003a, 1003b are positioned over the ears, the vibratory devices 1000a, 1000b are position overlaying the mastoid bones. Alternatively or additionally, in some embodiments, one or more of the vibratory devices 1000a, 1000b may be incorporated into ear cups of headphones 1002 that may be co-located with the speakers 1003a, 1003b so that an ornamental shape or profile of the headphones 1002 is not affected.

Alternatively or additionally, in some embodiments, one or more of the vibratory devices 1000a, 1000b (or additional vibratory devices not depicted) may be placed along the headband 1018, or extend from a portion of the headphones 1002. Alternatively or additionally, in some other embodiments, one or more of the vibratory devices 1000a, 1000b (or additional vibratory devices not depicted) may be incorporated into an attachment which attaches and detaches to the headphones 1002 so that the user may choose to have the headphones without the vibratory devices 1000a, 1000b or have the headphones with the vibratory devices 1000a, 1000b.

Figure 12:
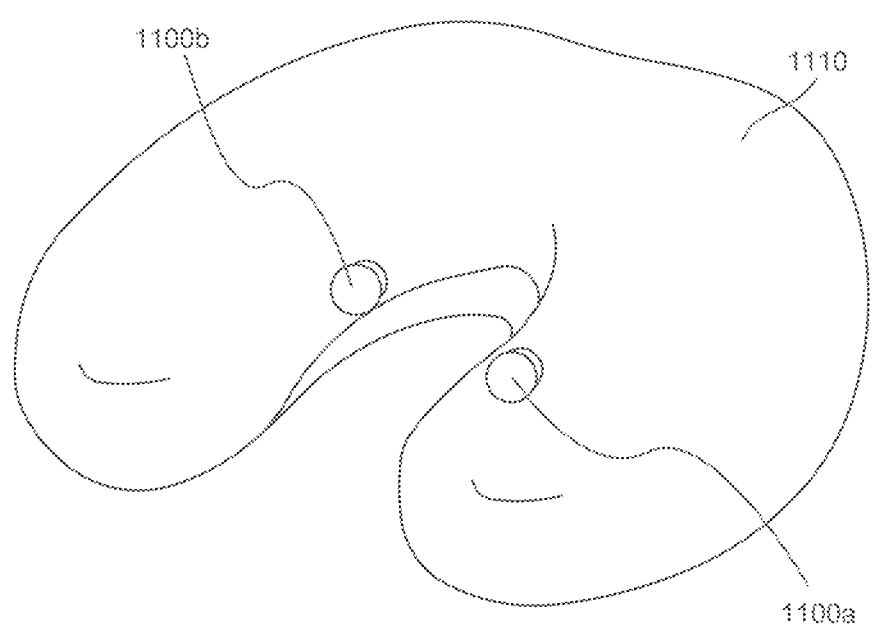

FIG. 12 illustrates yet another embodiment of vibratory devices 1100a, 1100b that may be integrated into, or connected to, a pillow 1110 (e.g., a travel pillow, a cushion, etc.). The location of the vibratory devices 1100a, 1100b on the pillow 1110 may be configured such that when a subject rests his or her head on the pillow 1110, the vibratory devices 1100a, 1100b overlay, for example, the mastoid bones of the subject. In other embodiments, the vibratory devices 1100a, 1100b can be positioned such that they would overlay other areas of the subject's head.

Figure 13:
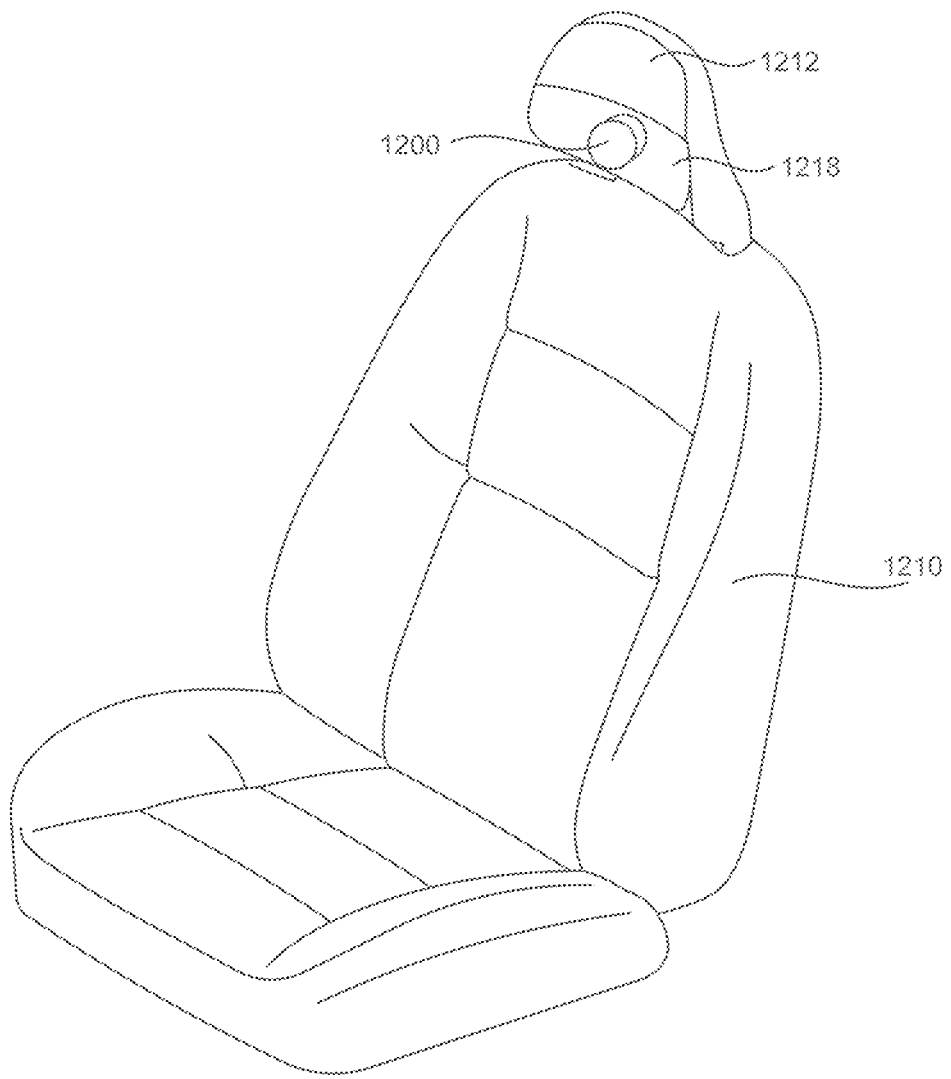

FIG. 13 illustrates yet another embodiment of a vibratory device 1200 that may be integrated into or connected to a seat 1210 (e.g., a car seat, child's booster seat, office chair, etc.). The seat 1210 and the vibratory device 1200 can be configured so that, for example, when a subject's head rests against the seat head rest 1212, the vibratory device 1200 overlays a portion of the head of the subject and is capable of transferring vibratory signals to the head. In some embodiments, the vibratory device can be removably attached to the seat 1210 using a support element 1218 such that it can be removed when not in use. In some embodiments, a vibratory device can be attached to the seatbelt or side of a seat where a subject can apply the vibration by laying their head to the side (e.g., in contact with the vibratory device).

Figure 14:
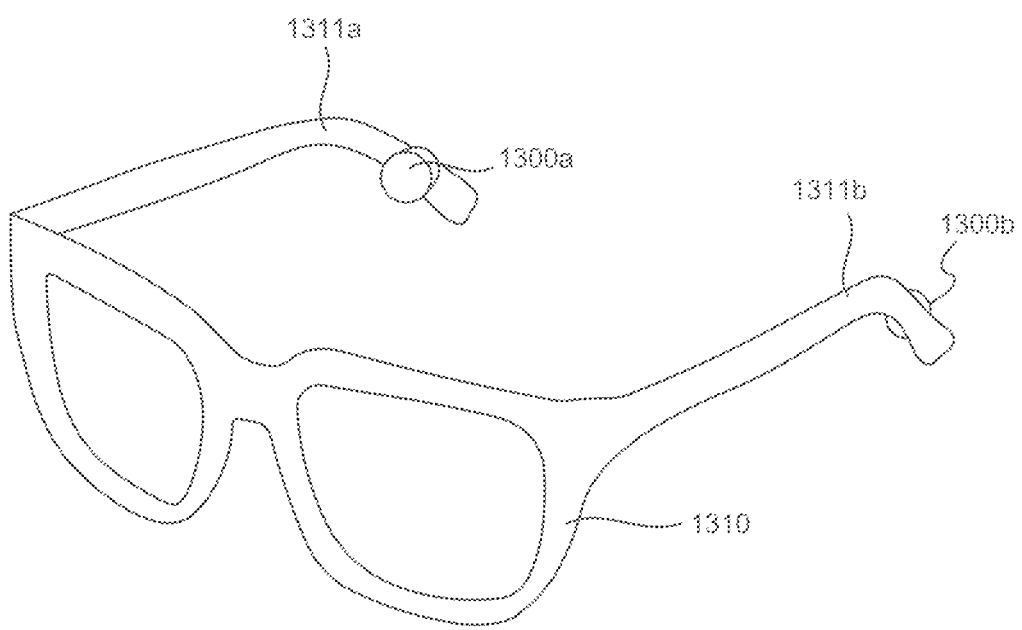

FIG. 14 illustrates another embodiment of vibratory devices 1300a, 1300b that may be integrated into, or connected to, a pair of eyeglasses 1310. While eyeglasses are depicted in FIG. 14, one or ordinary skill in the art would recognize that other types of eyewear (e.g., goggles, sunglasses, safety glasses) may also be suitable for having one or more vibratory devices. The vibratory devices 1300a, 1300b can be positioned on the eyeglasses 1310 on the ear portions 1311a, 1311b that may be in proximal contact with a subject's head during use of the eyeglasses 1310. The vibratory devices 1300a, 1300b can be positioned such that, when a subject wears the eyeglasses 1310, the vibratory devices 1300a, 1300b overlay a portion of the head such that vibratory signals can be transferred to the head and onto the vestibular system.

Figure 15:
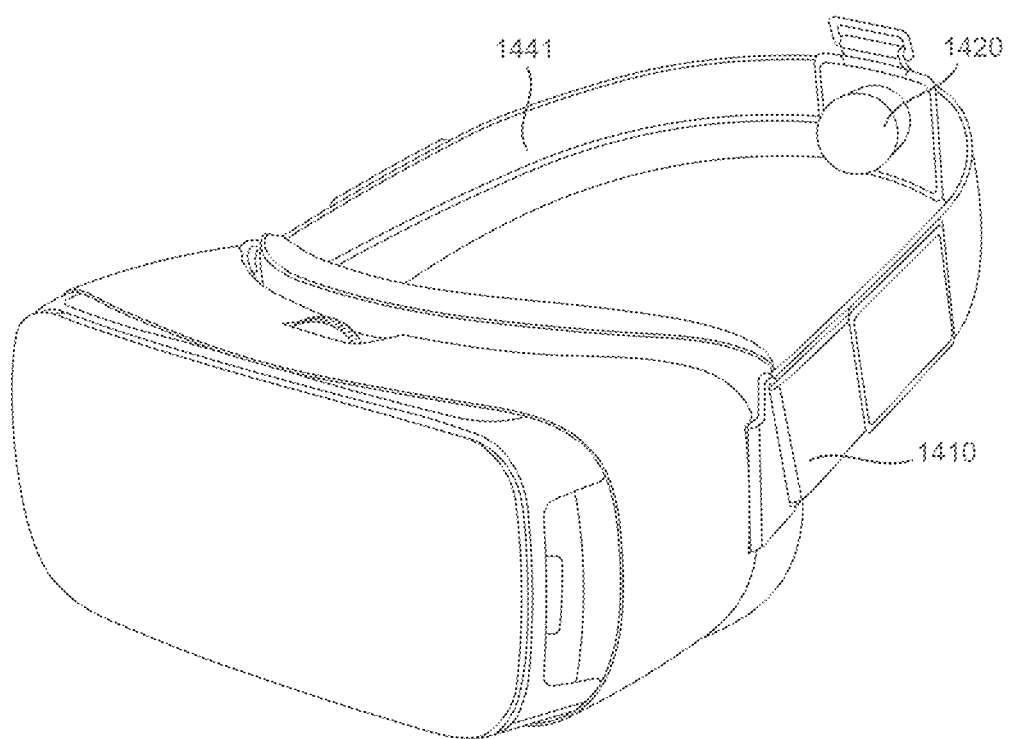

FIG. 15 illustrates another embodiment of vibratory device 1420 mounted or integrated into a virtual reality device 1410 (e.g., a device that can be used to experience virtual reality or augmented reality environments). The vibratory device 1400 can be positioned on the virtual reality device 1410 on a band 1441 of the virtual reality device 1410 that may be used to fasten or support the virtual reality device 1410 on the subject's head, and may be in proximal contact with the head during use of the virtual reality device 1410. One or more vibratory devices may be mounted in any position along the band 1441 of the virtual reality device 1410. The vibratory device 1400 may be positioned on the virtual reality device 1410 such that when the subject wears the virtual reality device 1410, the vibratory device 1400 overlays a portion of the head of the subject such that vibratory signals can be transferred (e.g., via a delivery interface) to the head and onto the vestibular system.

Figure 25A:
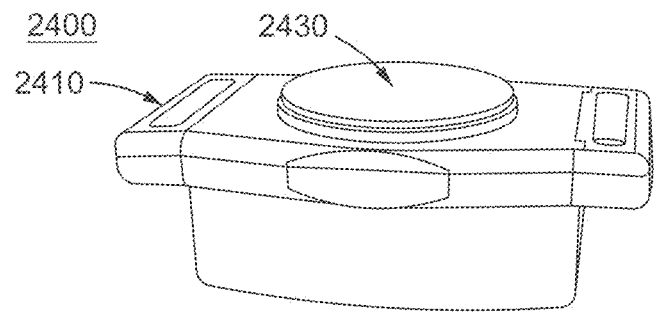
FIGS. 25A-25C are schematic illustrations of a perspective view, a side view and an exploded view of a vibratory device, respectively, as described herein, according to an embodiment.
Figure 25B:
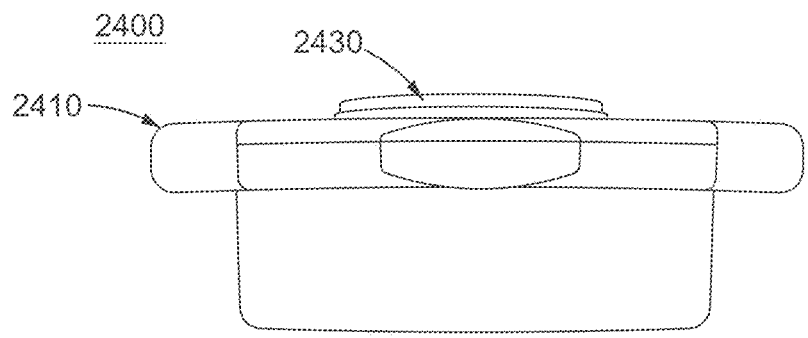
Figure 25C:
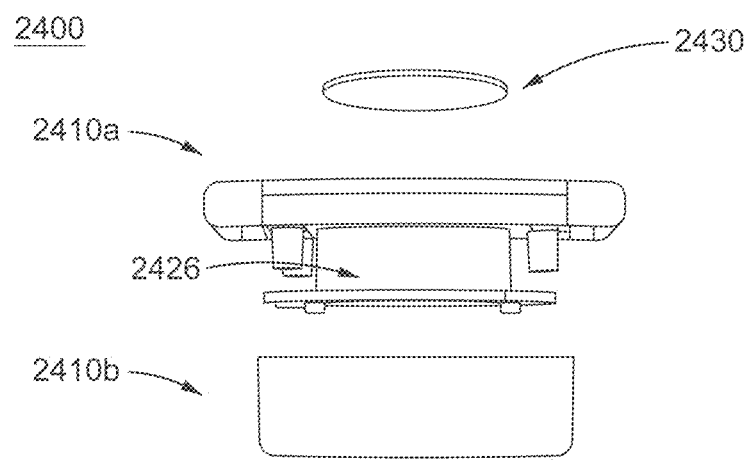
Figure 26:
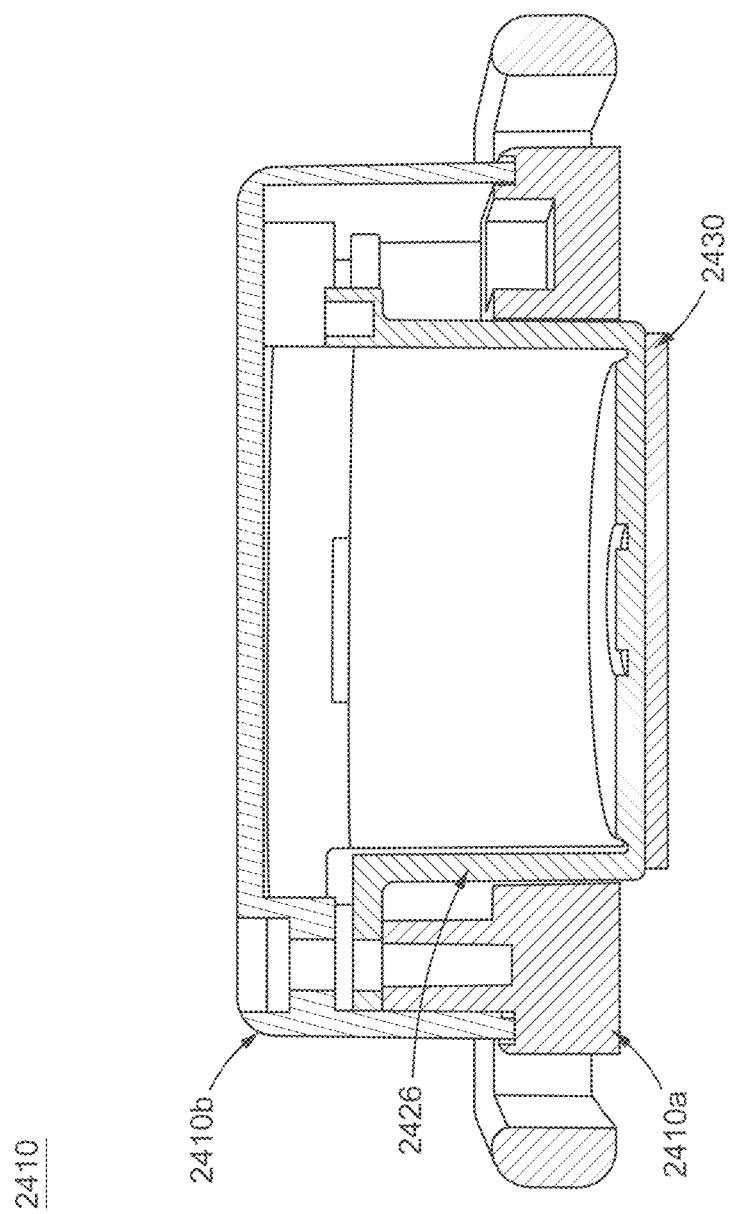
FIG. 26 is a cross-sectional view of a housing of the vibratory device illustrated in FIGS. 25A-25C.

FIGS. 25A-25C show schematic illustrations of a housing 2410 of a vibratory device 2400. The vibratory device 2400 can be similar in structure and/or in function to any of the vibratory devices described herein. For example, the vibratory device 2400 can be similar to the vibratory devices 500, 600, and/or 700 described above. As shown in FIGS. 25A-25C, the vibratory device 2400 can include a delivery interface 2430, and an inner housing 2426 within an outer housing 2410. In some embodiments, as shown in the exploded view in FIG. 25C, the outer housing 2410 can be formed by coupling two portions 2410a and 2410b. FIG. 26 illustrates a cross-section view of the housing 2410 showing the coupling between the two portions 2410a and 2410b, which can be via mechanical attachments, adhesives, etc. Inner housing 2426 can contain a vibrating element (e.g., magnet), a coil, and/or other structures associated with vibratory devices described herein.

Figure 27A:
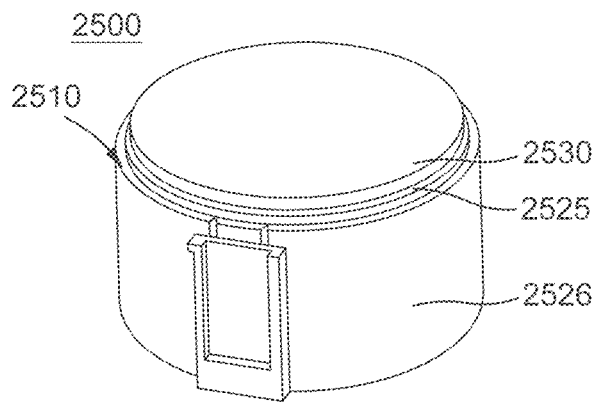
FIGS. 27A-27C are schematic illustrations of a perspective view, a side view and an exploded view of a vibratory device, respectively, according to an embodiment.
Figure 27B:
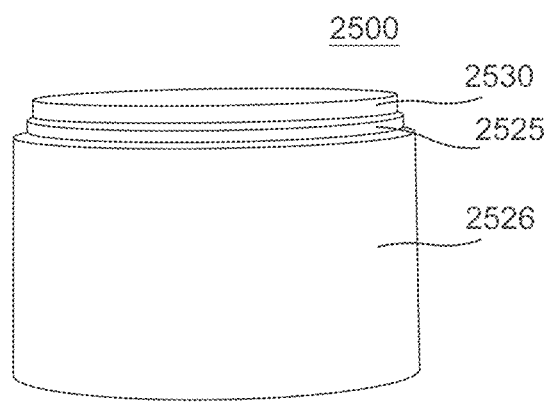
Figure 27C:
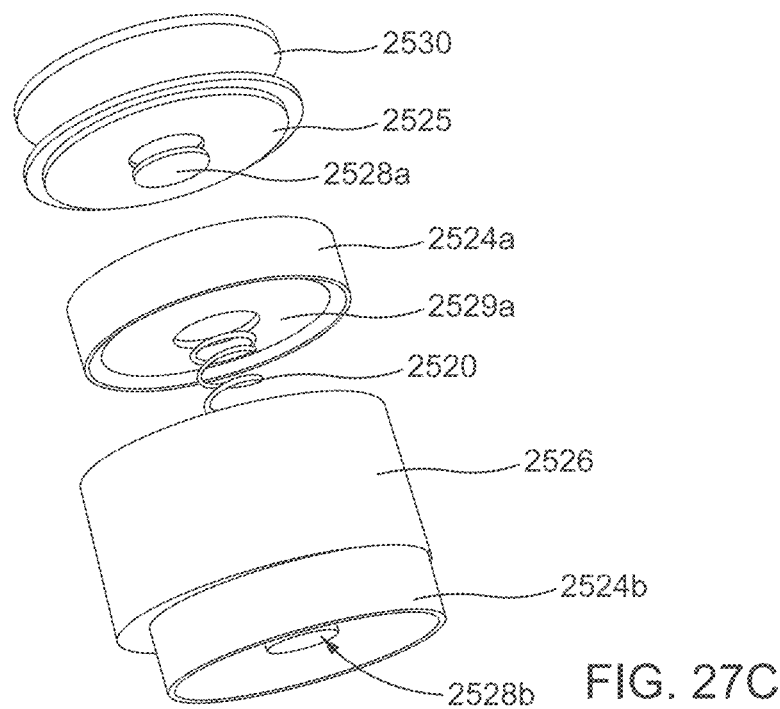
Figure 28A:
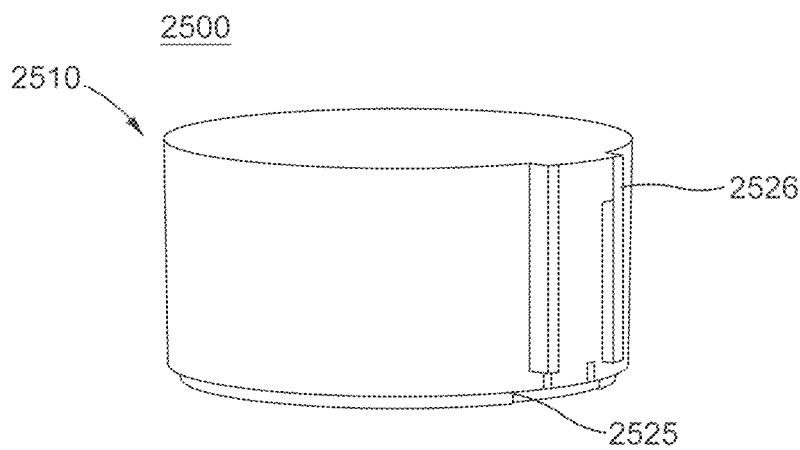
FIGS. 28A and 28B are schematic illustrations of a perspective view and a cross-sectional view of the vibratory device of FIGS. 27A-27C.
Figure 28B:
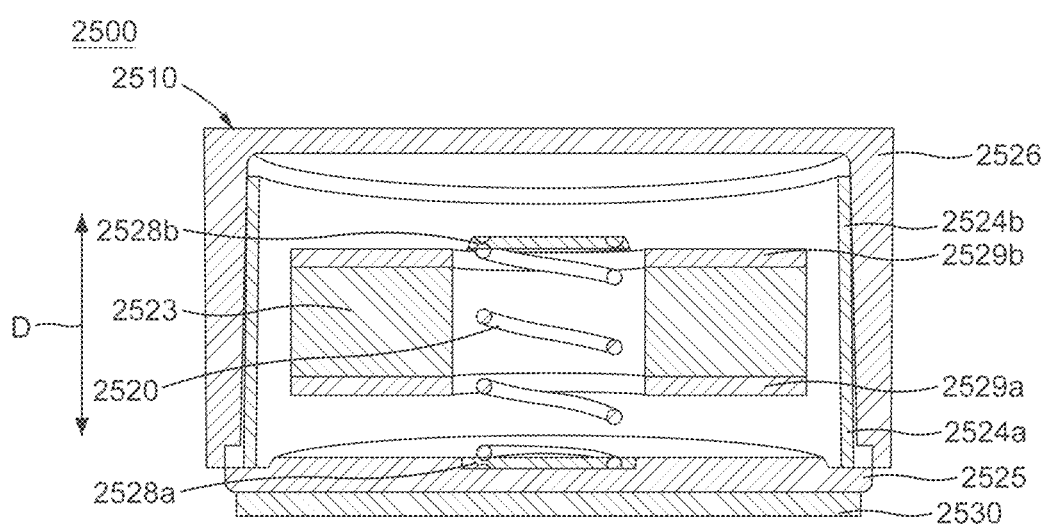

FIGS. 27A, 27B, and 27C illustrate a perspective view, a side view, and an exploded view of a vibratory device 2500, respectively, according to an embodiment. FIGS. 28A and 28B show a perspective view and a cross-sectional side view of the vibratory device 2500, respectively. The vibratory device 2500 can be substantially similar in structure and/or function to other vibratory devices described herein (e.g., vibratory devices 500, 600, and 700). For example, the vibratory device 2500 can include a housing 2510, a delivery interface 2530, and an end cap 2525. The vibratory device 2500 can include electromagnetic coils 2524a and 2524b that are configured to generate magnetic fields to move a magnet 2523. In some embodiments, the coils 2524a and 2524b can be, for example, wound in opposing directions to generate magnetic fields of opposing polarity. While illustrated to have two coils 2524a and 2524b, in some embodiments, the vibratory device 2500 can include a single coil configured to generate magnetic fields of changing polarity to evoke movement of the magnet. The single coil can be driven, for example, by two separate driving circuits generating driving signals of different polarity. In some other embodiments, a single driving circuit can be used to generate signals of different polarity, for example by using a phase switching circuit. The vibratory device 2500 can include a spring 2520 coupled to the magnet 2523 and configured to act as a suspension element. The vibratory device 2500 can include mounting plates 2528a and 2528b and the magnet 2523 can have an opening that extends through a portion of its length such that the spring 2520 can extend through the opening and attach to the far end of the magnet 2523 via the mounting plate 2528b, similar to how the spring 720 is described to attach to a mounting plate 728 in the vibratory device 700.

The magnet 2523 of the vibratory device 2500 can include metallic end plates 2529a and 2529b. In an embodiment, end plate 2529b can function as mounting plate 2328b for the spring 2520. The end plates can be configured to reduce stray magnetic flux. For example, a vibratory device with a magnet acting as the vibratory element may have magnetic field lines that stray far from the magnet and cause the vibratory device to be magnetically attracted to metallic objects. This attraction can produce undesirable side effects and make it cumbersome during use. The end plates 2529a and 2529b can reduce such stray magnetic flux such that the vibratory device 2500 can be used close to other metallic objects without being attracted as much to those objects. Furthermore, the end plates 2529a and 2529b can be used to direct the magnetic field lines out from an end of the magnet in a direction perpendicular to (e.g., toward) the coils 2524a and 2524b generating the magnetic fields such that more of the magnetic field lines are directed to enabling movement of the magnet with respect to the vibratory device 2500, while reducing stray dissipation or leakage of magnetic field lines in a direction parallel to the coil (e.g., not toward the coil).

Figure 38:
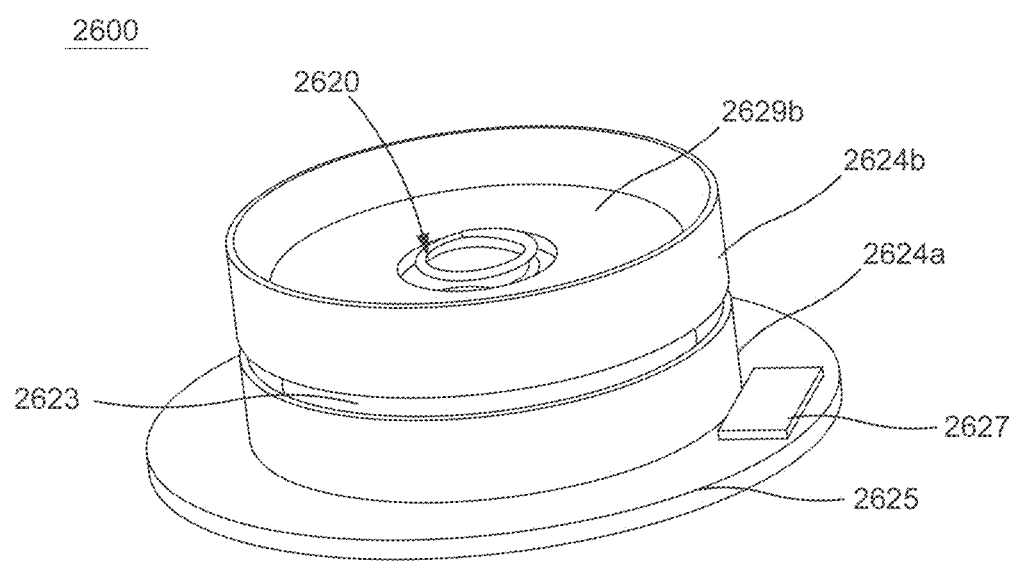
FIG. 38 is a schematic illustration of a perspective view of a vibratory device, according to an embodiment.

FIG. 38 illustrates a perspective view of a portion of the vibratory device 2600 according to another embodiment. The vibratory device 2600 can be substantially similar in several aspects of structure and/or function to other vibratory devices described herein (e.g., vibratory devices 500, 600, 700, and 2500). For example, the vibratory device 2600 can include a housing and a delivery interface (not shown in FIG. 38). The vibratory device 2600 can include an end cap 2625 which can be coupled to the electromagnetic coils 2624a and 2624b that are configured to generate magnetic fields to move a magnet 2623. In some embodiments, the end cap 2625 can include a suitable electrical interface 2627 to deliver electrical signals to the electromagnetic coils 2624a and 2624b. In some embodiments, the coils 2624a and 2624b can be wound in opposing direction to generate magnetic field of opposing polarity. In some embodiments, the coils 2624a and 2624b can be spaced at a suitable distance from each other as shown in FIG. 38, while in other embodiments (e.g., such as shown in FIGS. 28A and 28B) the coils can be placed closer together in space.

The vibratory device 2600 can include a spring 2620 coupled to the magnet 2623 and configured to act as a suspension element. The vibratory device 2600 can include mounting plates (not shown in FIG. 38) and the magnet 2623 can have an opening that extends through a portion of its length such that the spring 2620 can extend through the opening and attach to the far end of the magnet 2623 via a mounting plate, similar to how the spring 2520 is described to attach to a mounting plate 2528b in the vibratory device 2500. The magnet 2623 of the vibratory device 2600 can include metallic end plates 2629a and 2629b (shown in FIG. 29) that are substantially similar in structure and/or function to the metallic end plates 2529a and 2529b of the vibratory device 2500. The end plates 2629a and 2629b can be configured to reduce stray magnetic flux as described with reference to the vibratory device 2500. For example, the end plates 2629a and 2629b can restrict any stray magnetic flux such that the vibratory device 2600 can be used close to other metallic object without being attracted to those objects. The metallic end plates 2629a and 2629b can be used to direct the magnetic field lines out from an end of the magnet in a direction perpendicular to (e.g., toward) the coils 2624a and 2624b generating the magnetic fields) such that more of the magnetic field lines enable movement of the magnet with respect to the vibratory device 2600, while reducing stray dissipation or leakage of magnetic field lines in a direction parallel to the coil (e.g., not toward the coil).

Figure 30:
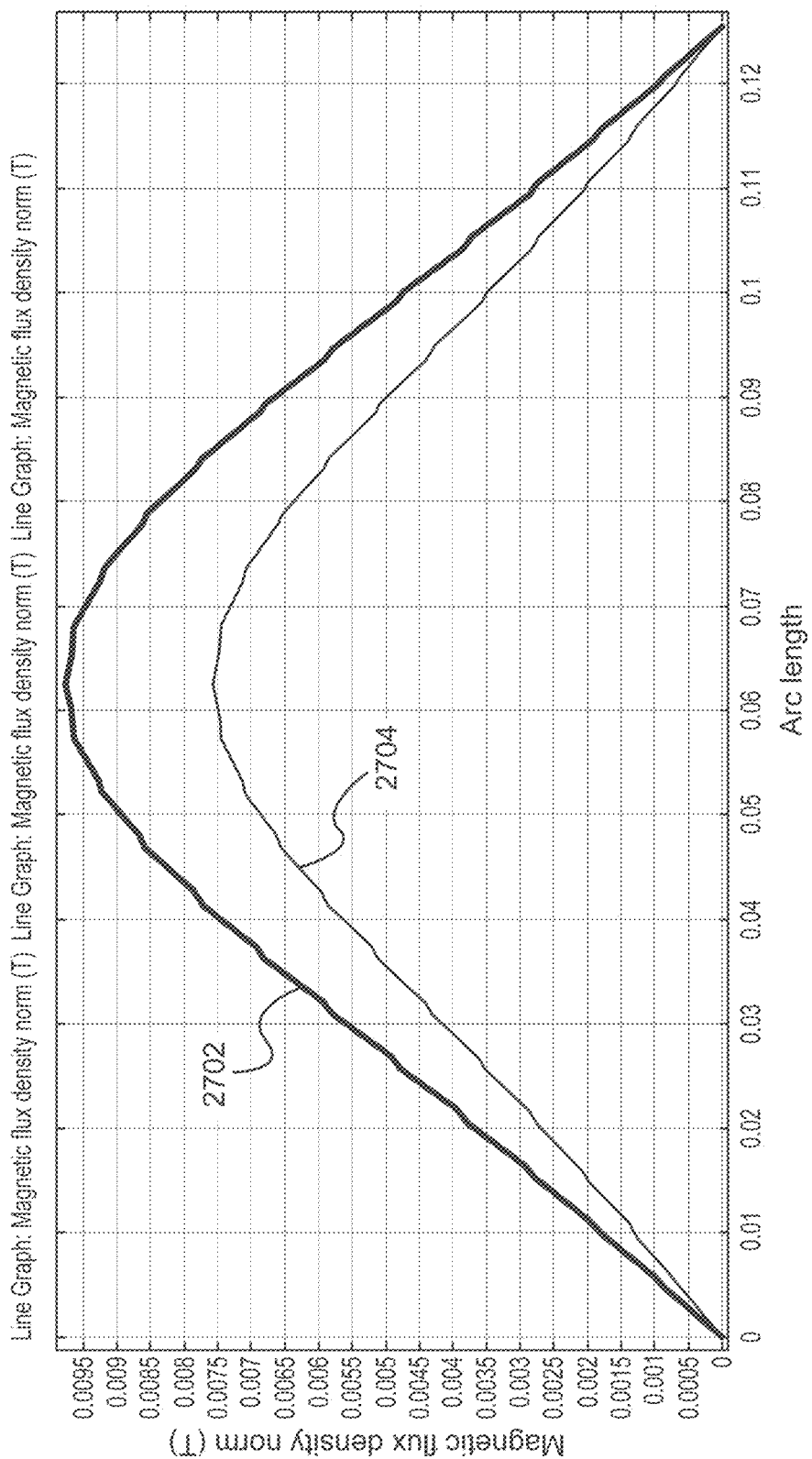
FIG. 30 is a plot of normalized magnetic flux density associated with magnets of vibratory devices, according to several embodiments.

An example illustration 2700a of magnetic field lines focused by the metallic end plates 2629a and 2629b is shown in FIG. 29. The plot 2700b in FIG. 30 of normalized flux density measured over a distribution of arc lengths compares relative magnetic flux leakage of a vibratory device without end plates (line 2702) to reduced magnetic flux leakage of the vibratory device 2600 with end plates 2629a and 2629b (line 2704). As shown, the use of metallic end plates (e.g., 2629a and 2629b) can result in reduced flux leakage. In some embodiments, the end plates 2629a and 2629b can enable more efficient use of magnetic field energy generated by the coils 2624a and 2624b, such that a lesser driving force can be used to evoke desired movement of the magnet 2623 to generate therapeutically effective vibratory signals. In some embodiments, the metallic end plates 2629a and 2629b can be used to focus the magnetic fields lines of the magnet in such a way (e.g., in a directory toward the coils) that less power is required to drive the movement of the magnet. In such embodiments, a smaller magnet 2623 may be used to generate a given strength of vibratory signals, thereby enabling the size of the vibratory device 2600 to be reduced. The metallic plates 269a and 2629b can be of any suitable material that can focus the magnetic fields lines as described above. In an embodiment, the endplates 2529a and 2529b and/or the endplates 2629a and 2629b can be made of low carbon steel.

Figure 31A:
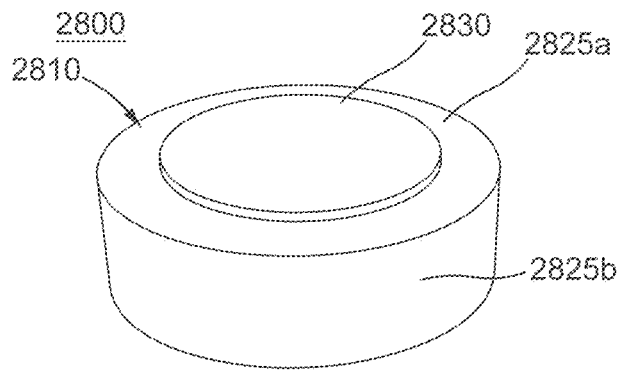
FIGS. 31A-31C are schematic illustrations of a perspective view, a side view and an exploded view of a vibratory device, respectively, according to an embodiment.
Figure 31B:
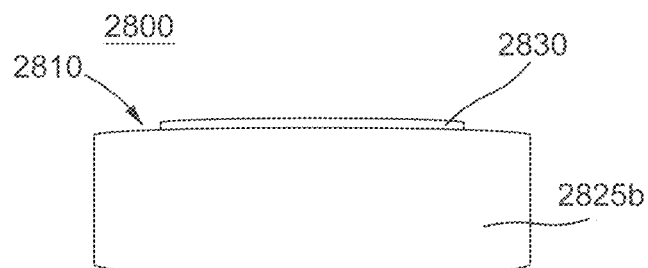
Figure 31C:
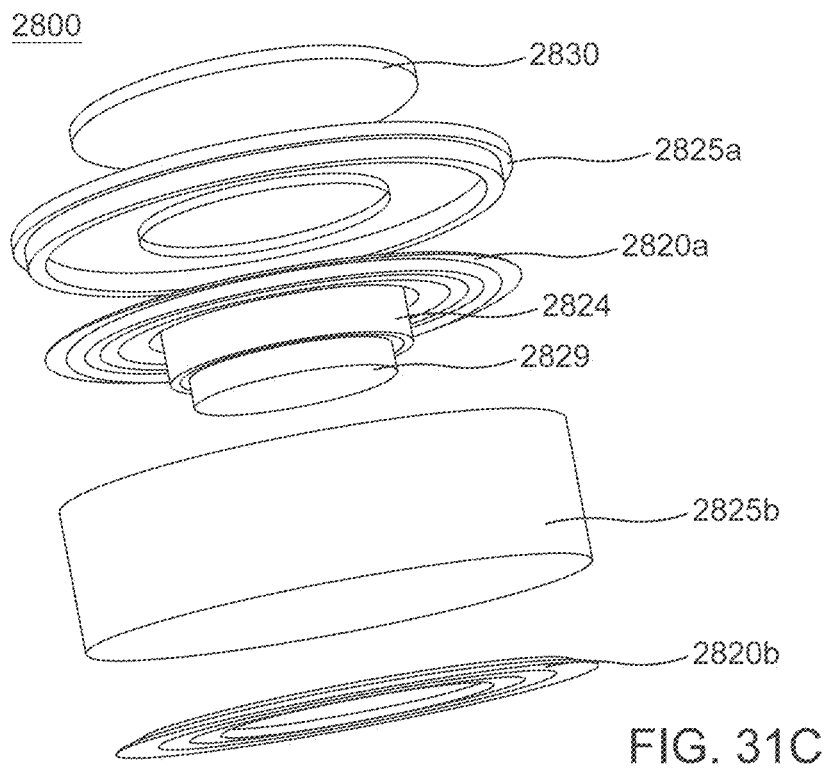

FIGS. 31A, 31B, and 31C illustrate a perspective view, a side view, and an exploded view of a vibratory device 2800, respectively, according to an embodiment. FIGS. 32A and 32B show two cross-sectional views of the vibratory device 2800 of FIGS. 31A-31C. The vibratory device 2800 can be substantially similar in structure and/or function to other vibratory devices described herein (e.g., vibratory devices 500, 600, 700, 2500 and/or 2600). For example, the vibratory device 2800 can include a housing 2810, a delivery interface 2830, and housing portions 2825a and 2825b. The vibratory device 2800 can include an electromagnetic coil 2824 configured to generate magnetic fields to move a magnet 2823, acting as a vibratory element, along the direction of arrow E shown in FIG. 32B.

Figure 33:
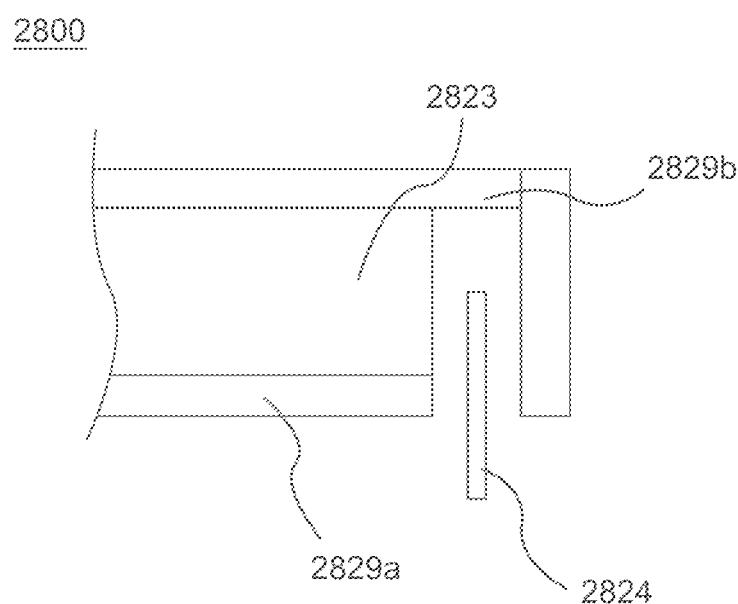
FIG. 33 is a schematic illustration of a magnet, a coil, and metallic plates in the vibratory device of FIGS. 31A-31C.
Figure 34:
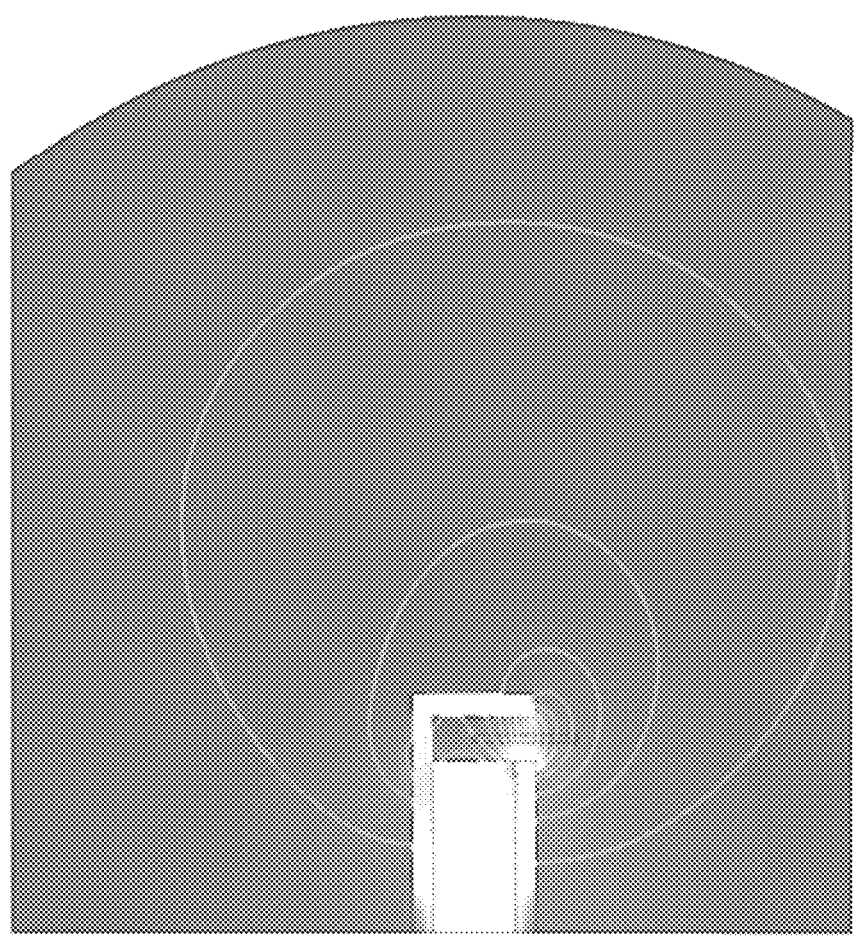
FIG. 34 is an illustration of magnetic field lines associated with the magnet of the vibratory device of FIGS. 31A-31C.
Figure 35:
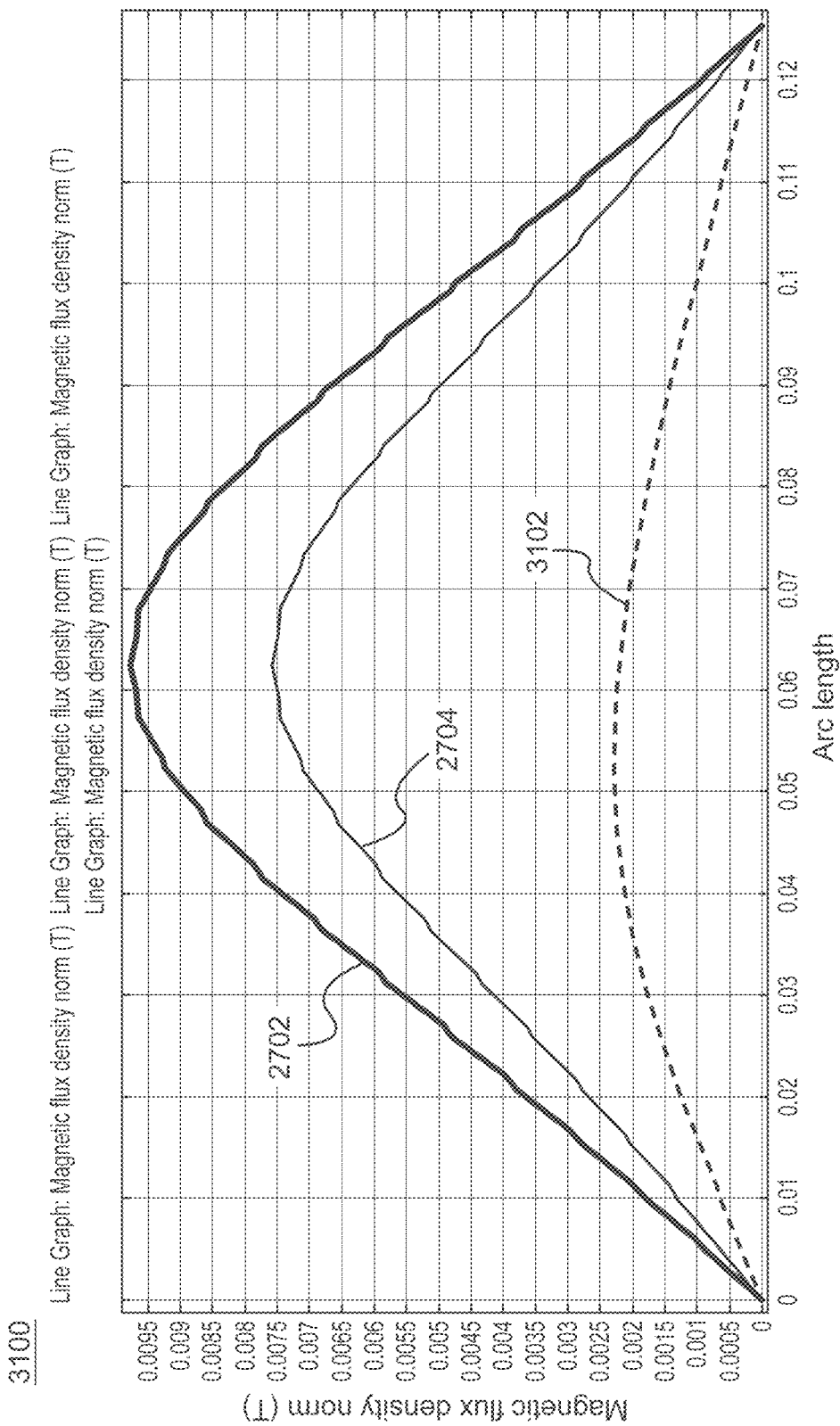
FIG. 35 is a plot of normalized magnetic flux density associated with magnets of vibratory devices, according to several embodiments.

The magnet 2823 can include metallic end plates 2829a and 2829b. The end plates 2829a and 2829b can be substantially similar to the endplates 2529a and 2529b described with reference to the vibratory device 2500. In an embodiment, the metallic end plates 2829a and 2829b can be made of low carbon steel. The metallic end plates 2829a and 2829b can be configured to focus the magnetic field lines of the magnet 2823 in a perpendicular direction with respect to the coil 2824 (e.g., have the magnetic field lines of the magnet 2823 exit an end of the magnet in a direction perpendicular to the coil 2824) while reducing stray dissipation or leakage of magnetic field in the parallel direction. FIG. 33 illustrates the relative positioning of the magnet 2823 with metallic end plates 2829a and 2829b and the coil 2824. FIG. 34 is an example illustration 3000 of magnetic field lines focused by the metallic end plates 2829a and 2829b as shown in FIG. 33. The plot 3100 in FIG. 35 of normalized flux density measured over a distribution of arc lengths compares relative magnetic flux leakage of different vibratory devices. Line 2702 is the magnetic flux density of a vibratory device without end plates, line 2704 is the magnetic flux density with end plates in the configuration shown in FIG. 38, described in reference to FIGS. 29 and 30 above, and line 3102 is the magnetic flux density of the vibratory device 2800 with end plates 2829a and 2829b. As depicted, the use of metallic end plates 2829a and 2829b can result in a reduced flux leakage caused by the driving circuit of the vibratory device 2800 compared to that of other vibratory devices described herein (e.g., vibratory device 2500 or 2600).

The vibratory device 2800 includes suspension elements 2820a and 2820b (e.g., springs) configured to suspend and support the movement of the magnet 2823, in place of a spring, as described in some of the previously described vibratory devices. The suspension elements 2820a and 2820b can be annular pieces of elastic and/or deformable material, e.g., such as cloth, a spider spring, or a flexible membrane. The annular pieces can be coupled to the magnet 2823 and configured to suspend the magnet 2823 at a point of equilibrium such that magnetic field generated by the coil 2824 can move the magnet about the point of equilibrium in the direction indicated by the arrow E. By having the suspension elements 2820a and 2820b extend laterally from the magnet as opposed to extending longitudinally from the magnet (e.g., such as the spring 2520 of vibratory device 2500), the suspension elements 2820a and 2820b can enable a reduction in the total height of the device 2800, while also reducing off-axis movement or wobbling of the magnet 2823 outside the axis defined by the arrow E. In addition, the suspension elements 2820a and 2820b can be configured to expand and compress to provide a restorative force in one or more directions angled relative to an axis of movement of the magnet 2823 such that the suspension elements 2820a and 2820b reduce oscillations of the magnet 2823 in the one or more directions.

Figures 36A, 36B, 36C:
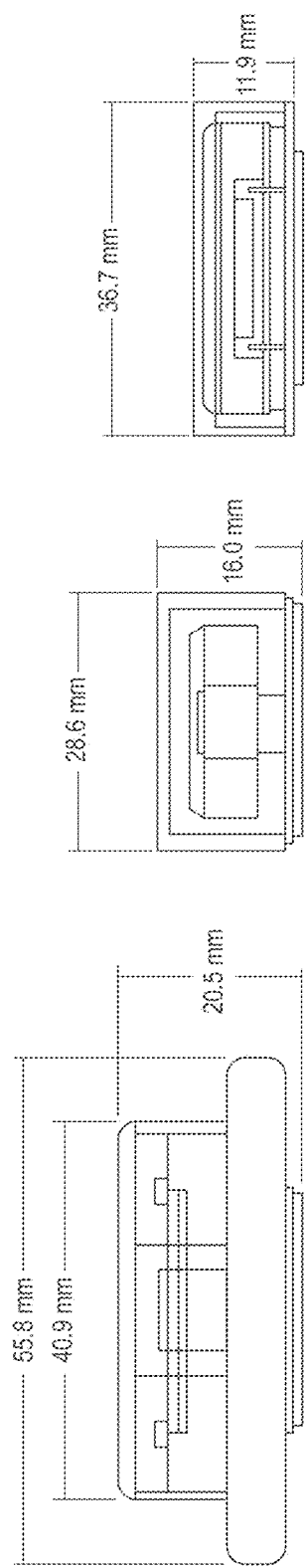
FIGS. 36A-36C are schematic illustrations of cross-sectional views of vibratory devices, according to three different embodiments.

FIGS. 36A, 36B, and 36C illustrate a comparison of dimensions of vibratory devices according to embodiments 700, 2500, and 2800, respectively, as described above. In some embodiments, the lateral dimensions of vibratory device 2800 can further be reduced by reducing a number of folds and/or lateral extension of folds of the suspension elements 2820a, 2820b. Other ways to further reduce the dimensions of one or more vibratory devices described herein can be to reduce components, e.g., remove plastic support structure and have vibratory elements and/or other components be directly mounted to integrated circuit boards.

Figure 37:
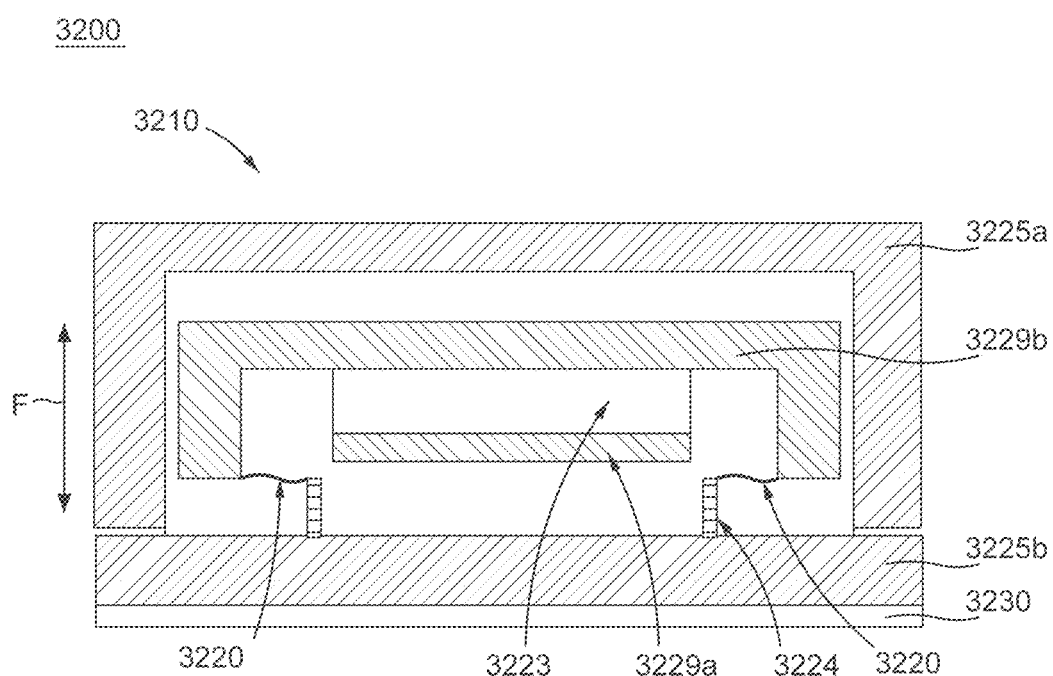
FIG. 37 is a schematic illustration of a cross-sectional view of a vibratory device, according to an embodiment.

FIG. 37 illustrates a vibratory device 3200 according an embodiment. The vibratory device 3200 can be substantially similar in structure and/or function to other vibratory devices described herein (e.g., vibratory devices 500, 600, 700, 2500, 2600 and/or 2800). For example, the vibratory device 3200 can include a housing 3210, a delivery interface 3230, and housing portions 3225a and 3225b. The vibratory device 3200 can include an electromagnetic coil 3224 configured to generate magnetic fields to move a magnet 3223, acting as a vibratory element, along the direction of arrow F shown in FIG. 37.

The magnet 3223 can include metallic end plates 3229a and 3229b. The end plates 3229a and 3229b can be substantially similar to the endplates 2829a and 2829b described with reference to the vibratory device 2800. In an embodiment, the metallic end plates 3229a and 3229b can be made of low carbon steel. The metallic end plates 3229a and 3229b can be configured to focus the magnetic field lines in a perpendicular direction with respect to the coil 3224 while reducing stray dissipation or leakage of magnetic field in the parallel direction.

The vibratory device 3200 can include a suspension element 3220 (e.g., springs) configured to suspend and support the movement of the magnet 3223. The suspension element 3220 can be substantially similar in structure and/or function to the suspension elements 2820a and 2820b described previously with reference to the vibratory device 2800. For example, the suspension element 3220 can be one or more annular pieces of material. The annular pieces can be coupled to the magnet 3223 via the metallic end plate 3229b, as illustrated in FIG. 37. The suspension element 3220 can be coupled to the metallic end plate 3229b in any suitable manner (e.g., glued with an adhesive) and configured to suspend the magnet 3223 at a point of equilibrium such that magnetic field generated by the coil 3224 can move the magnet about the point of equilibrium in the direction indicated by the arrow F. As with the vibratory device 2800, the suspension element 3220 can be configured to reduce a total height of the device 3200 while also reducing off-axis movement or wobbling of the magnet 3223 outside the axis defined by the arrow F. Furthermore, since the suspension element 3220 is disposed between the end plate 3229b and the coil 3224, a lateral dimension of the vibratory device 3200 can also be reduced relative to the vibratory device 2800, depicted in FIGS. 32A and 32B. For example, the suspension element 3220 can be configured to expand and compress to provide a restorative force in one or more directions angled relative to an axis of movement of the magnet 3223 such that the suspension element 3220 reduces oscillations of the magnet 3223 in the one or more directions.

In some embodiments, to increase stabilization of the magnet 3223, an additional component (e.g., a post or pin, such as pin 521) can be added, and can the magnet 3223 can be configured with openings to receive the component through the magnet 3223, similar to magnet 523 of vibratory device 500.

Figure 46A:
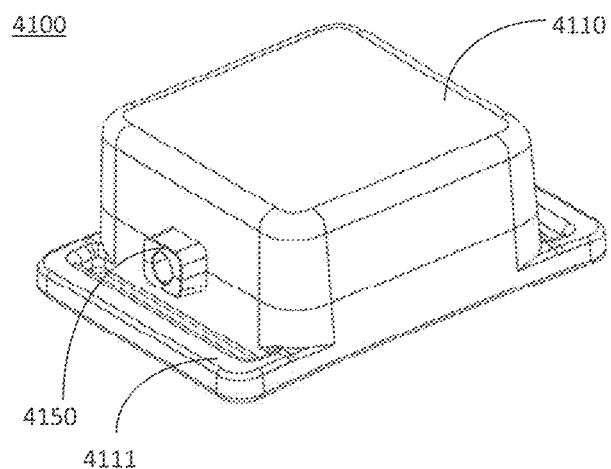
FIGS. 46A and 46B depict different perspective views of an example vibratory device, according to various embodiments.
Figure 46B:
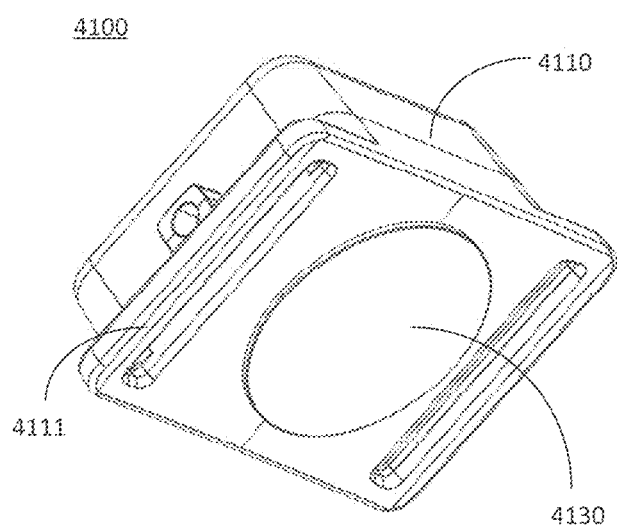
Figure 47:
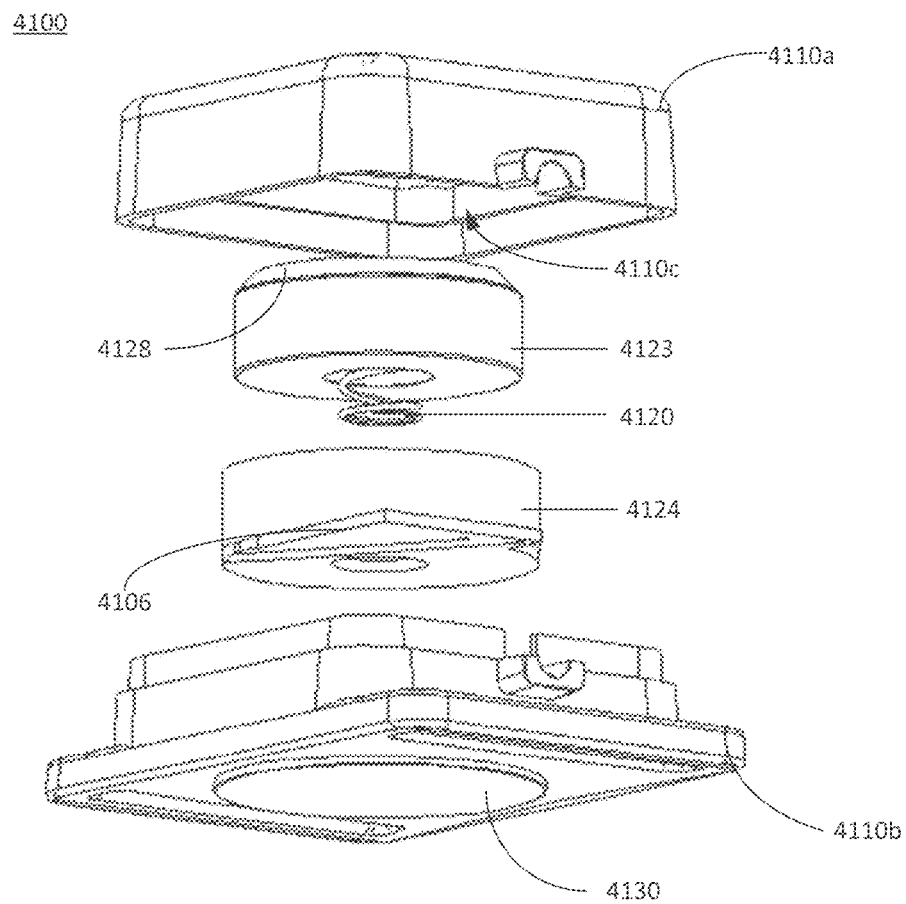
FIG. 47 depicts an exploded view of the vibratory device illustrated in FIGS. 46A and 46B.
Figure 48:
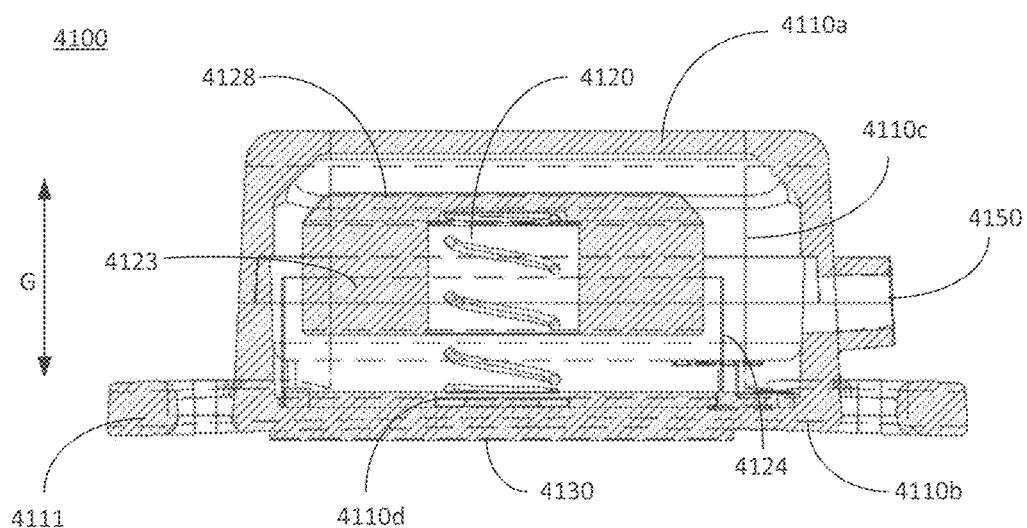
FIG. 48 depicts a cross-sectional view of the vibratory device illustrated in FIGS. 46A and 46B.

FIGS. 46A, 46B, 47, and 48 depict different views of an example vibratory device 4100, according to embodiments disclosed herein. FIGS. 46A and 46B depict different perspective views of the vibratory device 4100. FIG. 47 depicts an exploded view of the vibratory device 4100. FIG. 48 depicts a cross-sectional view of the vibratory device 4100. The vibratory device 4100 can include components that are structurally and/or functionally similar to components of other vibratory devices described herein. For example, the vibratory device can include a housing 4110, a delivery interface 4130, an electromagnetic coil 4124, a vibrating element implemented as a magnet 4123, and a suspension element implemented as a spring 4120.

The housing 4110 can be formed of one or more portions 4110a, 4110b, that together define an interior space 4110c for receiving one or more other components of the vibratory device 4100. For example, the magnet 4123, the electromagnetic coil 4124, the spring 4120, etc. can be received within the space 4110c. The magnet 4123, similar to other magnets described herein (e.g., magnets 723, 2523) can include a recess into which, or hole through which, the spring 4120 can extend. In some embodiments, the magnet 4123 can include a hole that extends through its entire length, and therefore the spring 4120 extends through the magnet 4123 and attaches to a plate or cap 4128 mounted on a top end of the magnet 4123. Alternatively, the magnet 4123 can have a recess that extends through a partial length of the magnet 4123, and the spring 4120 can extend into the recess and attach to a portion of the magnet 4123 (e.g., a top portion of the magnet 4123). In some embodiments, the magnet 4123 can be bounded at its two ends by two end plates, which can be configured to focus the magnetic field lines generated by the coil 4124, as described in more detail above with respect to vibratory device 2500. The magnet 4123, while suspended by the spring 4120, can vibrate along an axis G, i.e., along an axis parallel to a longitudinal axis of the spring 4120. The other end of the spring 4120 can extend into a recess 4110d defined in a portion 4110b of the housing 4110 and attach to the housing 4110. Attachments between the spring 4120 and the magnet 4123 and/or housing 4110 can be via adhesive, welding, friction, screws, or any other suitable mechanism.

The coil 4124 can be configured to generate a magnetic field that causes the magnet 4123 to move along the axis G. The coil 4124 can be disposed within the space 4110c around at least a portion of the magnet 4123. The coil 4124 can be operatively coupled to circuitry (e.g., on an integrated circuit 4106) for generating a signal for driving the movement of the magnet 4123. In some embodiments, the vibratory device 4100 can include an onboard battery or power source for supplying power to the device (e.g., to a signal generator coupled to the coil 4124).

In some embodiments, the housing 4110 can include one or more loops, latches, hooks, or other suitable attachment mechanisms for enable attachment of a headband or other support element (e.g., support element 418), not depicted. In some embodiments, the housing 4110 can define a port or opening 4150. In some embodiments, the port 4150 can enables fluid communication of air into and out of the device. Such communication can enable air to freely pass into and out of the device, preventing or reducing pressure and/or heat build-up within the vibratory device 4100 as the magnet 4123 vibrates within the space 4110c. Alternatively, in some embodiments, the housing 4110 can be configured to define a closed or sealed space 4110c that is fluidically isolated from the surrounding environment. Such embodiments can be suitable for applications where the vibratory device 4110 may be used underwater or in other environments that can potentially damage the internal circuitry and components of the device 4100. In some embodiments, the port 4150 can be used to pass electrical connections into and out of the device, e.g., in a case where a printed circuit board or other circuitry and/or electronics (e.g., control unit, sensor(s), etc.) is coupled via wired connections to the vibratory device.

Other components and/or functionality of the vibratory device 4100, as well as variations of such components and/or functionality, are similar to those of other vibratory devices described herein, and therefore are not repeated again with respect to vibratory device 4100. Such components, functionality, and/or variations thereof can be appreciated by referencing the relevant descriptions of the other vibratory devices described herein.

Figure 49:
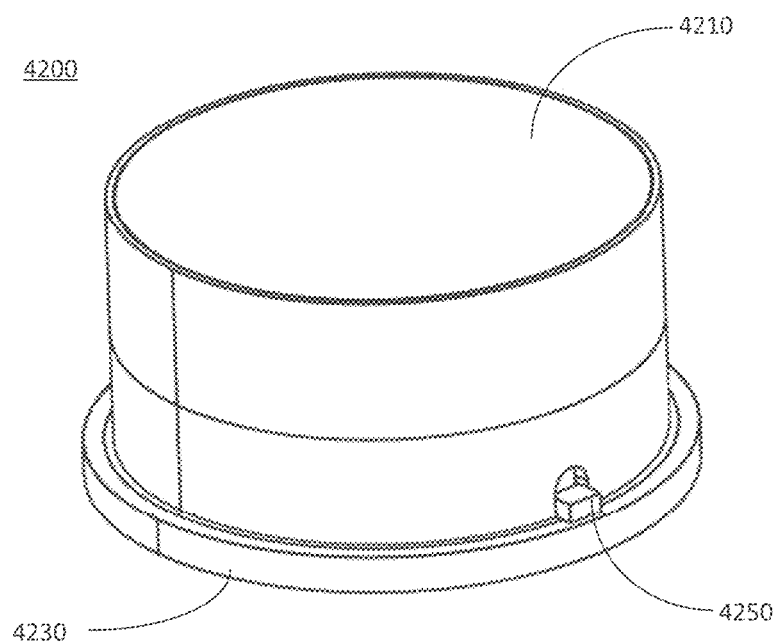
FIG. 49 depicts a perspective view of an example vibratory device, according to various embodiments.
Figure 50:
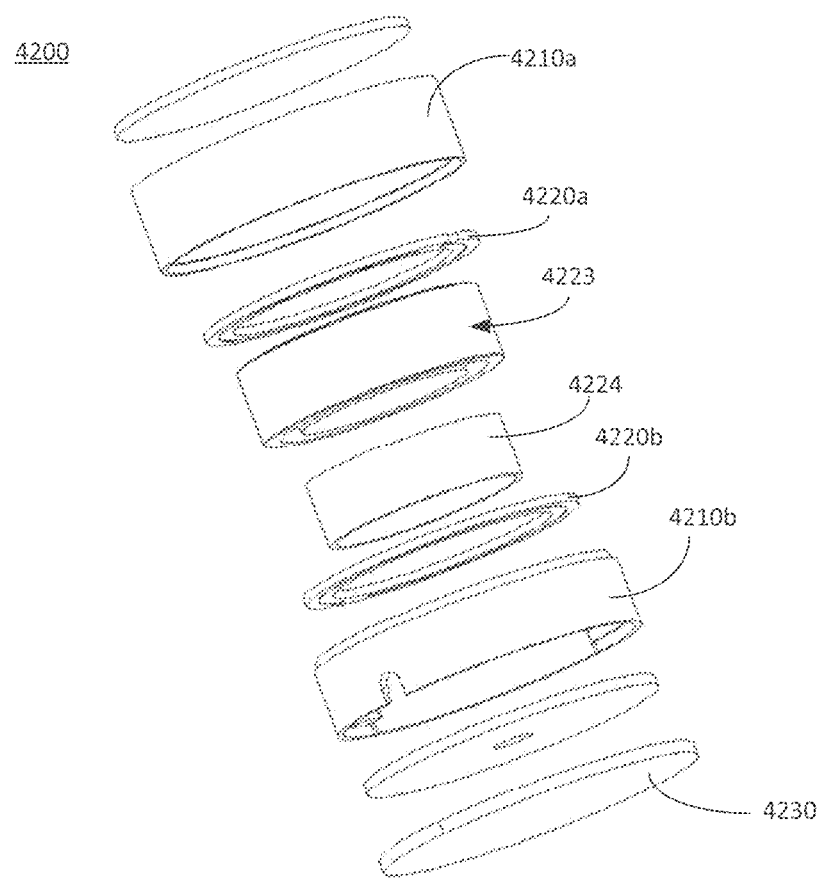
FIG. 50 depicts an exploded view of the vibratory device illustrated in FIG. 49.
Figure 51:
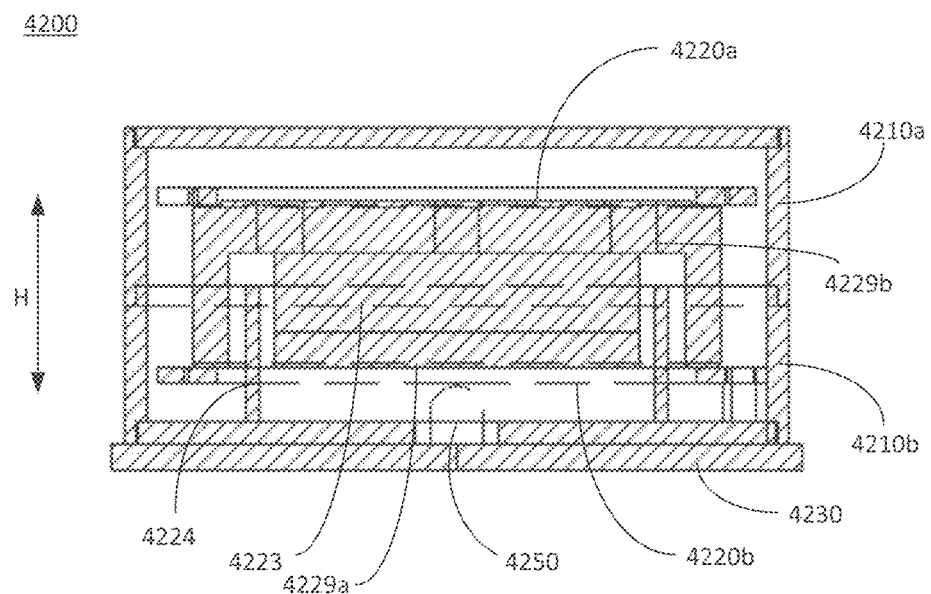
FIG. 51 depicts a cross-sectional view of the vibratory device illustrated in FIG. 49.
Figure 52:
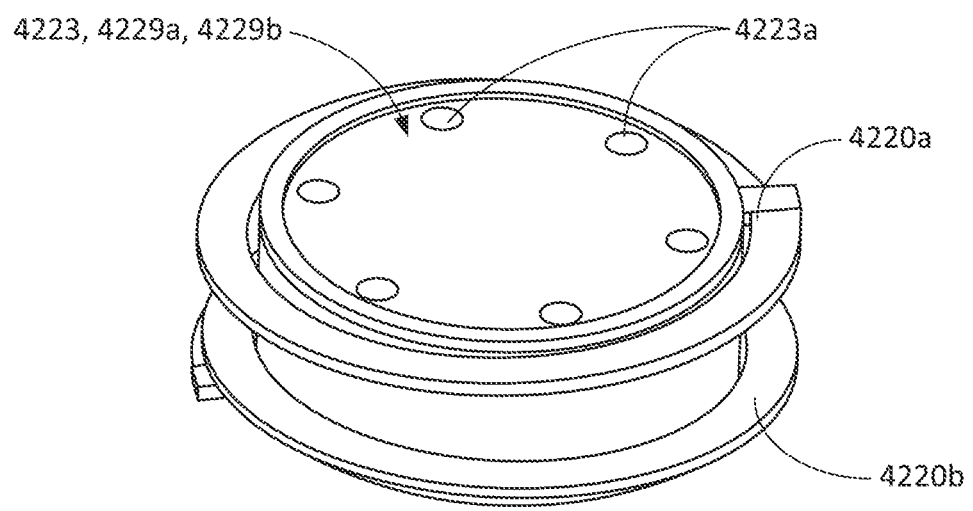
FIG. 52 depicts an enlarged view of a vibratory element of the vibratory device illustrated in FIG. 49.

FIGS. 49-52 provide different views of an example vibratory device 4200, according to embodiments disclosed herein. FIG. 49 depicts a perspective view of the vibratory device 4200. FIG. 50 depicts an exploded view of the vibratory device 4200. FIG. 51 depicts a cross-sectional view of the vibratory device 4200. FIG. 52 depicts an enlarged view of a vibrating mass (e.g., magnet 4223, end plates 4229a, 4229b) and suspension elements or spring 4220a, 4220b of the vibratory device 4200. The vibratory device 4200 can include components that are structurally and/or functionally similar to components of other vibratory devices described herein. For example, the vibratory device can include a housing 4210, a delivery interface 4230, an electromagnetic coil 4224, a vibrating element implemented as a magnet 4223, and suspension elements implemented as springs 4120a, 4120b.

The housing 4210, similar to other housings described herein, can be formed of one or more portions 4210a, 4210b, that together define an interior space for receiving other components of the vibratory device 4210. In some embodiments, the housing 4210 can define an opening or port 4250 that can receive an electrical wire into the device and/or enable fluid communication of air into and out of the device, similar to vibratory device 4100. Alternatively, the housing 4210 can define a sealed space or compartment for housing the other components of the vibratory device 4210.

The magnet 4223 can be structurally and functionally similar to the magnet 2823, in which the magnet 4223 includes metallic end plates 4229a, 4229b. The metallic end plate 4229a can have a diameter that is substantially similar to the magnet 4223, while the metallic end plate 4229b can include a portion that surrounds the magnet 4223 and/or metallic end plate 4229a. The two end plates 4229a, 4229b can be configured to focus the magnetic field lines generated by the coil 4224.

The suspension elements or springs 4220a, 4220b are configured to suspend and support the movement of the magnet 4223. The springs 4220a, 4220b can be formed of metal and have a generally flat structure. The springs 4220a, 4220b, by being formed of metal, provide greater consistency, durability, and longevity to the device 4200, e.g., maintaining more consistent movement of the magnet 4223 over time compared to rubber springs. The springs 4220a, 4220b can be coiled or wrapped around a perimeter of the magnet 4223 and/or metallic end plates 4229a, 4229b. By having the springs 4220a and 4220b extend laterally from the magnet 4223 as opposed to extending longitudinally from the magnet 4223, the springs 4220a, 4220b can enable a reduction in the total height of the device 4200, while also reducing off-axis movement or wobbling of the magnet 4223 outside the axis defined by the arrow H. In some embodiments, the springs 4220a, 4220b can be wrapped or coiled in opposite directions to further reduce lateral or off-axis movement of the magnet 4223. The magnet 4223 and/or metallic end plates 4229a, 4229b can be configured to move through openings defined by the springs 4220a, 4220b. Attachments between the springs 4220a, 4220b and the magnet 4223 and/or housing 4210 can be via adhesive, welding, friction, screws, or any other suitable mechanism.

In some embodiments, the magnet 4223 and/or to the metallic end plates 4229a, 4229b coupled to the magnet can include one or more openings or holes 4223a that enable air to pass between the sides of the magnet 4223. By allowing air to pass between the sides of the magnet 4223, the vibratory device 4200 can operate more efficiently, e.g., by reducing pressure build up on either side of the magnet 4223, e.g., when the magnet 4223 is within a sealed housing 4210. Without these holes, the movement of the magnet 4223 can produce pressure that increases stiffness, which can increase the resonance of the device 4200 (e.g., increases the vibrational frequency (e.g. fundamental frequency) of the device). By adding the holes to the magnet 4223 and/or to the metallic end plates 4229a, 4229b, the stiffness of the device 4200 can be reduced to lower a fundamental or lowest resonant frequency of the device 4200.

Other components and/or functionality of the vibratory device 4200, as well as variations of such components and/or functionality, are similar to those of other vibratory devices described herein, and therefore are not repeated again with respect to vibratory device 4200. Such components, functionality, and/or variations thereof can be appreciated by referencing the relevant descriptions of the other vibratory devices described herein.

III. Sensors and Feedback

In embodiments described herein, a vibratory device that applies vibratory signals that can be conducted via bone conduction to a vestibular system of a subject can be used to treat maladies and/or symptoms associated with such maladies. For example, from studies described herein, vibratory devices within a specific frequency and force range have been shown to be therapeutic in mitigating symptoms brought on by vestibular maladies and vestibulopathies, including vertigo, dizziness, ototoxicity, vestibulotoxicity, motion sickness, virtual reality sickness, spatial discordance, sopite syndrome, and/or nausea. The onset of these symptoms can be predicted by monitoring biometrics of a subject including, for example, skin conductance, brain wave patterns measured by an electroencephalogram (EEG), electromyography (EMG), temperature, eye movement, heart rate, heartbeat or cardiac waveforms (i.e., PQRST waveforms) measured through electrocardiogram (EKG), blood pressure, oxygen saturation (e.g., SpO2), respiratory signals, nerve evoked potentials (e.g., vagal nerve monitoring), sweat toxicology, and stress hormone levels (e.g., cortisol levels). Additionally or alternatively, the onset of these symptoms can also be predicted by monitoring environmental metrics, including, for example, ambient sound, temperature, vibrations/shakiness, position, motion, acceleration, location, and ambient air pressure.

In some embodiments, a therapeutic vibratory device or bone conduction device may be used with one or more sensors (e.g., biometric sensors, environmental sensors, etc.). The sensors can be integrated into the vibratory device and/or be operatively coupled to the vibratory device. A processor can be used to monitor for an onset or subset of a symptom (e.g., by monitoring the data collected by the one or more sensors) and control the operation of the vibratory device (e.g., turn on or off power to the vibratory device, vary a force level or frequency of the vibrations) based on biometric and/or environmental metric feedback. In some embodiments, a processor may also record historical trends in the frequency, severity, and duration of vestibular maladies and vestibulopathies, e.g., based on monitoring biometrics and/or environmental metrics. The sensors and/or processor can be physically connected or coupled to vibratory device or part of separate device(s) that can communicate with the vibratory device, e.g., via a wired and/or wireless connection.

As described above with reference to FIG. 4A, a vibratory device 350 can include one or more sensors 390. Sensor(s) 390 can be configured to measure information associated with a vestibular system of a subject and/or other biometrics. Optionally, sensor(s) 390 can be configured to measure information associated with an environment surrounding a subject. As depicted in FIG. 4A, sensor(s) 390 can be operatively coupled to a control unit 360, including a processor 364. Sensor(s) 390 via this coupling can communicate information associated with one or more biometrics and/or environmental metrics to the control unit 360. Control unit 360 (e.g., via processor 364) can then control an operation of a vibratory device (e.g., vibratory device 300) based on the biometric and/or environmental metric data, which can indicate an onset and/or subset of symptoms associated with the vestibular system. For example, upon detecting an onset of symptoms, control unit 360 can activate signal generator 370 and/or amplifier 380 to provide an electrical signal to power on vibratory device 300, and/or adjust one or more parameters of the electrical signal to vary a frequency and/or a force level of the vibratory signal applied to the subject.

In some embodiments, skin conductance (e.g., measured by a sensor 390) can be used to detect a change in a physiological state of a user, e.g., an onset, subset, and/or severity of a physiological condition, such as, for example, nausea. For example, nausea often develops in waves, with each wave bringing the sensation of being warmer leading to an increase in perspiration. Skin conductance can be correlated with the severity of nausea, e.g., as the perspiration from nausea lowers a resistivity of the skin (i.e., increasing skin conductance). These increases in skin conductance often come in spikes along with the waves of nausea. Accordingly, skin conductance can be a biometric indicator that can be used to signal to a control unit and/or processor that nausea is developing. The processor can then turn on the vibratory device (e.g., activate a signal generator to supply an electrical signal that causes a vibratory element to generate a vibratory signal) and/or increase a power to the vibratory device. In some embodiments, the processor can turn on and/or increase power to a vibratory device in response to a spike in skin conductance, e.g., a sudden change in skin conductance such as a change in skin conductance that is greater than a certain amount and/or percentage within a preset period of time. In some embodiments, the processor can turn on and/or increase power to a vibratory device in response to skin conductance rising above a certain threshold. For example, if 2 µS is set as the baseline skin conductance for an individual, then the force level of the transducer could be adjusted up once skin conductance rises above 6 µS.

Figure 39:
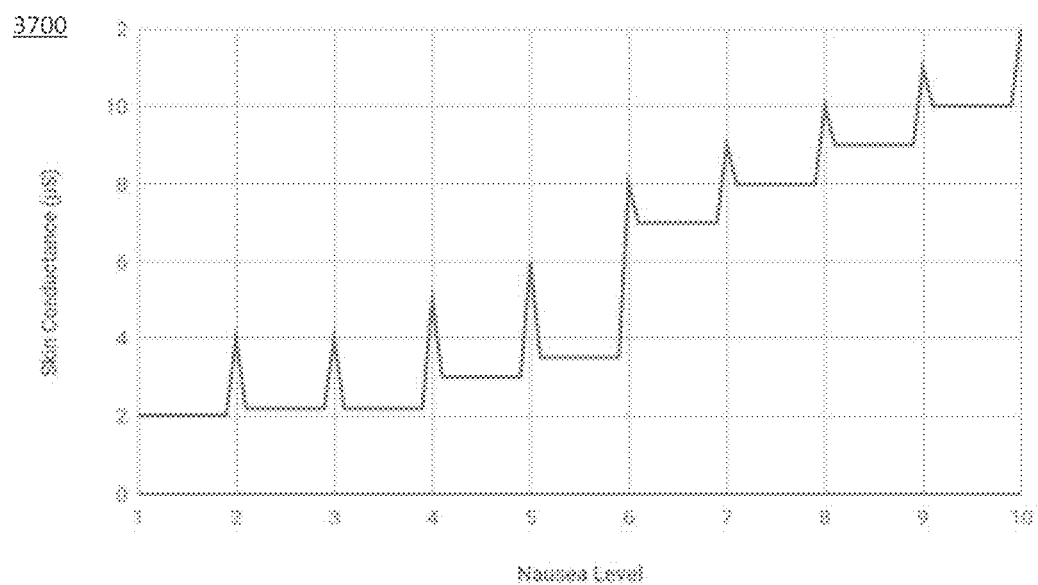
FIG. 39 is a graph of skin conductance to nausea level of a subject.

FIG. 39 is a graph 3700 that demonstrates example changes in skin conductance as a function of reported nausea. As depicted, skin conductance increases with increasing nausea, with spikes of increase in skin conductance at various points along an increase in nausea level.

In some embodiments, changes in brainwave activity (e.g., measured by a sensor 390) can be used to detect an onset, subset, and/or severity of nausea. The analysis of brainwaves, as monitored by an EEG, can be a predictive tool of a subject trending towards or away from experiencing nausea. For example, if a multivariate normal probability density function (MVNPDF) of a subject's EEG data is 0, there is a low probability of nausea. Alternatively, if the MVNPDF of the EEG data is 1, there is a high probability of nausea. Accordingly, the time average of the MVNPDF of EEG data can be used as a biometric indicator of nausea developing. A processor can monitor this time average, and based on the time average, adjust the power being supplied to a vibratory device. For example, when the time average of the MVNPDF is increasing, the processor can turn on and/or increase power to a vibratory device. Alternatively, when the time average of the MVNPDF is decreasing, the processor can turn off and/or decrease power to a vibratory device. In some embodiments, another biometric indicator may be if the MVNPDF (averaged or instantaneous) is above or below a certain predefined threshold, in which case the power to the vibratory device can be increased or decreased, respectively.

Figure 40:
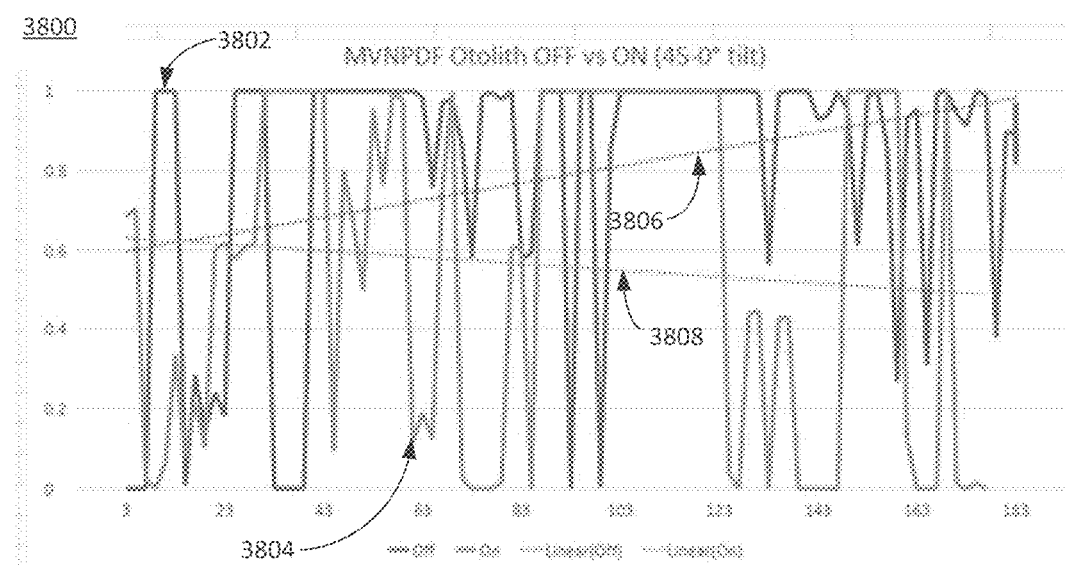
FIG. 40 is a graph of a multivariate normal probability density function (MVNPDF) of electroencephalogram (EEG) data of a subject over time, while having the vibratory device turned off (darker lines) and while having a vibratory device turned on (lighter lines).

FIG. 40 is a graph 3800 of the MVNPDF of EEG data as a function of time of a subject who was in a flight simulator while wearing a therapeutic vibratory or bone conduction device. The darker line 3802 represents the MVNPDF of the subject with the vibratory device turned off, and the lighter line 3804 represents the MVNPDF of the subject with the vibratory device turned on. The trend lines of the MVNPDF are also shown in dotted lines 3806, 3808, with a positive slope (e.g., associated with an increased probability of nausea) when the device is turned off and a negative slope (e.g., associated with a decreased probability of nausea) when the device is turned on.

In some embodiments, EEG data can be used to measure the cognitive load of a subject, which may indicate foggy headedness or inability to concentrate, both of which can be symptoms of vestibular migraine and/or vertigo.

In some embodiments, a sensor (e.g., sensor 390), such as an EMG, can be used to measure cervical vestibular-evoked myogenic potentials (cVEMP) and ocular vestibular-evoked myogenic potentials (oVEMP). EMG data (e.g., cVEMP and/or oVEMP) can be used, for example, in diagnosing vestibular maladies and/or vestibulopathies. For example, EMG data can be used to monitor muscle spasms, yawning, sneezing, and/or chewing, which may signal a symptom such as nausea or dizziness is developing. A processor may then modulate (e.g., adjust) the power to a vibratory device based on, e.g., a sudden or fast change in EMG metrics, or if the EMG data rises above or falls below one or more predefined thresholds.

In some embodiments, a sensor (e.g., sensor 390) can be used to measure body temperature. For example, increases in body temperature can signal an onset of nausea. Body temperature has natural fluctuations, but sudden or fast rises can be a sign that nausea is developing. Accordingly, biometric indicators of the onset of nausea can include, for example, a spike in body temperature (e.g., a change in body temperature that is greater than a certain amount and/or percentage within a short period of time), body temperature rising above a predefined threshold, etc. Other factors that can be taken into account include, e.g., the ambient temperature, whether a subject is exercising (e.g., an activity state of the subject or an activity level of the user), etc., which can be detected using other sensor(s). In some embodiments, additional sensors (e.g., a thermometer or motion sensor) may be used in conjunction with a body temperature sensor (or other sensors described herein, e.g., skin conductance sensor, heart rate sensor, etc.) to determine if the changes in body temperature (or changes in other biological characteristics) are due to nausea and/or other factors. For example, a thermometer can be used to measure the ambient temperature, and data from the motion sensor, accelerometer, or other sensors can be used to determine an activity state (e.g., resting, exercising, etc.) and/or activity level (e.g., light exercise, intensive exercise) of the user. In some embodiments, data collected by additional sensors can be used to adjust a threshold or other parameter used to evaluate body temperature data to determine the onset of nausea. A processor can monitor this data, and based on the data, adjust that threshold, adjust the power being supplied to a vibratory device and/or other parameters of the vibratory device to affect the frequency, force level, etc. of the vibratory signals.

In some embodiments, a sensor (e.g., sensor 390) can be used to measure changes associated with an eye of a subject, e.g., changes in the eye pupil, movement of the eyes, and motion of the eyelids. Such biometrics can be an indicator of symptoms, including, for example, vertigo, dizziness, and sopite. For example, nystagmus, pupil dilation and constriction, and/or changes in the speed or frequency of blinking can indicate an onset of such symptoms. Accordingly, biometric indicators of the onset of such symptoms can include, for example, observing or detecting nystagmus, a sudden or fast change in pupil diameter, the pupil diameter rising above or falling below one or more predefined thresholds, an increase in the frequency of blinking, a decrease in the velocity of the eyelids opening and closing (e.g., below a predefined threshold), and/or the eyelids being closed for longer durations (e.g., longer than a predefined threshold). A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure a heart rate of a subject. Heart rate can rise and fall with the onset of nausea and other symptoms, e.g., associated with a vestibular malady or vestibulopathies. For example, when nausea first develops, heart rate can increase until a certain level, e.g., until the subject reports being six out of ten on a visual analog scale for measuring nausea. At the certain level of nausea development, however, the subject can experience a quick drop in heart rate, which may occur as a prevention to spreading toxins through the body. Accordingly, biometric indicators of the onset of nausea can include, for example, an increase or rise in heart rate (e.g., a rate of change of the heart rate that is greater than a predefined value, or an amount or percentage of change that is greater than a predefined amount or percentage), a quick drop or decrease in heart rate, etc. A processor can monitor one or more of these indicators, and based on the indicators, adjust the power being supplied to a vibratory device and/or other parameters of the vibratory device to affect the frequency, force level, etc. of the vibratory signals.

Figure 41A:
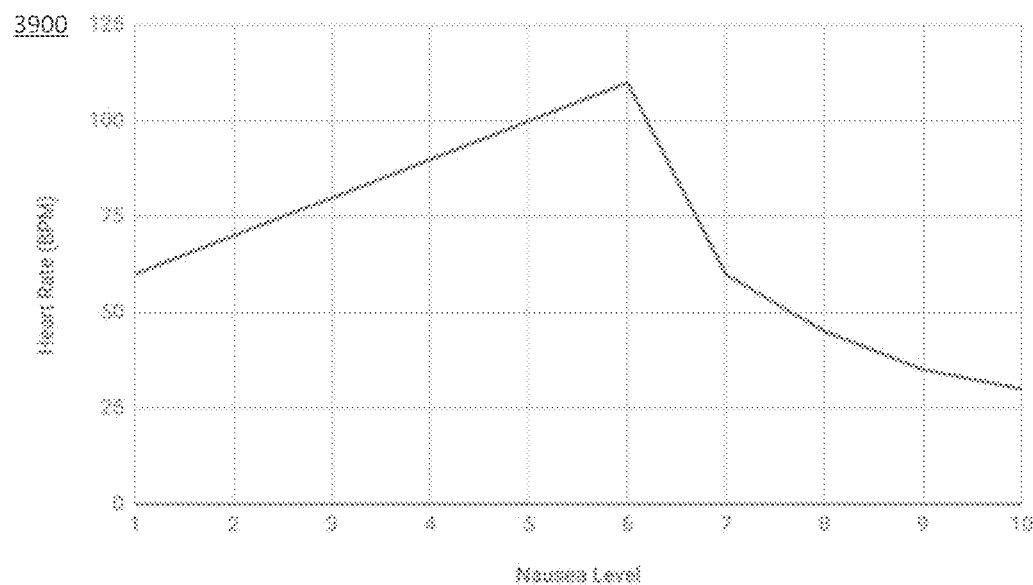
FIG. 41A is a graph of heart rate to nausea level of a subject.

FIG. 41A is a graph 3900 of heart rate as a function of nausea, showing an initial increase in heart rate with increasing nausea, and then a drop in heart rate as nausea levels continue to increase.

Figure 41B:
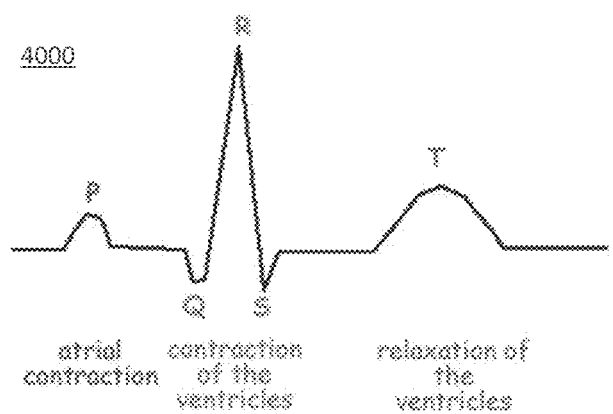
FIG. 41B is a graph of a cardiac cycle of a heart.

In some embodiments, a sensor (e.g., sensor 390), such as an EKG device, can be used to measure a heartbeat or cardiac waveform of a subject. FIG. 41B depicts an example of a heartbeat waveform 4000, with the P, Q, R, S, and T points labeled. A heartbeat waveform, e.g., the relative position between the PQRS points of a heartbeat waveform, can change with the onset of symptoms associated with various physiological conditions. Using an EKG, a heartbeat waveform of a subject can be monitored by a processor. Accordingly, biometric indicators of the onset of symptoms can include, for example, a heartbeat waveform changing or returning to baseline. A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure blood pressure. Blood pressure can vary with the onset of symptoms associated with various physiological conditions. Accordingly, biometric indicators of the onset of symptoms can include, for example, a change in blood pressure, blood pressure rising above or falling below a certain threshold, etc. A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure oxygen saturation in blood. Oxygen saturation in blood may vary with the onset of symptoms associated with various physiological conditions. Accordingly, biometric indicators of the onset of symptoms can include, for example, a fast change in oxygen saturation, oxygen saturation risings above or fallings below a certain threshold, etc. A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure nerve evoked potentials (e.g., vagal nerve monitoring). Nerve evoked potentials (e.g., vagal nerve monitoring) may vary with the onset of symptoms associated with various physiological conditions. Accordingly, biometric indicators of the onset of symptoms can include, for example, a fast change in evoked potentials, potential compound activity rising above or falling below a certain threshold, etc. A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure sweat toxicology (e.g., ethanol monitoring). Biometric indicators of the onset of symptoms can include, for example, a fast change in measured chemicals (e.g., metabolites) exuded in sweat, a specific measured chemical sweat toxicity metric rising above or falling below a certain threshold, etc. A processor can monitor one or more of these indicators, and based on the indicators, adjust the power being supplied to a vibratory device and/or other parameters of the vibratory device to affect the frequency, force level, etc. of the vibratory signals.

In some embodiments, a sensor (e.g., sensor 390) can be used to measure stress hormones (e.g., cortisol). Stress hormones (e.g., cortisol) may vary with the onset of symptoms associated with various physiological conditions. Accordingly, biometric indicators of the onset of symptoms can include, for example, a fast change in measured stress hormones exuded in the sweat, a specific measured hormone metric rising above or falling below a certain threshold, etc.

Several configurations of a vibratory device or bone conduction device enable integration of and/or coupling of one or more biometric sensors into areas where they can receive accurate or reliable data. For example, the area around the ear has been found to be effective for measuring heart rate, body temperature, and oxygen saturation. As another example, the forehead has been found to be an effective location for measuring skin conductance. Additional positions that may be beneficial to place sensors include, but are not limited to, the pinna, outer ear canal, neck, mastoid, wrist, and fingers.

Figure 42:
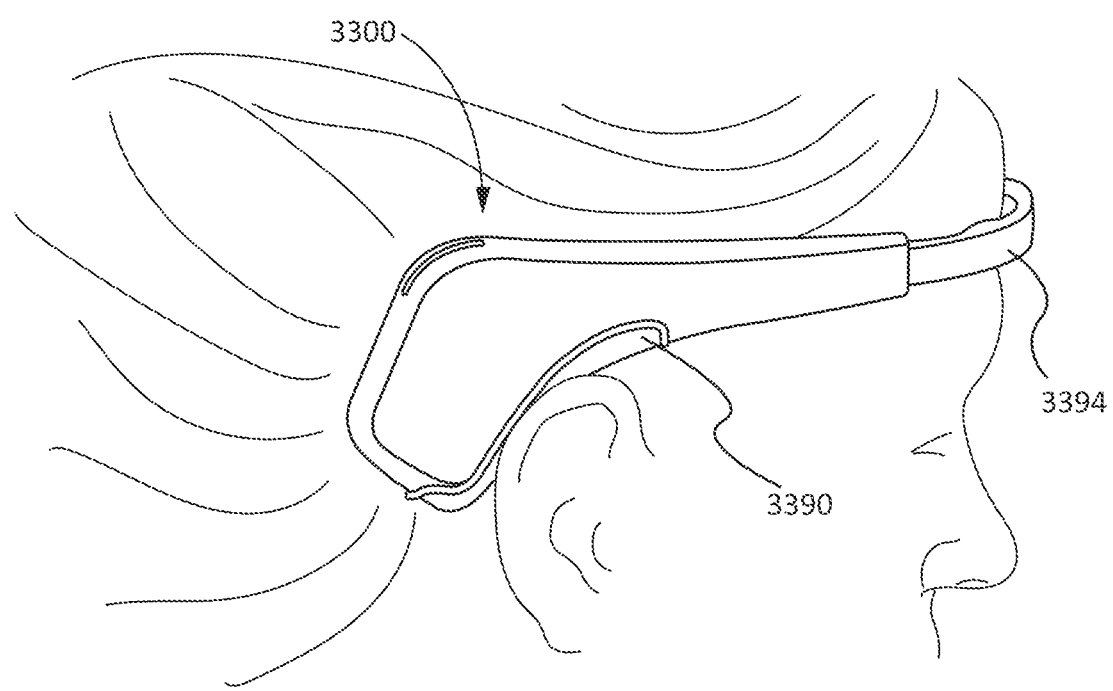
FIG. 42 is an example of a vibratory device including integrated sensors placed near an ear, ear canal, and/or a forehead of a subject, according to various embodiments.

FIG. 42 is an example vibratory device or bone conduction device 3300 with sensors 3390, 3394, placed near the ear or ear canal and on the forehead.

Figure 43:
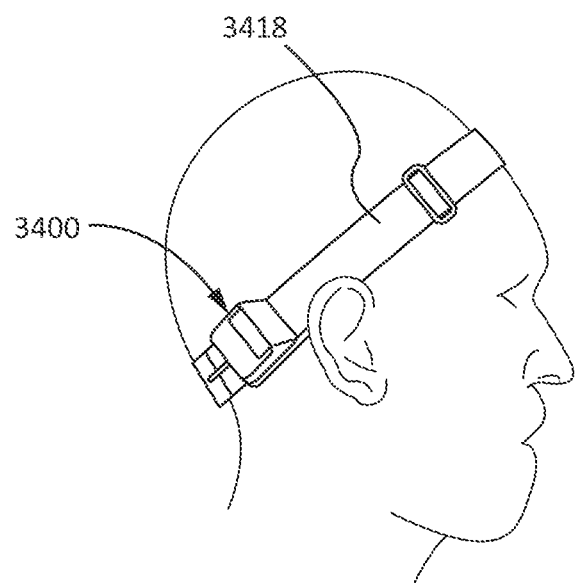
FIG. 43 is an example of a vibratory device implemented with a headband and including integrated sensors, according to various embodiments.

FIG. 43 is an example vibratory device or bone conduction device 3400 including a headband 3418, where sensor(s) can be placed around a head of a subject along the headband 3418.

Figure 44:
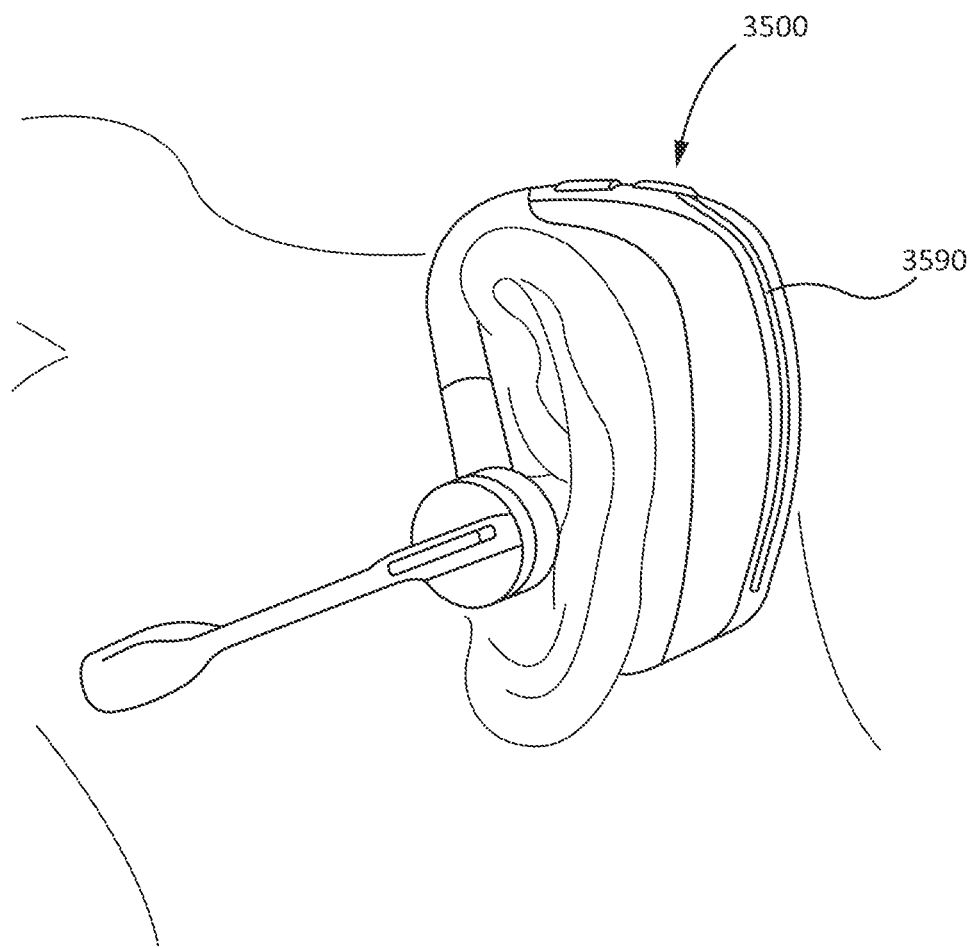
FIG. 44 is an example of a vibratory device implemented as an over-ear device and including integrated sensors, according to various embodiments.

FIG. 44 is an example vibratory device or bone conduction device 3500, where sensor(s) 3590 can be placed around an ear.

Figure 53:
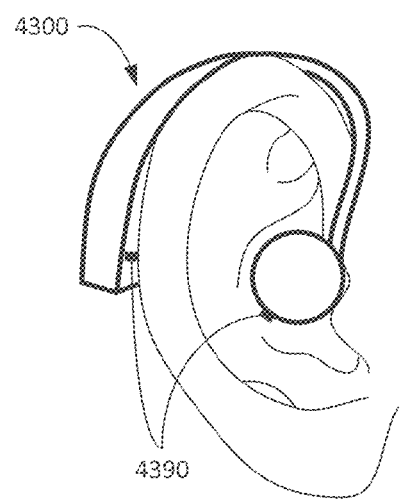
FIG. 53 is an example of a vibratory device mounted on or integrated into a hearing aid or tinnitus masker, according to various embodiments.

FIG. 53 is another example of a vibratory device 4300 mounted or integrated into a hearing aid and/or tinnitus masker. As hearing loss and tinnitus are often comorbidities with vertigo or other vestibular dysfunction, such as, for example, Meniere's disease, a device designed to provide vestibular stimulation (e.g., such as the vibratory devices described herein) can be combined with other therapeutics. In some embodiments, multiple functions (e.g., hearing aid, tinnitus masker, vestibular stimulation) can simultaneously be used and be turned on and off independent of each other. In some embodiments, one or more sensors 4390 can be mounted on or integrated into the hearing aid.

While different types of sensors are described herein for measuring different biometric and/or environmental metrics, it can be appreciate that a vibratory device can be used with several different sensors, and the data collected by those sensors can be used collectively to predict an onset and/or subset of nausea, and therefore signal to a processor to change the operation of the vibratory device.

IV. Electrical Signals for Powering Vibratory Device

Figure 17A:
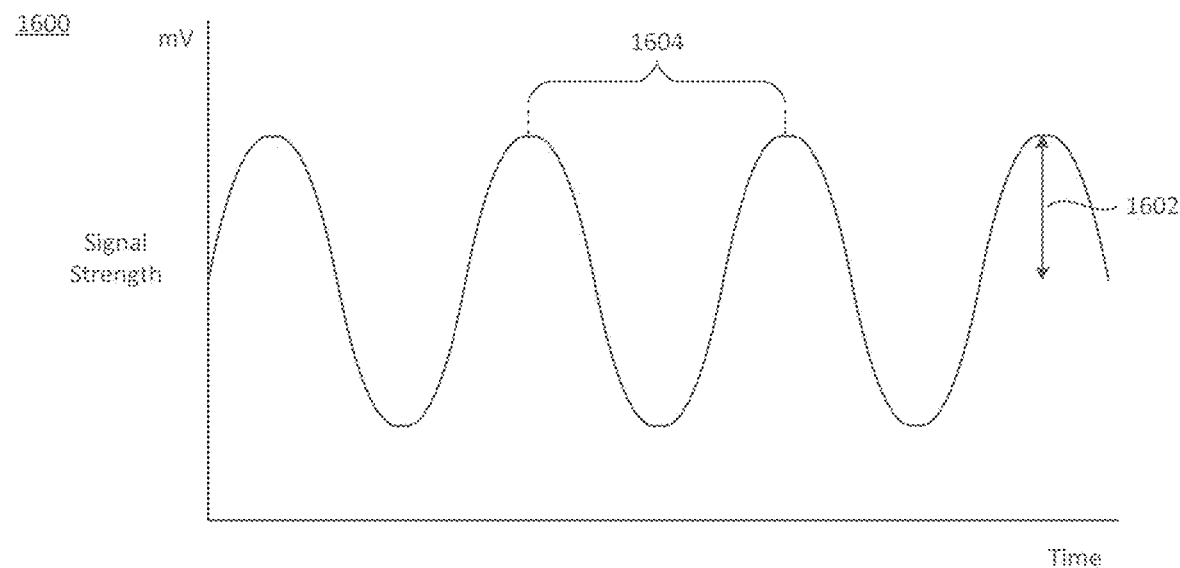
FIGS. 17A and 17B depict two example waveforms that can be used to energize a vibratory device in a system for treating symptoms associated with vestibular conditions, according to various embodiments.
Figure 17B:
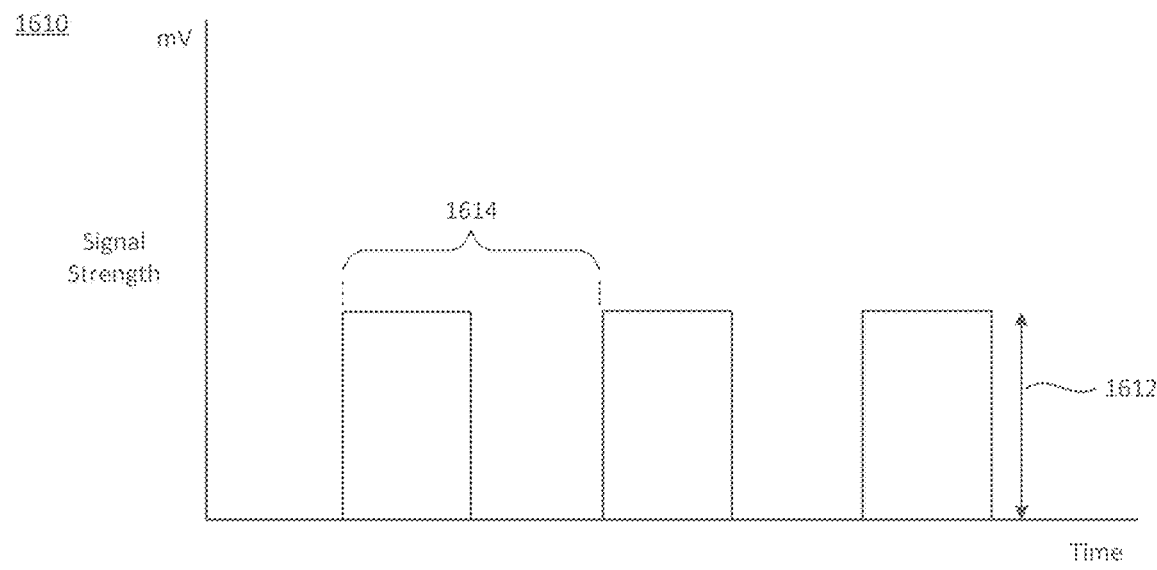

FIGS. 17A and 17B illustrate example waveforms of electrical signals for powering a vibratory device. FIG. 17A shows a sinusoidal waveform 1600, with a wavelength 1604 and an amplitude 1602, that can, for example, be used to modulate a magnetic field vector to move a vibratory element of a vibratory device. FIG. 17B illustrates a square waveform 1610 that can, for example, be used to modulate a piezoelectric vibratory element in a vibratory device to generate vibratory signals, as described above. The piezoelectric device can vibrate at a high frequency to generate pressure when activated by the square wave, and the square wave can cycle at a lower frequency (e.g., less than 200 Hz) such that the pressure cycles on and off at the lower frequency of modulation (e.g. 60 Hz), and functions similarly to a low frequency vibratory signal.

Figure 18:
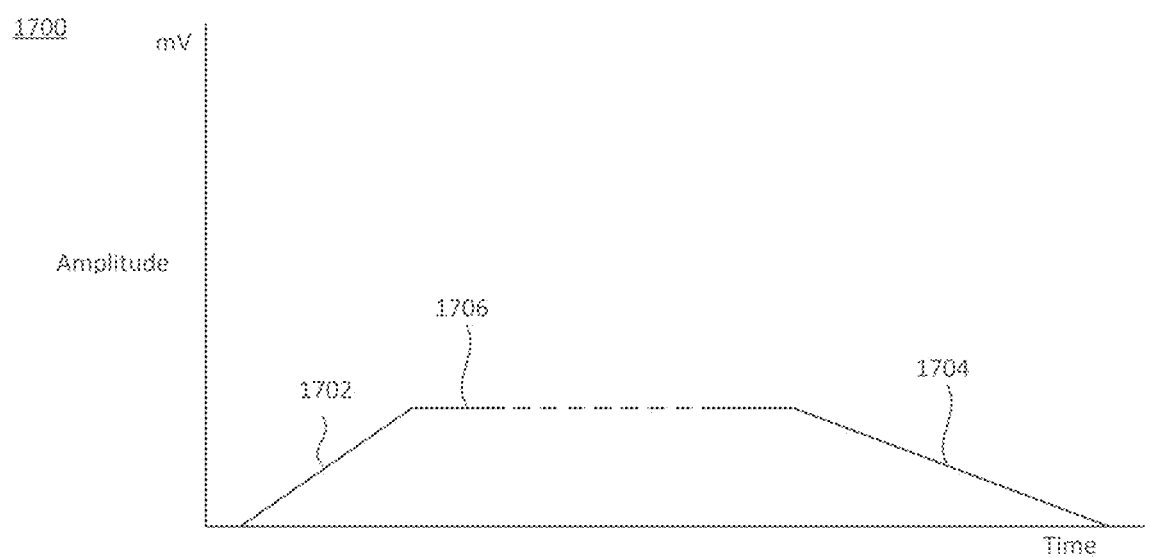
FIG. 18 illustrates an example energizing profile that can be used to energize a vibratory device in a system for treating symptoms associated with vestibular conditions, according to an embodiment.

FIG. 18 is a graph 1700 that depicts ramping up and ramping down of an electrical signal for powering a vibratory device to generate a vibratory signal. The graph 1700 shows how an amplitude of the electrical signal changes over time. As shown in FIG. 18, the amplitude can be ramped up during an onset phase 1702, where the amplitude is increased at a predefined rate. Upon reaching a predefined level, the amplitude is kept constant during a steady state phase 1706, which may last for any suitable amount of time for treating a vestibular condition (as represented by the dashed line). The amplitude can then be ramped down at a predefined rate until the signal is turned off. The onset phase 1702 and the offset phase 1704 of the waveform can have different ramp profiles, as shown in FIG. 18. For example, the increase of applied voltage amplitude in the onset phase 1702 can be a ramped increase with a certain rate of increase in amplitude per unit time. And the offset phase 1704 can be a downward ramp or a ramped decrease in amplitude, with a certain rate of reduction of amplitude per unit time that is different from that of the rate of increase. In some embodiments, the rate of increase in amplitude in the onset phase 1702 can be higher than the rate of decrease of amplitude in the offset phase 1704, as indicated by the different slopes. In some instances, the ramped increase in the onset phase 1702 and/or the ramped decrease in the offset phase 1704 can also be accomplished with a changing rate (e.g., a rate that increases and/or decreases over time).

In some instances, the rate of increase and/or the rate of decrease can be specified based the vestibular condition being treated, a subject's personal preferences, environmental factors, etc. In some embodiments, the rate of increase and/or the rate of decrease in amplitude can be adjusted by a user. In some embodiments, the rate or increase and/or the rate of decrease in amplitude can be automatically adjusted (e.g., by a control unit 360) based on sensor readings. For example, a sensor integrated into a vibratory device can be configured to measure bodily or physiological conditions and/or reactions (e.g., changes in perspiration, temperature, heart rate, etc.) as the vibratory device is powering on and/or powering off. By monitoring bodily conditions and/or reactions, a ramp up and/or ramp down rate can be adjusted to accommodate different reactions (e.g., by a more sensitive or first-time user vs. a more regular user of the device). Moreover, for subjects that suffer from a chronic condition (e.g., vertigo, tinnitus), the ramp up and/or ramp down can be selected to reduce jarring effects of transitioning between the device turning on and/or off, such as, for example, a sudden return of the vestibular condition and greater on-set of symptoms associated with the vestibular condition.

V. Methods

Figure 19:
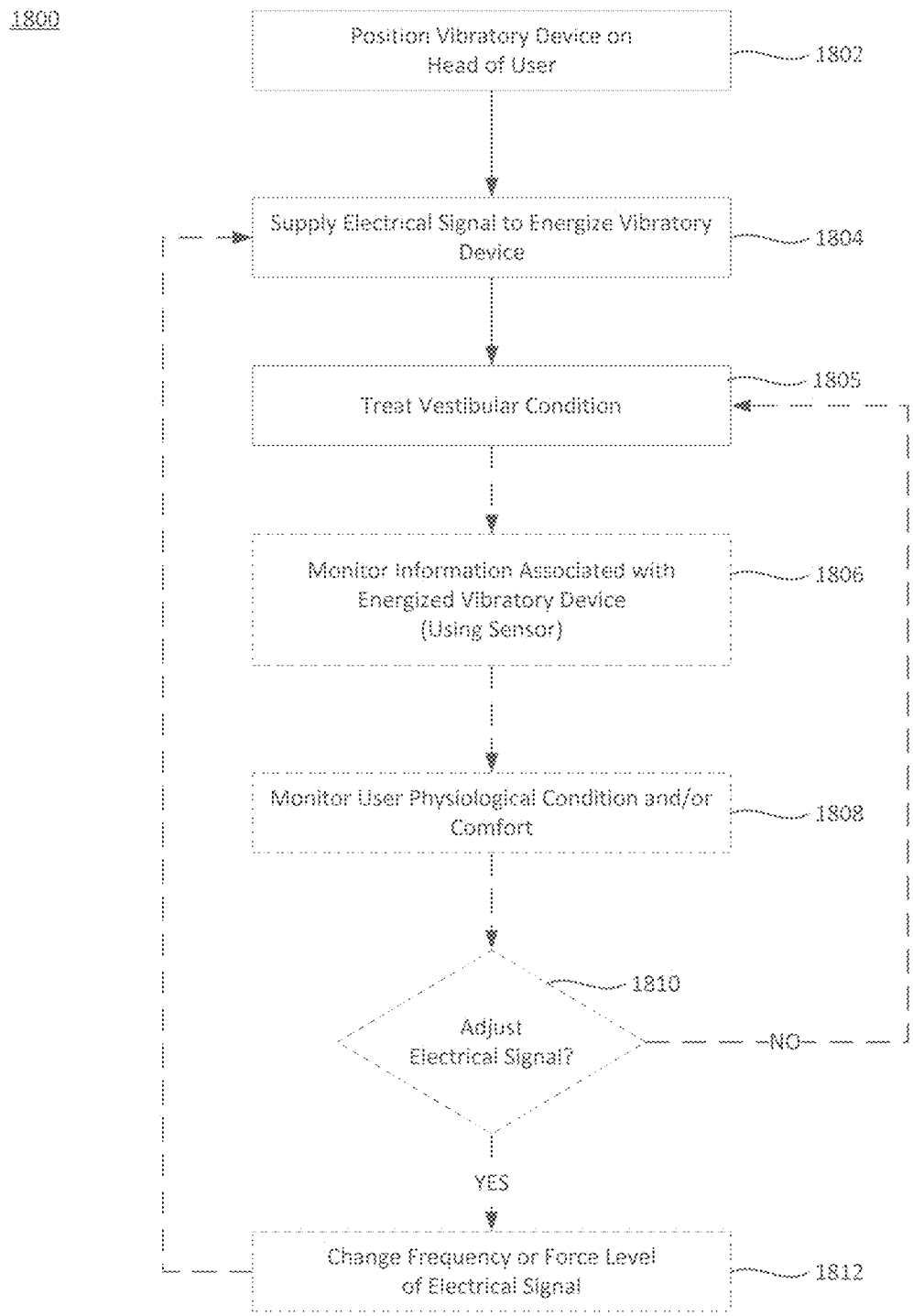
FIG. 19 is a flowchart of an example method for using a vibratory device to treat symptoms associated with vestibular conditions.

FIG. 19 illustrates a method 1800 for using a vibratory device (e.g., vibratory device 300, 400, 500, 600, 700, etc.) to treat symptoms associated with vestibular conditions disclosed herein. At 1802, the vibratory device is positioned on the head of the subject or user. The positioning is over a suitable area (e.g. over a suitable bone structure) such that vibratory signals can be effectively transferred to the vestibular system of the subject.

At 1804, an electrical signal is supplied to the vibratory device to energize the device and cause movement of the vibratory element in the vibratory device. At 1805, the vibratory signals are applied to the subject's head to treat the vestibular condition. At 1806, information associated with the energized vibratory device is monitored, including, for example, current, voltage, magnetic field fluctuations, etc. At 1808, physiological conditions and/or comfort level of the subject is monitored. For example, the physiological signs like heart rate, perspiration, temperature, breathing, oxygen saturation, etc, of the subject can be monitored. In some instances, any feedback from the subject such as feedback reporting a level of comfort or discomfort perceived by the user, can be monitored using appropriate sensors and actuators integrated with the vibratory device. Such monitoring at 1806 and 1808 can be accomplished using one or more sensor(s) (e.g., sensor 390, sensor 416), and/or a control unit (e.g., control unit 360).

At 1810, the vibratory device and/or a control unit coupled to the vibratory device determines whether the electrical signal should be adjusted or changed. If the electrical signal does not need to be adjusted (1810: NO), then the vibratory device can continue treating the vestibular condition, at 1805, with continued monitoring of information associated with the vibratory device, at 1806, and continued monitoring of information associated with the subject, at 1808, as described above.

When the electrical signal does need to be adjusted (1810: YES), at 1812, a frequency or a force level of the electrical signal is changed and the new electrical signal is applied to the vibratory device, at 1804, following the flow chart as described above. The information collected from monitoring the vibratory device and from monitoring the subject can be used to determine whether the force level and/or the frequency need to be changed and by how much and in what form. For example, if measured voltage, current, and/or magnetic field fluctuations indicate that the current frequency is not the resonant frequency, then the frequency may be adjusted to improve an efficiency of the vibratory device. As another example, if a signal is received from a user indicating that the vestibular condition is no longer present (e.g., motion sickness is no longer present), then the vibratory device may adjust the frequency to turn off the device (e.g., via a ramp down). As another example, in response to an indication of discomfort by the subject, the force level may be decreased.

Figure 45:
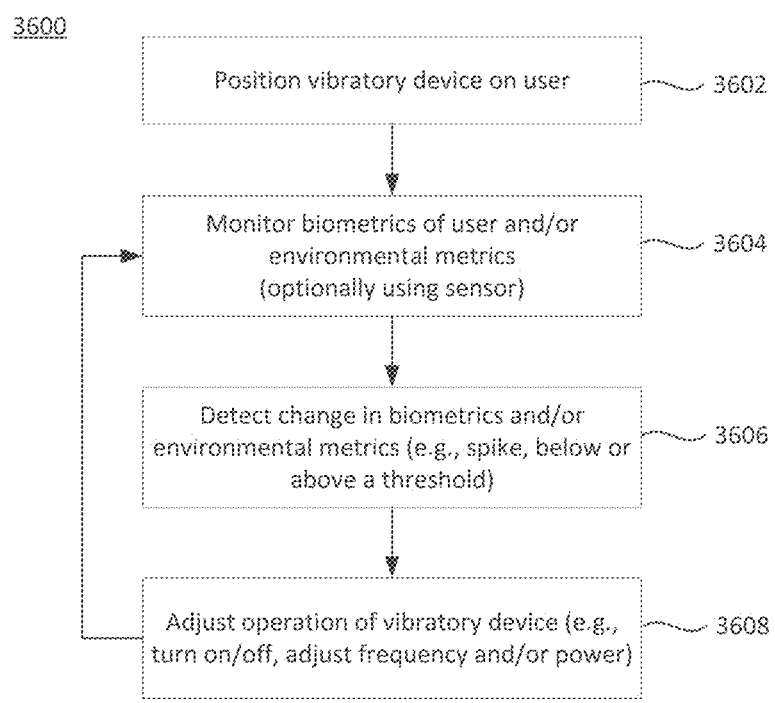
FIG. 45 is a flowchart of an example method for operating a vibratory device with a sensor, according to various embodiments.

FIG. 45 illustrates a method 3600 that can be performed by one or more components associated with a vibratory device (e.g., any of the vibratory devices described herein, including one or more sensors). At 3602, the vibratory device can be positioned on a user or subject, e.g., a head or ear of the user. The positioning can be over a suitable area (e.g. over a suitable bone structure) such that vibratory signals can be effectively transferred to a target area (e.g., a vestibular system).

At 3604, an onboard or external processor or control unit (e.g., control unit 360) can monitor biometrics of the user and/or environmental metrics, e.g., collected by one or more sensor(s) (e.g., sensor(s) 390). The one or more sensors can be integrated into and/or operatively coupled to the vibratory device. At 3606, the processor can detect a change in the biometrics and/or environmental factors, such as, for example, a spike in the data, the data falling above and/or below one or more thresholds, etc., as described above. Based on the monitoring and detecting, the processor can adjust an operation of the vibratory device (e.g., turn on or off the vibratory device; adjust a frequency, force level, or power of the vibratory signals produced by the vibratory device and/or signal used to active the vibratory device; etc.).

VI. Experimental Studies

Experimental studies were conducted to test an experimental vibratory device, similar to example vibratory devices disclosed herein, for treating symptoms associated with vestibular conditions. The experimental vibratory device included a vibratory element implemented as a magnet suspended between two other magnets, similar to the vibratory device 500 depicted in FIG. 6. The vibratory device included an outer coil with an impedance of four ohm, which was energized by a microcontroller, a custom-designed Arduino board. The microcontroller could energize the outer coil to generate a magnetic field, which was used to vibrate the suspended magnet. The three-magnet/voice coil assembly was placed inside a body or housing, and was connected to and powered by a rechargeable battery. The vibratory device could be coupled to a human head, and was capable of generating vibrations that could be conducted via bone to a vestibular system.

In the studies, subjects wore the experimental vibratory device placed behind an ear against an area overlaying the mastoid bone, such that vibratory signals generated by the device could be conducted via bone to the subjects' vestibular systems. Subjects were subjected to various condition to induce motion sickness, nausea, and/or other vestibular conditions, and the effects of the vibratory devices were evaluated based on information reported by subjects.

For the experiments, the force level of the vibrations produced by the vibratory device was measured with a calibrated Brüel & Kjær (B&K) artificial mastoid (No. 4930) coupled with a B&K sound level meter (No. 2234). The vibratory device was inserted in a holder in the B&K, artificial mastoid designed for holding a bone conduction hearing aid. A force of between 3.5 to 8 Newtons was applied on top of the vibrating device, which sat against the B&K artificial mastoid. Bone conduction levels were quantified with the B&K sound level meter and are expressed as dB re 1 dyne (i.e., a force level).

Further information regarding each of the studies are provided below.

Experimental Study I

Figure 20A:
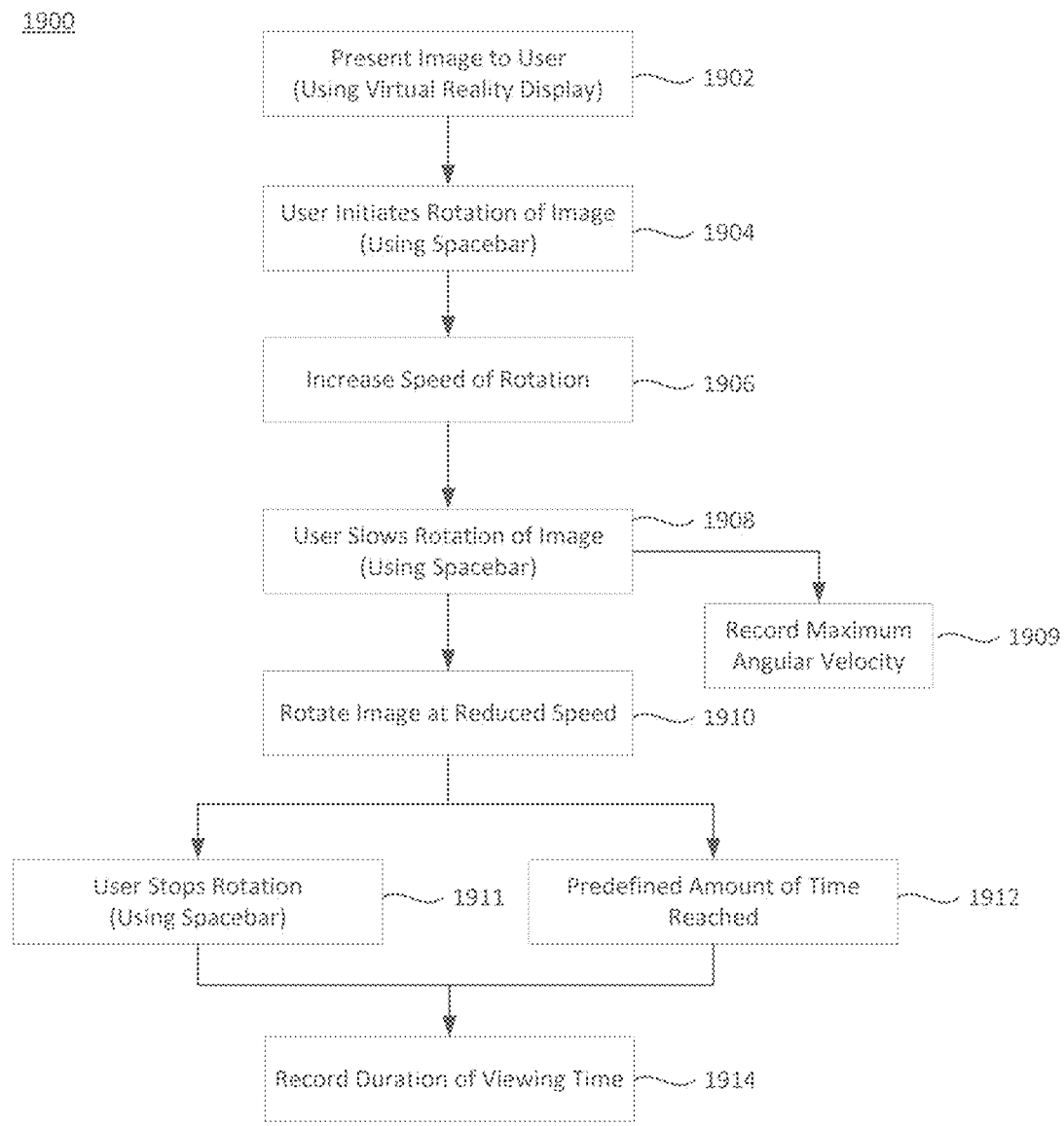
FIG. 20A is a flowchart of a procedure of a study that was conducted to test a vibratory device for treating symptoms associated with vestibular conditions.

FIG. 20A depicts a flowchart 1900 of a procedure for a first experimental study. Study participants in this first experimental study did not suffer from a history of vestibular maladies, including dizziness. During the duration of the study, participants were seated in an office chair and asked to wear the Oculus Rift DK2 virtual reality system and a vibratory device, according to the example design described above. The vibratory device was held in place with a head strap.

The study was conducted according to the test procedure outlined in FIG. 20A. Each participant went through the test procedure multiple times, first with the vibratory device turned off and then with the vibratory device turned on. During the tests with the vibratory device turned on, the frequency and/or the force level of the vibratory device was varied to test whether particular frequencies and/or force levels would be more effective at treating vestibular conditions associated with using a virtual reality device. During the tests, the order of the frequencies and/or force levels was randomized between participants. Participants were also given the opportunity to pause the study at any time to recover from dizziness or other vestibular conditions caused by the use of the virtual reality device.

Figure 20B:
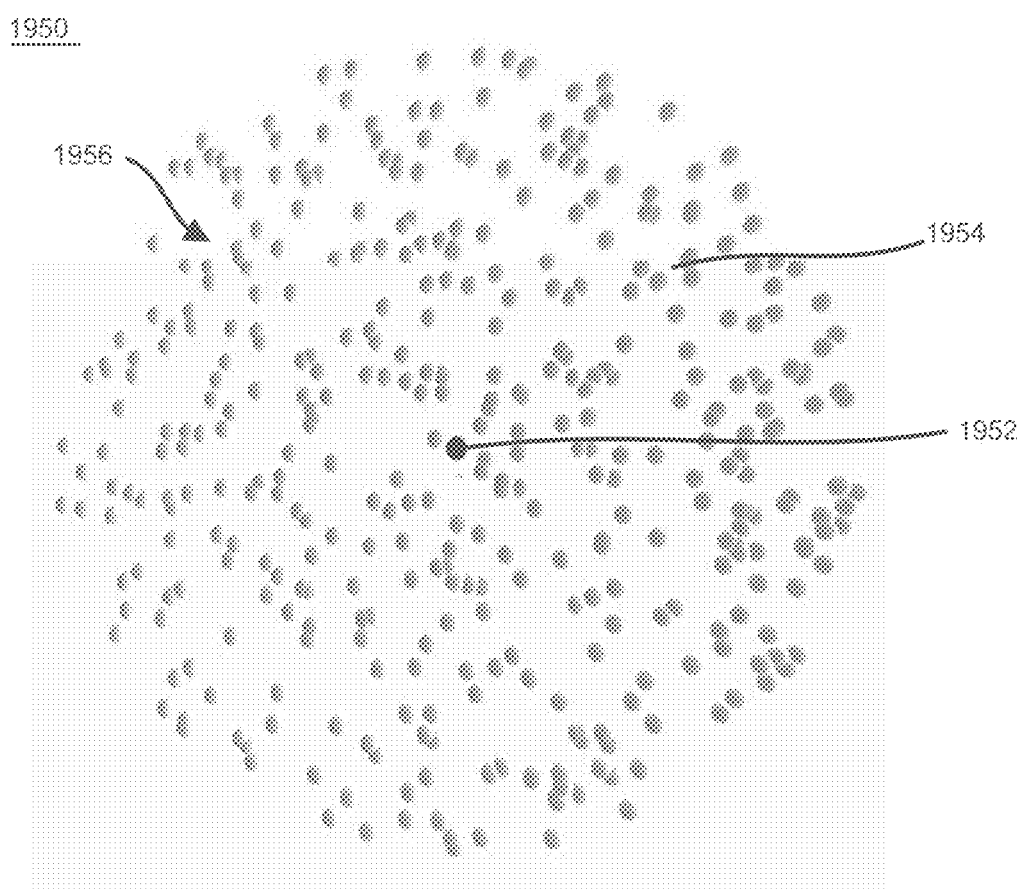
FIG. 20B is a schematic illustration of a static view of an example visual stimulus used in the procedure depicted in FIG. 20A to test the vibratory device.

At 1902, the participant is presented with the visual stimulus 1950 depicted in FIG. 20B via the display of the virtual reality device. The visual stimulus 1950 includes a disc-shaped region 1956 with a plurality of spheres 1954. Participants were instructed to focus their attention on a central sphere 1952 that was of a different hue than the rest of the spheres 1954 in the disc-shaped region 1956. The disc-shaped region 1956 was designed to represent a three-dimensional space that may be viewed using a virtual reality device, such as the Oculus Rift.

At 1904, the participant initiates a rotation of the spheres 1954 in the disc-shaped region 1956 about a central point (i.e., the central sphere 1952) by pressing a spacebar on a keyboard. Upon pressing the spacebar, the spheres 1954 would begin to spin, gradually accelerating at a rate of 4 degrees/second/second, at 1906. Participants were instructed to press the spacebar again when they felt discomfort or dizziness, at which point the angular velocity of the spinning spheres 1954 would be recorded and stored as the "maximum angular velocity" for that participant, at 1908 and 1909. If a particular participant did not press the spacebar to indicate discomfort or dizziness, then the angular velocity of the spheres 1954 would increase until it reached a predefined angular velocity of 90 degrees/second.

At 1910, the angular speed of the image would be reduced to 90% of the speed before the user's indication (i.e., 90% of the speed recorded as the "maximum angular velocity") or, when the participant did not press the spacebar, 90% of 90 degrees/second (i.e., 81 degrees/second). The spheres 1954 are rotated at the reduced speed until the participant presses the spacebar again to indicate a return of discomfort or dizziness, at 1911, or until a predefined amount of time (e.g., 120 seconds) has passed, at 1912. Upon either the participant's indication, at 1911, or the predefined amount of time passing, at 1912, the time that the participant has viewed the disc-shaped region 1956 at the reduced speed is recorded as the "Duration of Viewing Time."

For a given participant, the participant was asked to perform the test procedure first with the vibratory device turned off. The participant would undergo the test procedure two times, a first time with the spheres 1954 rotating in a clockwise direction and a second time with the spheres 1954 rotating in a counterclockwise direction. The same would then be repeated with the vibratory device turned on. Study participants were asked to wear the vibratory device behind their ears and level with the ear canal on a flat part of the mastoid bone. Participants were given time to rest between the clockwise and counterclockwise tests (e.g. 10-60 seconds), as needed, to recover from any discomfort or dizziness.

Participants while using the vibratory device were asked to test either a set of different force levels or a set of different frequencies. For participants that tested different force levels, the frequency of the vibratory signals was kept constant (i.e., at 50 Hz), while the force level was set to 87, 92, 94, 96, 98, 99, 100, and 101 dB re 1 dyne. For participants that tested different frequencies, the power level of the vibratory signals was set to a constant level (i.e., 96.5 dB re 1 dyne) and the frequency was varied between 30 and 75 Hz.

Eighteen participants participated in the study. Approximately one third of these participants who volunteered for the study did not experience any motion sickness from the experiments. These participants watched the visual stimulus that was presented (FIG. 20B) until the spinning spheres 1954 reached 90 degrees/second, and then continued watching the visual stimulus for 120 seconds at a reduced speed. These motion-sickness-resistant participants were instructed to repeat their exposure to the visual stimulus with the vibratory device turned on to test whether vibrations from the device would induce motion sickness. None of these participants reported that they experienced any negative side effects during and after using the vibratory device with the vibrations produced by the vibratory device being set to 97 dB re 1 dyne or below.

The experimental data for the remaining eleven participants (i.e., those that indicated that they experienced motion sickness or dizziness at some point during the experimental study) is depicted in FIGS. 21A, 21B, 22A, and 22B. For the data points in the graphs depicted in FIGS. 21A, 21B, 22A, and 22B, the clockwise and counterclockwise "Maximum Angular Velocity" and "Duration of Viewing Time" were averaged for each participant under each test condition, and the "with vibratory device" data was baseline-normalized based on the "without vibratory device" data (i.e., data collected for a participant while using the vibratory device set to a particular frequency and/or force level was normalized based on that participant's data while not using the vibratory device). After calculating these ratios for each participant, the ratios of the eleven participants were averaged to arrive at the data point depicted in the graphs shown in FIGS. 21A, 21B, 22A, and 22B.

Figure 21A:
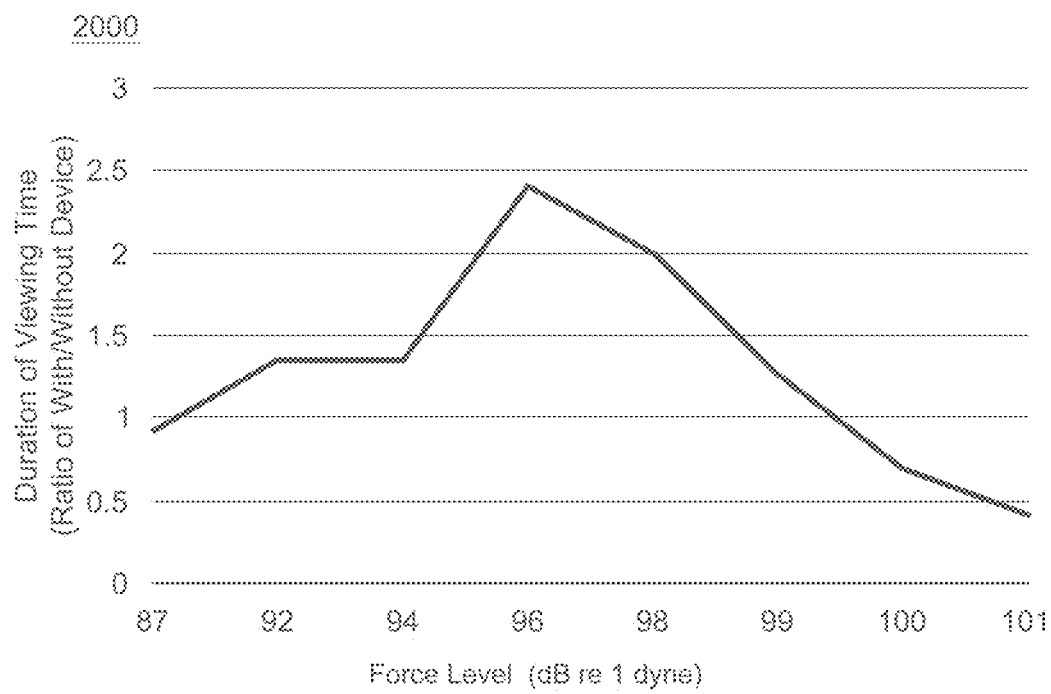
FIGS. 21A and 21B depict results from the study procedure depicted in FIG. 20A for testing the vibratory device at different force levels.
Figure 21B:
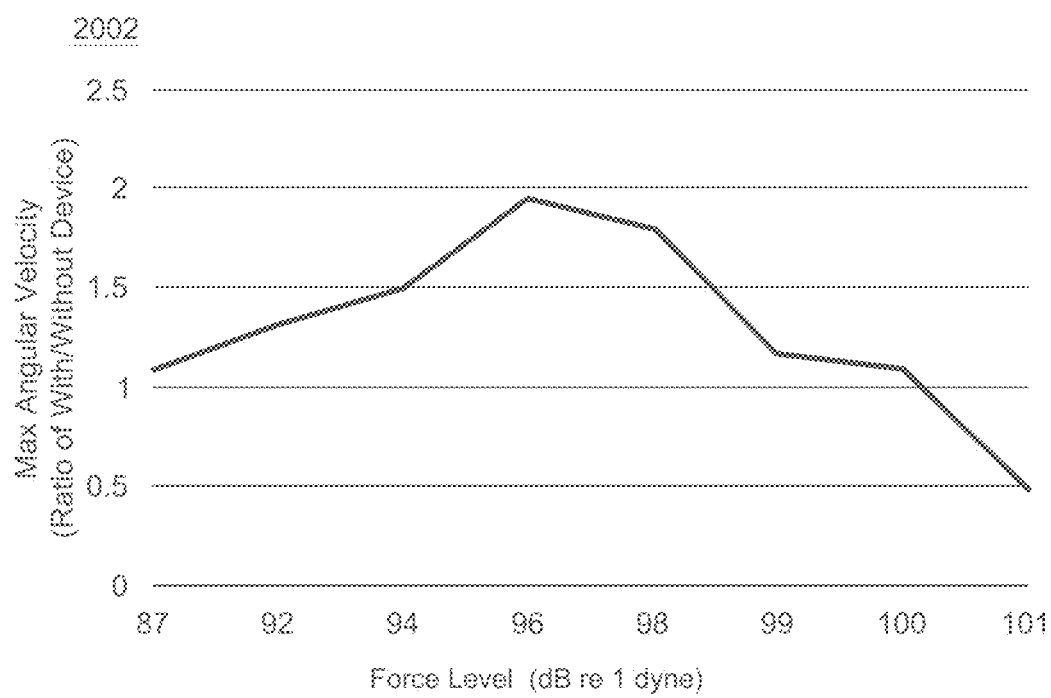

FIG. 21A depicts a graph 2000 of the average "Duration of Viewing Time" ratios of the eleven participants across a range of different force levels. Values greater than one indicate an increase in an amount of viewing time before discomfort is experienced while using the vibratory device versus not using the vibratory device. FIG. 21B shows a graph 2002 of the average "Maximum Angular Velocity" ratios of the eleven participants across a range of different force levels. Values greater than one in FIG. 21B indicate an increase in angular velocity that did not cause discomfort while using the vibratory device versus not using the vibratory device. The experimental data showed that for the eleven participants, the vibratory device had a greatest effect when the force level of its vibrations were set to 96 dB re 1 dyne. Based on an interpolated fit of the data, the "Duration of Viewing Time" and "Maximum Angular Velocity" ratios peaked at 96.5 dB re 1 dyne. "Duration of Viewing Time" and "Maximum Angular Velocity" ratios at force levels ranging from 93 dB to 98 dB were statistically significant different from and greater than one, indicating that a vibratory device set to these force levels would be effective at treating a vestibular condition.

At 87 dB re 1 dyne, the ratios were not statistically different from one, indicating that the device would not be effective at treating a vestibular condition. At levels around or above 100 dB re 1 dyne, many participants reported feeling worse with the vibratory device turned on. While the threshold of discomfort at these higher force levels was slightly different among participants, with some reporting discomfort at levels as low as 99 dB, once that threshold was reached for a particular participant, the participant would report that the vibrations made them feel uncomfortable almost immediately. Participants tested at 102 dB all reported feelings of discomfort, regardless of whether they were using the virtual reality system as the vibrations from the vibratory device alone caused them discomfort.

Figure 22A:
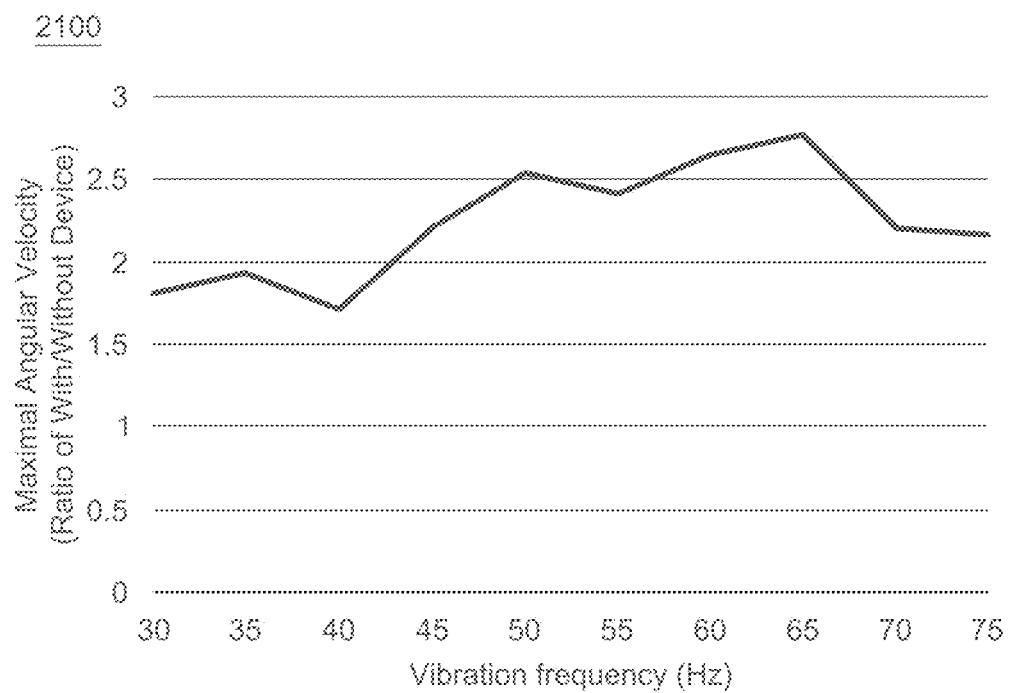
FIGS. 22A and 22B depict results from the study procedure depicted in FIG. 20A for testing a vibratory device at different frequencies.
Figure 22B:
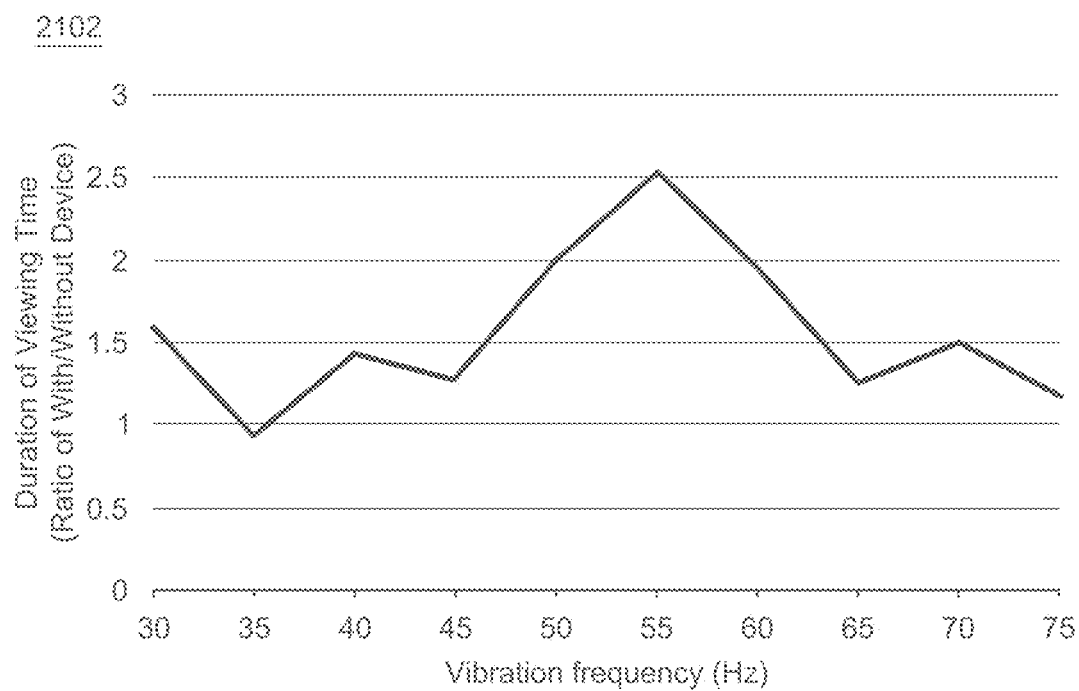

FIGS. 22A and 22B depict normalized and averaged "Duration of Viewing Time" and "Maximum Angular Velocity" ratios for the eleven participants across a range of frequencies. As shown, these results indicated that the effectiveness of the experimental vibratory device at mitigating or delaying the onset of virtual reality sickness does not appear to be dependent on the frequency of the vibratory signals. Nonetheless, the graphs 2100 and 2102 show greater ratio values from 45 to 65 Hz.

Certain factors may have limited the results of this first experimental study. For example, the angular velocity of the spheres 1954 in the disc-shaped region 1956 was limited by the visual display system. Specifically, the refresh rate of the Oculus DK2 screen is 90 Hz. The panels of the device are organic LED (OLED), with a persistence of 2 milliseconds. These factors prevented the rotational speed of the spheres 1954 in the disc-shaped region 1956 from rotating beyond approximately 90 degrees/second. As the rotational speed was increased beyond 90 degrees/second, the virtual reality display would start to flicker. Many test participants reached this upper limit while wearing the vibratory device, which caused a ceiling effect in the measurements.

Similarly, while viewing the spinning spheres 1954 at the reduced speed, several subjects complained of eyestrain, with no complaints of discomfort or nausea. Thus, participants were also limited in how long they could watch a rotating disk, which was another factor that led to a ceiling effect in the measurement of the effectiveness of the experimental vibratory in delaying the onset of virtual reality sickness.

Taking these factors into account, this first experimental study showed that the vibratory device was effective at treating virtual reality sickness at statistically significant levels. From the data shown in the graphs in FIGS. 20A and 20B, it was shown that variations in force level would have a statistically significant effect on the effectiveness of the vibratory device. Specifically, it was shown that force levels below 93 dB re 1 dyne were not as effective at treating vestibular conditions and that force levels above 100 dB caused discomfort and dizziness in certain patients that worsened vestibular conditions; therefore, the data indicated that force levels between 93 dB and 98 dB re 1 dyne were more effective at treating vestibular conditions. On the other hand, the data shown in the graphs in FIGS. 21A and 21B showed that varying vibration frequency had a smaller effect on the effectiveness of the vibratory device at treating vestibular conditions, as the effectiveness of the vibratory device did not have a clear trend or peak between 45 Hz to 65 Hz.

Experimental Study II

In a second experimental study, using the results obtained from the first experimental study, disclosed above, the effectiveness of the experimental vibratory device at mitigating or preventing motion sickness experienced by users of the virtual reality game "EVE: Valkyrie" was measured.

"EVE: Valkyrie" is a first-person spaceship shooter game in which a player moves around a field of spaceships and space rocks using an Xbox 360 handheld controller. The game has been known to induce motion sickness in many players. The game involves flying through "gates" placed in a field of asteroids and spaceships. In addition to movement in the three spatial dimensions, most "gates" require the player to rotate around a three-dimensional rotational axis (e.g., a "roll," "pitch," or "yaw" axis).

In this study, subjects played the virtual reality game "EVE: Valkyrie" for up to fifteen minutes, using an Oculus Rift CV1 system. For the study, participants were instructed to play the game in two sessions, on two consecutive days, with and without using the experimental vibratory device described above. On the first day of experiments, participants were asked to play a training mission portion of virtual reality game for up to fifteen minutes without using the experimental vibratory device. Participants were instructed to stop if they began to feel nauseated before the end point of fifteen minutes. Experienced gamers could choose to go directly to the mission, bypassing the training mission and launching directly into a virtual reality space fight. On the second day, the same experimental procedures were followed, but with participants wearing the experimental vibratory device, which was set to a frequency of 60 Hz and a force level of 96.5 dB, which were found to be effective per the results of the first experimental study. The device was applied to the skull, behind the right ear and level with the ear canal and onto the flat part of the mastoid, with an applied force of approximately 3.5 to 8 Newtons. During the study, any participant who felt dizzy or uncomfortable could stop at any time of their choosing.

Participants were asked to fill out a Motion Sickness Assessment Questionnaire ("MSAQ"), approximately ten minutes after they stopped playing the game. The MSAQ involves sixteen statements or manifestations that help identify and categorize independent descriptors of motion sickness by grouping them into four categories of motion sickness: (1) gastrointestinal, (2) central, (3) peripheral, and (4) sopite. MSAQ scores range from 1 (not at all) to 9 (severe) for the sixteen possible manifestations of motion sickness. Table 1 shows the sixteen statements of the MSAQ used to assess motion sickness experienced by the participants.

TABLE 1

Motion Sickness Assessment Questionnaire, administered ten minutes after the end of the Oculus Rift playing experience described in Experimental Study II. MSAQ results, without and with device respectively

| | | |
|---|---|---|
| 1. I felt sick to my stomach (G) | 2.9 ± 0.6 | 1.3 ± 0.2 |
| 2. I felt faint-like (C) | 2.7 ± 0.4 | 1.2 ± 0.1 |
| 3. I felt annoyed/irritated (S) | 2.7 ± 0.4 | 1.4 ± 0.2 |
| 4. I felt sweaty (P) | 3.2 ± 0.6 | 1.6 ± 0.2 |
| 5. I felt queasy (G) | 3.1 ± 0.5 | 1.6 ± 0.3 |
| 6. I felt lightheaded (C) | 4.7 ± 0.6 | 1.6 ± 0.2 |
| 7. I felt drowsy (S) | 3.5 ± 0.6 | 1.4 ± 0.2 |
| 8. I felt clammy/cold sweat (P) | 2.5 ± 0.5 | 1.08 ± 0.08 |
| 9. I felt disoriented (Q) | 3.5 ± 0.5 | 1.5 ± 0.6 |
| 10. I felt tired/fatigued (S) | 3.8 ± 0.6 | 1.3 ± 0.1 |
| 11. I felt nauseated (G) | 3.3 ± 0.6 | 1.5 ± 0.2 |
| 12. I felt hot/warm (P) | 3.8 ± 0.7 | 1.4 ± 0.2 |
| 13. I felt dizzy (C) | 4.1 ± 0.7 | 1.7 ± 0.2 |
| 14. I felt like I was spinning (C) | 3.1 ± 0.5 | 1.25 ± 0.1 |
| 15. I felt as if I may vomit (G) | 1.9 ± 0.4 | 1.0 ± 0.0 |
| 16. I felt uneasy (S) | 3.3 ± 0.6 | 1.5 ± 0.2 |

Not at all      Severely
1—2—3—4—5—6—7—8—9
G: Gastrointestinal C: Central
P: Peripheral S: Sopite-related When participants were asked to engage in play for fifteen minutes without wearing the experimental vibratory device on the first day, eleven of the seventeen participants were able to play for the full fifteen minutes. The duration of play for the remaining six ranged from 4:05-14:50 minutes. The average playing time was 13:25 minutes. By contrast, when participants wore the experimental vibratory device while playing, all 17 participants were able to engage in play for the duration of 15 minutes. Data from the MSAQ was collected and is presented in Table 1. The scores in the MSAQ range from 1 (not at all) to 9 (severe).

Figure 23A:
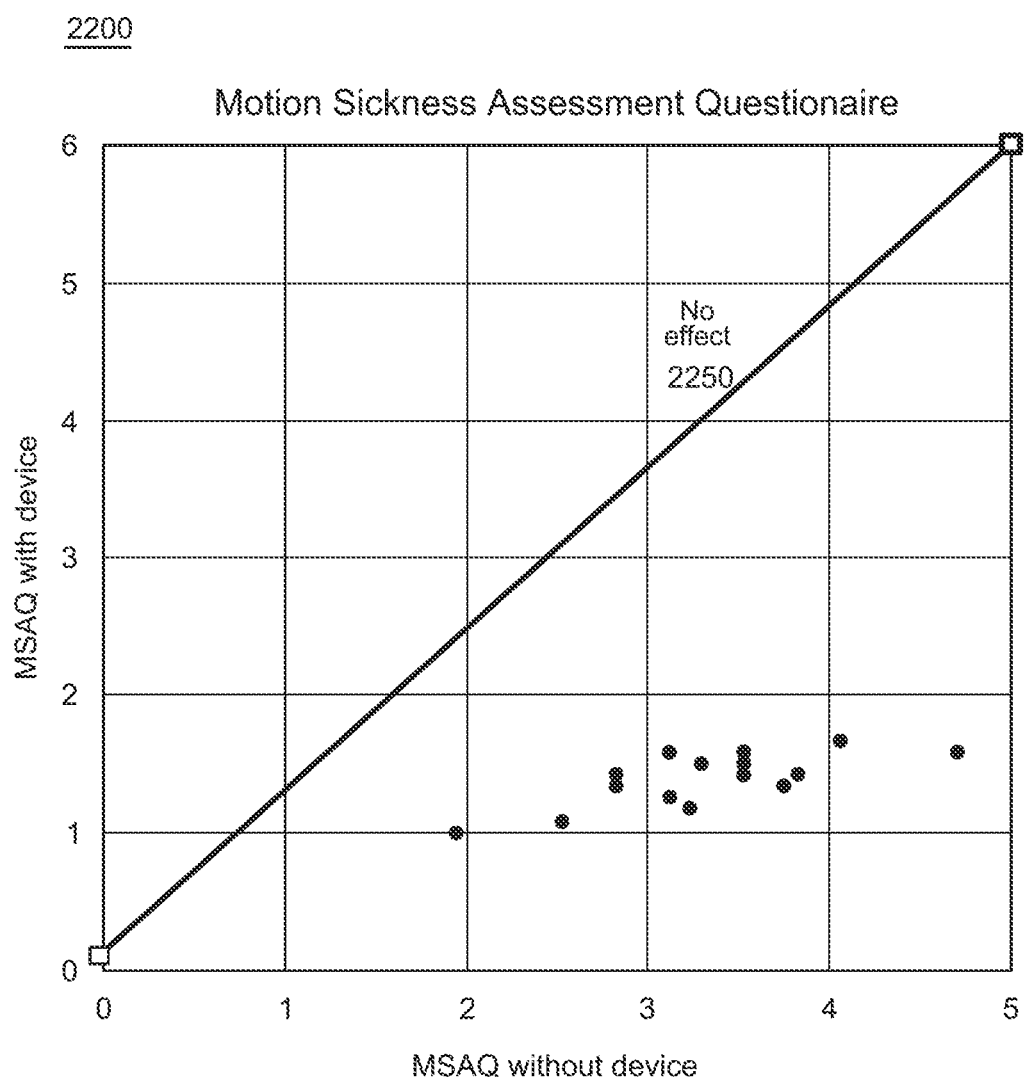
FIGS. 23A and 23B depict data associated with a questionnaire completed by subjects of a study conducted to test a vibratory device for treating symptoms associated with vestibular conditions, using a test procedure, in yet another instance.
Figure 23B:
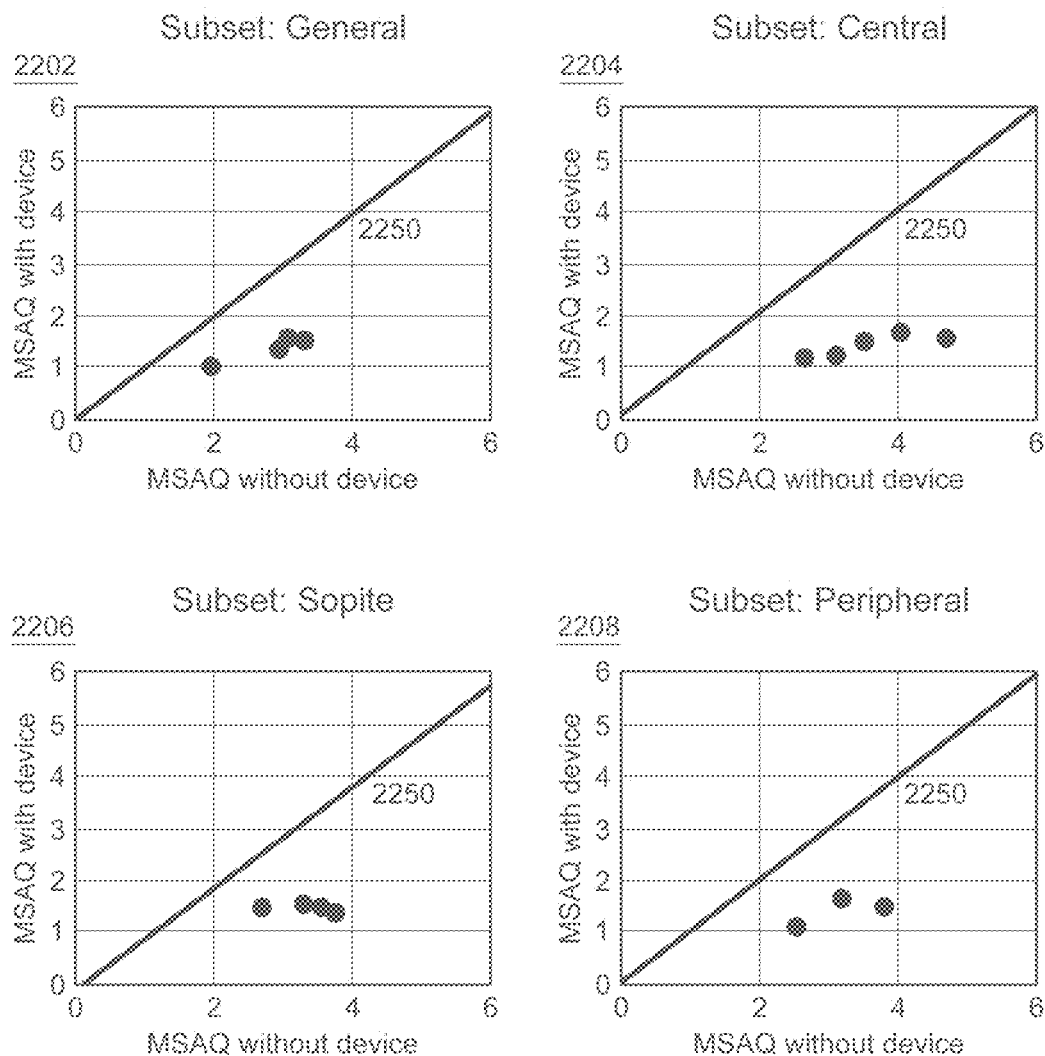

The results of the MSAQ are presented in graphical form in FIGS. 23A and 23B. Each graph depicts a ratio of the MSAQ scores obtained while not wearing the device over the MSAQ scored obtained while wearing the device. FIG. 23A depicts a plot 2200 that shows the mean scores from the MSAQ across all four categories of motion sickness, and FIG. 23B depicts four subplots 2202, 2204, 2206, 2208 that show the scores for the four categories of motion sickness defined by the MSAQ—specifically, (1) gastrointestinal, (2) central, (3) peripheral, and (4) sopite, respectively. The line 2250 through each graph represents when the MSAQ scores with and without using the vibratory device are the same, and therefore is the line that represents when the vibratory device has no effect on motion sickness.

As depicted in FIGS. 23A and 23B, the data indicates that the vibratory device was effective at treating motion sickness, as all the data points were situated below the line 2250. The data points indicated a significant reduction in the MSAQ score from 9 (severe) to 1 (not at all). Even when broken into the different categories of motion sickness, as shown in plots 2202, 2204, 2206, 2208 in FIG. 23B, the vibratory device was significantly effective in each category at treating motion sickness.

Experimental Study III

In a third experimental study, participants were asked to be rear seat passengers in a four-door sedan and were driven on a segment of road based on a fixed 20-minute itinerary. Three road tests were conducted on the same day, on this set route. During each drive, the participants were asked to read an article on their smartphone or other small handheld device. The start time was recorded, and each participant reported the time at which they first felt first symptoms of motion sickness.

With each participant, a baseline measurement of motion sickness was established by having the participant undergo the drive and read an article on his or her smartphone without wearing any type of assistive device. After the initial drive, each participant was asked to wear (1) the experimental vibratory device as described herein placed overlaying the participant's right mastoid bone, or (2) a sound generator that faced outwards and was isolated from a participant's head by a rubber pad and that emitted a low frequency tone that provided an auditory level equivalent to the experimental vibratory device. The order of wearing each device was randomized for each participant.

The driving route was a fixed circuitous route with only one stop sign at the midway point (i.e., at approximately ten minutes) and no traffic lights. The fixed route took approximately 20 minutes, and the drive-to-drive variability was less than 10%. Subjects were only tested on the first half of the ride, up to the stop sign. Subjects were provided with rests between sessions.

Based on feedback from the participants, the study showed that the participants did not experience motion sickness continuously but generally did when the vehicle accelerated, decelerated, or made turns. Participants reported motion sickness as a cumulative effect, with the first turn inducing mild discomfort, the second turn adding to the effect of the first turn and so on, until a threshold was reached. While using the experimental vibratory device, participants reported that during the accelerations and turns, they felt discomfort, but this discomfort quickly returned to zero once the car went back to a constant speed, with no effect of accumulated nausea during the successive changes in the car's acceleration.

Figure 24:
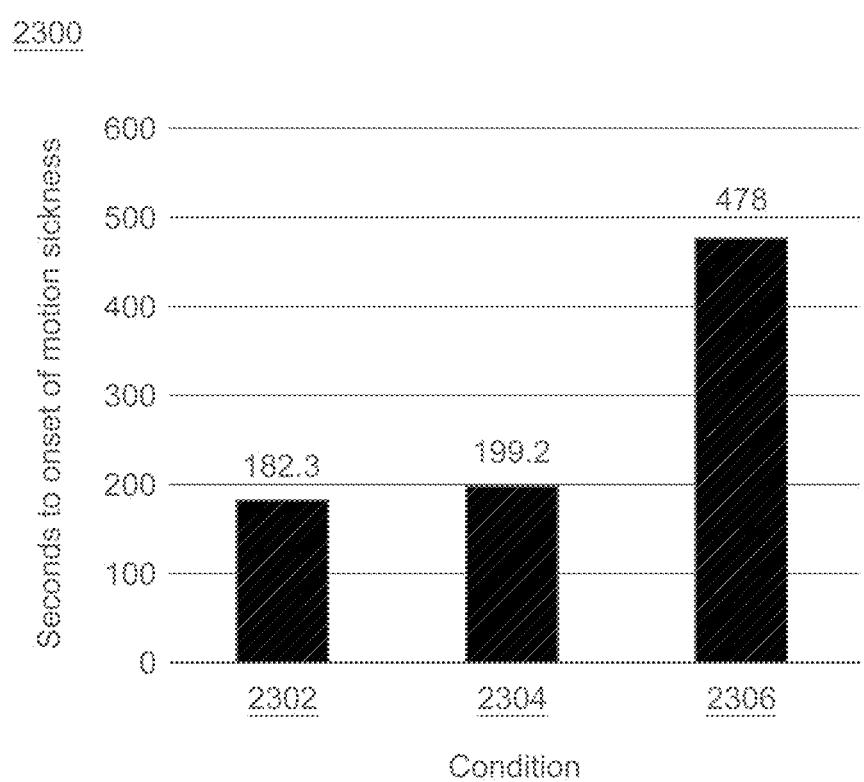
FIG. 24 depicts results from a study conducted to test a vibratory device for treating symptoms associated with vestibular conditions, using a test procedure, in yet another instance.

FIG. 24 depicts seconds to the initial onset of motion sickness that was experienced by participants during the third experimental study. Bar 2302 represents the seconds until initial onset of motion sickness with no device, bar 2304 represents the seconds until initial onset of motion sickness with the sound generator, and bar 2306 represents the second until initial onset of motion sickness with the experimental vibratory device. As shown, the use of the experimental vibratory device described herein led to a significant increase in the seconds to onset of motion sickness, at bar 2306. Specifically, the experimental vibratory device was found to be effective in that it more than doubled the time to onset of motion sickness compared to not wearing a device (bar 2302) and wearing a sound generator (bar 2304). The data of this study shows the effectiveness of the experimental vibratory device at preventing motion sickness in a simulated real-world situation of reading while riding as a passenger in the back seat of a car. None of the subjects who used the experimental vibratory device reported any feeling of discomfort once they got out of the car.

Summary of Experimental Studies and Other Indications

The results from the experimental studies described above show that a vibratory device, such as the example vibratory devices disclosed herein, can be effective at treating symptoms of various vestibular conditions. Such a device can have a small profile and be capable of coupling to a surface of a subject's head such that vibrations can be conducted via bone (e.g., the skull) to the subject's vestibular system. The experimental vibratory device used in the three experimental studies has been shown to be effective at mitigating and reducing motion and/or virtual reality induced motion sickness. The described experiments and results demonstrate that the effectiveness of the disclosed vibratory device in reducing motion sickness is substantially instantaneous, with no overt deleterious side-effects.

Subsequent experiments have shown that the force levels and frequency levels discovered to be effective herein were also effective at reducing vertigo and nausea brought on by caloric testing conducted at medical facilities. For example, for vertigo, individuals who suffered from chronic or frequent vertigo episodes were asked to wear the experimental vibratory device and report the effects of wearing the device. Generally, individuals reported less symptoms associated with vertigo when using the device. As another example, for caloric testing, an ear, nose and throat ("ENT") physician performed caloric testing on five subjects with and without wearing an experimental vibratory device. When not wearing the device on a first day, all subjects experienced nausea with one subject being unable to complete the test due to severe nausea. When wearing the device on a subsequent day, all five subjects reported significantly less nausea, including no nausea, and the subject unable to complete the test the first day was able to complete it wearing the device the second day. The tests on both days indicated same levels of vestibular function, with and without the vibratory device.

The application of vibratory signals to mask signals sent by the vestibular system that induce sickness, also known as vestibular masking, through the application of bone conducted vibratory signals, can be effective at mitigating numerous vestibular conditions. For example, vertigo brought on by a damaged vestibular system can be treated with applied bone-conducted vibratory signals. At times, however, vibratory signals can have adverse reactions if the applied vibratory signals are suddenly removed (e.g., when the vibratory device is turned off). In some embodiments, such as those detailed above, these adverse reactions can be minimized by gradually reducing the power of the applied vibrations over a period (i.e., having a ramp down in power) instead of abruptly turning off the device.

As another example, vestibular masking can be effective in mitigating motion sickness that occurs when individuals use virtual reality devices, such as those disclosed herein. Because virtual reality devices do not result in motion sickness at all times, in an embodiment, a vibrating device such that those disclosed herein can be operable to generate vibrations for masking the vestibular system when certain conditions and/or situations associated with inducing sickness are displayed and/or presented to a user of the virtual reality device. The vibrating device may be controlled, for example, by a microcontroller that is operable to store specialized instructions for controlling the vibrating element. Such instructions may be stored in onboard memory or in a separate memory. In addition, such instructions are designed to integrate specialized functions and features into the controller to perform certain functions, methods and processes related to treating conditions of the vestibular system. In an embodiment, the microcontroller can be programmed with instructions using a software development kit ("SDK").

It should be understood that electrical signals to control and/or drive the generation of vibratory signals may be generated by a microcontroller based on the stored instructions. These electrical signals may be communicated between the microcontroller and a vibratory device via wired or wireless (e.g., Bluetooth) methods. Further, the electrical signals may include a stored pattern of operation. For example, the stored instructions accessed by the microcontroller may be used by the microcontroller to generate a series of electrical signals that are sent to the vibrating element to cause the vibrating element to be turned "on" or "off" in a pattern that is advantageous to a specific user based on usage data that has been accumulated and stored in a device that includes the microcontroller and vibrating element. One pattern may involve a series of vibrations where the number of vibrations generated and applied over a time period (e.g., per minute) to a subject may be varied, while a second pattern may include a series of vibrations where the force level in a number of vibrations may be varied. Other types of electrical signals, such as those that may be used to control the force level and frequency of vibrations generated by the vibrating element, may be sent to the vibratory device from the microcontroller based on data received from sensors. For example, an acceleration sensor may be included in a portable electronic device (e.g., mobile phone) to sense changes in a user's physical acceleration. In an embodiment, the microcontroller may be operable to receive data from the acceleration sensor indicating a type of acceleration that may lead to motion sickness. Accordingly, after receiving such data, the microcontroller may be operable to generate associated control signals and send such signals to the vibrating element. The vibrating element, in turn, may be operable to receive such control signals and generate vibrations that can be applied to the proprioceptive vestibular system in real-time to, for example, to pre-emptively minimize motion sickness. Alternatively, a stored roadmap that represents a path or course that may result in a user becoming sick due to motion sickness may be stored in the microcontroller or in the portable device along with GPS circuitry. In an embodiment, as the GPS circuitry indicates that the user is moving along the path or course and arrives at a position that may induce motion sickness, the microcontroller may be operable to generate associated control signals and send such signals to the vibrating element. The vibrating element, in turn, may be operable to receive such control signals and generate vibrations that can be applied to the vestibular system to, for example, to account for the possibility of motion sickness before the user reaches the position, for example.

It should be noted that several different types of medical tests, including caloric, VNG, and ENG tests are administered by audiologists and otolaryngologists to test the vestibular function of subjects. As a part of a test, a form of vertigo may be induced in the patient which may have the adverse side effect of causing nausea. Vestibular masking can be used to reduce the nausea experienced by such patients while undergoing these tests. Accordingly, the devices described herein may be included in a medical testing system that is used to complete such medical tests, or, alternatively, may be used (e.g., worn) in conjunction with such medical testing systems to relieve or reduce such adverse side effects.

In some embodiments, the apparatuses and methods described can be used for applications not related to treating of vestibular conditions. For example, some embodiments of the vibratory device can be used as a device to carry out haptic communication using suitable communication channels. In some instances, a method of communication that is silent and based on haptic sensation may be of use, such as in military or surveillance conditions. An embodiment of the vibratory device can be used, with suitable adaptations of reduced detectability such as invisible and inaudible use condition, to allow haptic communication between subjects such as operatives.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. An apparatus, comprising:
   a vibratory device configured to produce one or more vibratory signals having a frequency of less than 200 Hz and a force level greater than 87 dB re 1 dyne and less than or equal to 101 dB re 1 dyne, the vibratory device including:
      a housing defining a chamber;
      a magnet disposed within the chamber and configured to oscillate about an equilibrium position to produce the one or more vibratory signals; and
      a coil configured to generate a magnetic field, the magnetic field being configured to cause the magnet to oscillate; and
   a head-mounted structure configured to position the vibratory device over a portion of a head of a user to apply the one or more vibratory signals produced by the vibratory device to the portion of the head of the user such that a portion of the one or more vibratory signals is conducted via bone to a vestibular system of the user and causes movement of a portion of the vestibular system that treats a physiological condition associated with the vestibular system.

2. The apparatus of claim 1, wherein the vibratory device further includes a set of metallic components coupled to ends of the magnet and configured to reduce stray magnetic flux and direct a magnetic field of the magnet in a direction for enabling oscillation of the magnet.

3. The apparatus of claim 1, further comprising:
   a sensor configured to measure an electrical characteristic of the vibratory device, the electrical characteristic including at least one of a voltage, a current, an impedance, a magnetic field, or an acceleration associated with one or more components of the vibratory device;

a processor operatively coupled to the vibratory device and the sensor, the processor configured to adjust a frequency of an electrical signal supplied to the coil to generate the magnetic field based on measurements received from the sensor.

4. The apparatus of claim 1, further comprising:

a sensor configured to measure a biological characteristic of the user that is indicative of an onset of the physiological condition or a change in severity of the physiological condition; and a processor operatively coupled to the vibratory device and the sensor, the processor configured to control the vibratory device to produce the one or more vibratory signals based on measurements received from the sensor.

5. The apparatus of claim 4, wherein the biological characteristic includes at least one of: body temperature, skin conductance, electrical activity of a brain of the user, electrical activity of muscle tissue of the user, electrical activity of a heart of the user, heart rate, changes associated with an eye of the user, blood pressure, oxygen saturation, nerve evoked potentials, sweat toxicology, or level of stress hormones.

6. The apparatus of claim 4, wherein the processor is configured to control the vibratory device by activating the vibratory device to produce the one or more vibratory signals or increasing power supplied to the vibratory device to increase the force level of the one or more vibratory signals.

7. The apparatus of claim 1, wherein the vibratory device further comprises one or more elastic elements configured to suspend the magnet in the chamber such that the magnet can oscillate about the equilibrium position.

8. The apparatus of claim 7, wherein the one or more elastic elements includes a spring having a first end attached to the housing and a second end disposed within an opening formed in the magnet.

9. The apparatus of claim 7, wherein the one or more elastic elements includes at least two springs each defining an opening through which the magnet moves when the magnet oscillates about the equilibrium position.

10. The apparatus of claim 7, wherein the one or more elastic elements includes at least two annular pieces of elastic material disposed about an outer perimeter of the magnet at different positions along a longitudinal length of the magnet.

11. The apparatus of claim 7, wherein the vibratory device further includes one or more end plates each coupled to the magnet, at least one elastic element from the one or more elastic elements is coupled to at least one end plate from the one or more end plates.

12. The apparatus of claim 1, wherein the physiological condition includes at least one of: vertigo, dizziness, motion sickness, virtual reality sickness, spatial discordance, sopite syndrome, nausea, headache, migraine, or tinnitus.

13. The apparatus of claim 1, wherein the head-mounted structure is a head gear configured to be worn by the user including at least one of head phones or earphones.

14. The apparatus of claim 1, wherein the head-mounted structure is a head band configured to be worn by the user.

15. The apparatus of claim 1, wherein the head-mounted structure is an eyewear configured to be worn by the user including at least one of: eyeglasses, goggles, sunglasses, or safety glasses.

16. The apparatus of claim 1, wherein the head-mounted structure is a headset configured to be worn by the user as a virtual reality device.

17. The apparatus of claim 1, wherein the magnet is a first magnet and the vibratory device further comprises a pair of magnets including a second magnet and a third magnet, the pair of magnets configured to suspend the first magnet in the chamber such that the first magnet can oscillate about the equilibrium position.

18. The apparatus of claim 1, wherein the coil is further configured such that the magnetic field generated is an alternating magnetic field that causes the magnet to oscillate along a longitudinal axis of the vibratory device.

19. The apparatus of claim 1, wherein the coil is further configured such that the magnetic field generated causes the magnet to oscillate along a longitudinal axis of the vibratory device while being restricted from vibrating along axes other than the longitudinal axis.

20. The apparatus of claim 1, further comprising:

a sensor configured to determine a measurement of a biological characteristic of the user that is indicative of an onset of the physiological condition or a change in severity of the physiological condition; and a processor operatively coupled to the vibratory device and the sensor, the processor configured to control the vibratory device to modify at least one of the force level or the frequency of the one or more vibratory signals based on the measurement.

* * * * *